United States Patent
Yu et al.

(10) Patent No.: US 10,294,466 B2
(45) Date of Patent: May 21, 2019

(54) ALPHA-GLUCOSIDASE, COMPOSITIONS AND METHODS

(71) Applicant: DANISCO US INC., Palo Alto, CA (US)

(72) Inventors: Zheyong Yu, Shanghai (CN); Zhenghong Zhang, Shanghai (CN); Jing Ge, Shanghai (CN); Zhen Qian, Shanghai (CN); Guoqing Liu, Shanghai (CN); Zhiyong Xie, Shanghai (CN); Zhongmei Tang, Shanghai (CN)

(73) Assignee: DANISCO US INC., Palo Alto, CA (US)

( * ) Notice: Subject to any disclaimer, the term of this patent is extended or adjusted under 35 U.S.C. 154(b) by 0 days.

(21) Appl. No.: 15/553,134

(22) PCT Filed: Feb. 25, 2016

(86) PCT No.: PCT/US2016/019649
§ 371 (c)(1),
(2) Date: Aug. 23, 2017

(87) PCT Pub. No.: WO2016/138315
PCT Pub. Date: Sep. 1, 2016

(65) Prior Publication Data
US 2018/0016563 A1 Jan. 18, 2018

(30) Foreign Application Priority Data
Feb. 25, 2015 (WO) ............... PCT/CN2015/073269

(51) Int. Cl.
*C12N 9/26* (2006.01)
*C12N 1/20* (2006.01)
(Continued)

(52) U.S. Cl.
CPC .............. *C12N 9/2408* (2013.01); *A23L 2/52* (2013.01); *A23L 33/18* (2016.08); *C12C 5/004* (2013.01);
(Continued)

(58) Field of Classification Search
None
See application file for complete search history.

(56) References Cited

U.S. PATENT DOCUMENTS 6,022,725 A 2/2000 Fowler et al.
2013/0323798 A1* 12/2013 Ge ........................... C12C 7/04
435/99

(Continued)

FOREIGN PATENT DOCUMENTS

| WO | 2014/202616 A2 | 12/2014 |
| WO | 2014/202622 A2 | 12/2014 |
| WO | 2015/130881 A1 | 9/2015 |

OTHER PUBLICATIONS

Guo et al., "Protein tolerance to random amino acid change", Proceedings of the National Academy of Sciences USA, vol. 101, No. 25, pp. 9205-9210, 2004.*

(Continued)

*Primary Examiner* — Richard C Ekstrom

(57) ABSTRACT

The present disclosure relates to polypeptides having alpha-glucosidase activity isolated, derived or derivable from *Rasamsonia* or engineered polypeptides having alpha-glucosidase activity isolated, derived or derivable from *Rasamsonia* homologs. The present disclosure also pertains to polynucleotides encoding the polypeptides, nucleic acid constructs, vectors, host cells and mutant cells comprising the polynucleotides. The disclosure further pertains to compositions comprising such polypeptides, methods of producing the polypeptides and compositions, as well as methods (Continued)

Plasmid map of pGX256-TauSec098 for using such polypeptides and compositions for industrial applications.

24 Claims, 1 Drawing Sheet

Specification includes a Sequence Listing.

(51) Int. Cl.
| | |
|---|---|
| C12N 1/14 | (2006.01) |
| C12P 19/14 | (2006.01) |
| C12P 19/16 | (2006.01) |
| C12P 19/18 | (2006.01) |
| C12P 19/22 | (2006.01) |
| C12P 7/10 | (2006.01) |
| C12C 5/00 | (2006.01) |
| C12C 12/02 | (2006.01) |
| A23L 33/18 | (2016.01) |
| A23L 2/52 | (2006.01) |
| C12P 19/02 | (2006.01) |

(52) U.S. Cl.
CPC ............... *C12C 12/02* (2013.01); *C12N 1/14* (2013.01); *C12N 1/20* (2013.01); *C12P 7/10* (2013.01); *C12P 19/02* (2013.01); *C12P 19/14* (2013.01); *C12P 19/16* (2013.01); *C12P 19/18* (2013.01); *C12P 19/22* (2013.01); *C12Y 302/0102* (2013.01); *A23V 2002/00* (2013.01); *Y02E 50/16* (2013.01)

(56) References Cited

U.S. PATENT DOCUMENTS

| | | | |
|---|---|---|---|
| 2015/0240278 A1* | 8/2015 | Nagy .................... | C12P 19/14 435/97 |
| 2015/0240279 A1* | 8/2015 | Nagy .................... | C12P 19/14 435/97 |
| 2018/0016563 A1* | 1/2018 | Yu ....................... | C12N 9/2408 |

OTHER PUBLICATIONS

McCarter et al., "Mechanisms of enzymatic glycoside hydrolysis," Curr. Opin. Struct. Biol., 1994, vol. 4, pp. 885-892.
Waters et al., "Characterisation of a thermostable enzyme cocktail with applications in wheat dough rheology," Enzyme and Microbial Technology, 2011, vol. 49, No. 2, pp. 229-223.
Svensson et al., "Fascinating facets of function and structure of amylolytic enzymes of glycoside hydrolase family 13," Biologia, Bratislava, 2002, vol. 57, Suppl. 11, pp. 5-19.
Su et al., "Rasamsonia composticola, a new thermophilic species isolated from compost in Yunnan, China," Mycol. Progress, 2013, vol. 12, pp. 213-221.
PCT International Search Report and the Written Opinion of the International Searching Authority for International Application No. PCT/US2016/019649; ISA/EPO; dated Apr. 21, 2016.
McCarter et al., "Mechanisms of enzymatic glycoside hydrolysis," Curr. Opin. Struct. Biol., 1994, vol. 4, pp. 885-392.
Maneesan et al., "Production of 1,5-anhydro-d-fructose by an a-glucosidase belonging to glycoside hydrolase family 31," Biosci. Biotech. Biochem., 2014, vol. 78, pp. 2064-2068.
Mala et al., "Towards regioselective synthesis of oligosaccharides by use of a-glucosidases with different substrate specificity," Carbohydr. Res., 1999, vol. 322, pp. 209-218.
Lovering et al., "Mechanistic and Structural Analysis of a Family 31 a-Glycosidase and Its Glycosyl-enzyme Intermediate," J. Biol. Chem., 2005, vol. 280, pp. 2105-2115.
Kimura, "Molecular Anatomy of a-Glucosidase," Trends Glycosci. Glycotechnol., 2000, vol. 12, pp. 373-380.
Kimura et al., "Complete Amino Acid Sequence of Crystalline a-Glucosidase from Aspergillus niger," Biosci. Biotechnol. Biochem., 1992, vol. 56, pp. 1368-1370.
Houbraken et al., "Rasamsonia, a new genus comprising thermotolerant and thermophilic *Talaromyces* and *Geosmithia* species," Antonie van Leeuwenhoek, 2012, vol. 101, pp. 403-421.
Henrissat et al., "New families in the classification of glycosyl hydrolases based on amino acid sequence similarities," Biochem. J., 1993, vol. 293, pp. 781-788.
Frandsen et al., "Plant a-glucosidases of the glycoside hydrolase family 31. Molecular properties, substrate specificity, reaction mechanism, and comparison with family members of different origin," Plant Mol. Biol., 1998, vol. 37, pp. 1-13.
Davies et al., "Structures and mechanisms of glycosyl hydrolases," Structure, 1995, vol. 3, pp. 853-859.

* cited by examiner

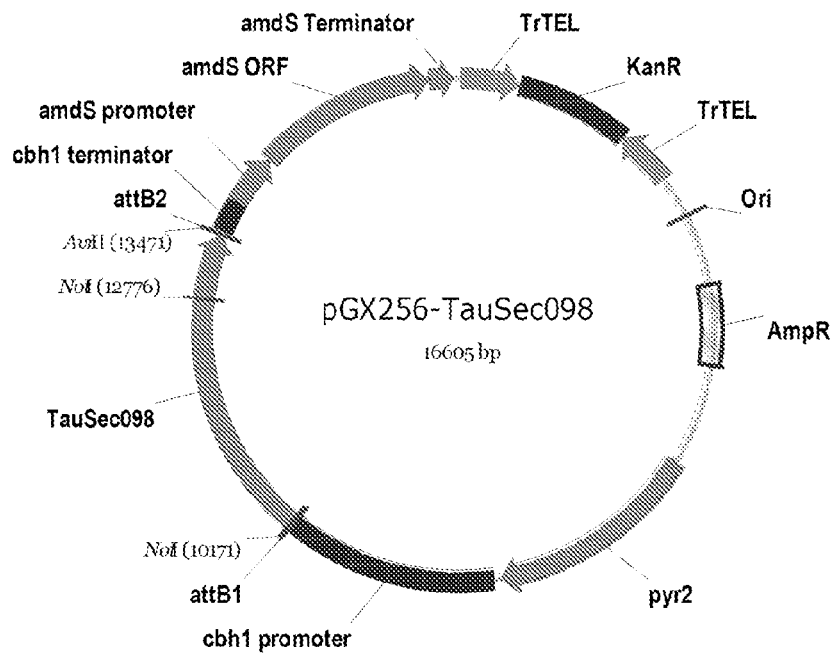
Figure 1: Plasmid map of pGX256-TauSec098
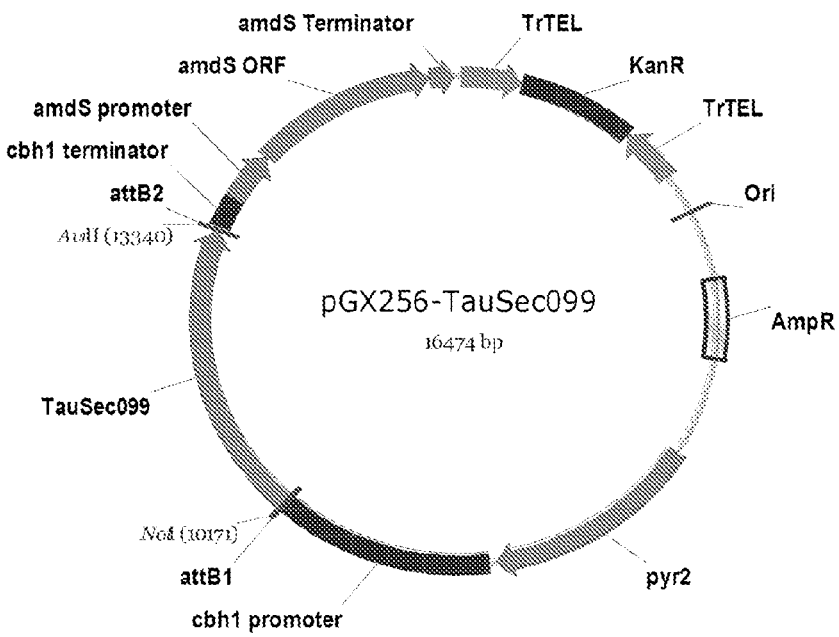
Figure 2: Plasmid map of pGX256-TauSec099

SEQUENCE LISTING

```
<160> NUMBER OF SEQ ID NOS: 8

<210> SEQ ID NO 1
<211> LENGTH: 3293
<212> TYPE: DNA
<213> ORGANISM: Rasamsonia-composticola

<400> SEQUENCE: 1
atgcggccaa cttccctcgt caagcacttg gctgcgacca gcctcctctt tctcgcggcg      60
gatgcagctg ctatcgtccg ccgcaacggc gcctctcctt catgccccgg ctataaagcg     120
agtaacgtga agaccgtcga cggtgaaatc gtcagcgcgg atctcaatct cgcgggtccc     180
gcctgcaatg tgtatggcac ggatctggac gatctgaagc tgcaggttga gtaccaatca     240
ggtaagtcgc acagcatcgc cgtctgcagc ttatcggcag catgtgatcg gcgcctggac     300
tagggcttag ggcctggggt tagggctgac tgcttgctgc cgttcgatgt gactggaact     360
gtacggttgg ttgacaacga tctgacatct gcagaacaac gcctccatgt gaagatctac     420
gatgccgccg agcaggtcta ccaggtgccc accgcggtgc ttccccggcc agcagcgcc     480 aacatccccc cggccaagtc ggacctgaag ttctccatga ccaacgaccc cttctccttt     540
accatcaagc gcagatcaaa cggcgaaatc ctcttcgaca cctccggcca tccgctgatc     600
ttcgagtcgc agtatctggg cctccgtacc aagctgccgg actcgcccaa catctacggc     660
ctgggagagc acaccggttc tttccgcctg cccaccaaga attcacccg cacgctgtgg     720 tcgcgcgatg cgtacggtac gcccaaagac accaacctgt acggcaacca cccggtgtac     780
ttcgactacc gcggcagcaa cggcacccat ggcgtgttcc tgctgaacag caacggcatg     840
gacgtcgata tcgacgtcga ctcggacgga cagtacctgc agtacaacac cctgggggc     900 gtgctggact tctacttcct cagcgggccg gatcccaagg ccgtcgcgac gcagtatgcc     960
gagacggtcg gaaaaccggt catgatgccc tactggggat tcggcttcca caactgcaga    1020
tatggatacc aggacatcta tgaggttgct gagatcattg ccaactacag tgccgcaaac    1080
attccgcttg agacccaatg gactgatatc ggtatgcttt ccatcccggt gccgtggttt    1140
ttgcttctca gcgtggctga ctgttgcaga ctatatggat ctgaggaaag tgtttacgct    1200 ggaccccta cgctatccat tgaagctcgt ccaagaggtt gtctcttatc tccacaagca    1260
caaccagcac tacatcatga tggtggaccc tgcagtggca taccagaact attcagcgtt    1320
caacaacggc gtcgctgccg acgctttcct gaagttctcg aatggctcca tctaccaggg    1380
tgtcgtctgg ccggggccga cggcgttccc ggactggttc gcacccagaa cacaggagtt    1440
ttggaatagc gagttctcga ccttctttga ccccgcccac ggcgtcgaca tcgatgccct    1500
ttggatcgac atgaacgagg cgtccaactt ctgcgacttt ccctgctcga accccgccgc    1560
```

-continued

```
gtatgcggca gccaacggcg atccgcccac gcctccgccg gtccgcttga gccccccgag      1620
gccgattcct ggatttggcc ctgacttcca gccgacgtgt gtcgcacgg tgtcgttcga       1680 ttgcgatgcg cagacctact ttggcgagaa catcctcatc ctgggtaact cgacgacact      1740
gggagccggc gacgttcaca tggcgccagt catgagcgcg aacaactacc cgatctggca      1800
gctgaccgtc cagatgccgc cgaatgggac gttctcgtac cagtacgttc gcaaggaatc      1860
ggacggcagt tacatctacg aacagacgaa tcgcacggtc acgacgggcg actgcaccag      1920
cggcacgctt aaggtgtccg acaccatcac caccagctct ggaccgcaca agagatccga     1980
attacgcccg ctggtgcgct cgccgttccc ggcggaggac ctgaccaggc gccagtctgg     2040
atcgatgttg ggcctgccca acaggaacct gctgaatccg ccatacacca tccacaatgc    2100
ggctggcaac ctgagtgaga agaccatcaa caccgacctg atccatgcgg gcggatatgc    2160
cgagtacgac acgcacaact tgtacggcac gatgatgagc gcgaccagca gggaggcgat    2220
gctgaaccgc agaccagcag tcaggccact tgtgtaagtc atccatcgtc cttaagccag    2280
acacagcatg ttaggggcta acgggcagta gcattacccg gtcgaccttc gctggagccg    2340
gccgacaggt cggccactgg ctcggcgaca atttcgccga ttgggaccac taccggtgga    2400
cgatcgccga gctgcaggaa ttcgcggcgc tgttccagat cccgatggtc ggcagcgaca    2460
tctgcgggta cgacggcaac acgacggaca acctgtgctc cgctgggtc ttcctcggcg    2520 ccttctcgcc cttcttccgc gaccactcgg acaaccagtc gccgccgcac gagctgtacc    2580
gcactccgca gatcgcggcg gccgcgcgcg ccgccatcga catccgctac cgtctgctcg    2640
actacgcgta cacggtgctg tggacgcaga cccagaccgg cgcgccgatg ctcaacccca    2700
tgttcttcga gtaccggcc gacagcaaca ccgccgacct gcagtaccag ttcttctggg    2760
gcgacagcat catggtcgcg cccgtgaccg acaacgactc gaccaccgtc aacgtctact    2820
tcccgaagga ccagttctac gacttctaca ccggcgcacc tgtgtccggg gagggcaata    2880
ccgtcaccct gaccgacgtc ggcttcgaca ccatcccgct gtacttcaag ggcgggagca    2940
tcgtgcccat gcgcgtgcgc tcggcgaaca cgacggcgga gctgcggcag caggacttcg    3000
tcgtcgtcat cgccccggac agccacggcg acgcgacggg ccagctgtac ctcgacgacg    3060
gcgagagcat caaccagccg cacaccagcg agatccagtt ctcgtaccgc ggaggccatt    3120
tcagcatgac aggcaagttt gactatgatc ccggcaacgt ggtcatcagc cagatcacgc    3180
tgctgggtgc ggacggcgcc ggtaaagggg gttcgtataa cagcaccacc aaggtggcga    3240
cctacaaagt caacgcgaag ttgacgggta aattcgaagc cagcttacac taa          3293
```

<210> SEQ ID NO 2
<211> LENGTH: 3227
<212> TYPE: DNA
<213> ORGANISM: artificial sequence
<220> FEATURE:
<223> OTHER INFORMATION: Coding-sequence-of-predicted-mature-form-of-TauSec098

<400> SEQUENCE: 2

```
gctgctatcg tccgccgcaa cggcgcctct ccttcatgcc ccggctataa agcgagtaac       60
gtgaagaccg tcgacggtga atcgtcagc gcggatctca atctcgcggg tcccgcctgc     120
aatgtgtatg gcacggatct ggacgatctg aagctgcagg ttgagtacca atcaggtaag      180
tcgcacagca tcgccgtctg cagcttatcg gcagcatgtg atcggcgcct ggactagggc      240
ttagggcctg gggttagggc tgactgcttg ctgccgttcg atgtgactgg aactgtacgg      300
```

```
ttggtttgaca acgatctgac atctgcagaa caacgcctcc atgtgaagat ctacgatgcc    360
gccgagcagg tctaccaggt gcccaccgcg gtgcttcccc ggcccagcag cgccaacatc    420
cccccggcca agtcggacct gaagttctcc atgaccaacg accccttctc ctttaccatc    480
aagcgcagat caaacggcga aatcctcttc gacacctccg gccatccgct gatcttcgag    540
tcgcagtatc tgggcctccg taccaagctg ccggactcgc caacatcta cggcctggga    600
gagcacaccg gttctttccg cctgcccacc aagaattaca cccgcacgct gtggtcgcgc    660
gatgcgtacg gtacgcccaa agacaccaac ctgtacggca accacccggt gtacttcgac    720
taccgcggca gcaacggcac ccatggcgtg ttcctgctga cagcaacgg catgacgtc     780
gatatcgacg tcgactcgga cggacagtac ctgcagtaca cacccctggg gggcgtgctg    840
gacttctact cctcagcgg gccggatccc aaggccgtcg cgacgcagta tgccgagacg    900
gtcggaaaac cggtcatgat gccctactgg ggattcggct tccacaactg cagatatgga    960
taccaggaca tctatgaggt tgctgagatc attgccaact acagtgccgc aaacattccg   1020
cttgagaccc aatggactga tatcggtatg cttttccatcc cggtgccgtg gttttttgctt   1080
ctcagcgtgg ctgactgttg cagactatat ggatctgagg aaagtgttta cgctggaccc   1140
ctatcgctat ccattgaagc tcgtccaaga ggttgtctct tatctccaca agcacaacca   1200
gcactacatc atgatggtgg accctgcagt ggcataccag aactattcag cgttcaacaa   1260
cggcgtcgct gccgacgctt tcctgaagtt ctcgaatggc tccatctacc agggtgtcgt   1320
ctggccgggg ccgacggcgt tcccggactg gttcgcaccc cagacacagg agtttttggaa   1380
tagcgagttc tcgaccttct tgacccccgc ccacggcgtc gacatcgatg ccctttggat   1440
cgacatgaac gaggcgtcca acttctgcga cttttccctgc tcgaaccccg ccgcgtatgc   1500
ggcagccaac ggcgatccgc ccacgcctcc gccggtccgc ttgagccccc cgaggccgat   1560
tcctggattt ggccctgact ccagccgac gtgtgtcgcc acggtgtcgt tcgattgcga    1620
tgcgcagacc tacttttggcg agaacatcct catcctgggt aactcgacga cactgggagc   1680
cggcgacgtt cacatggcgc cagtcatgag cgcgaacaac tacccgatct ggcagctgac   1740
cgtccagatg ccgccgaatg ggacgttctc gtaccagtac gttcgcaagg aatcggacgg   1800
cagttacatc tacgaacaga cgaatcgcac ggtcacgacg ggcgactgca ccagcggcac   1860
gcttaaggtg tccgacacca tcaccaccag ctctggaccg cacaagagat ccgaattacg   1920
gccgctggtg cgctcgccgt tcccggcgga ggacctgacc aggcgccagt ctggatcgat   1980
gttgggcctg cccaacagga acctgctgaa tccgccatac accatccaca atgcggctgg   2040
caacctgagt gagaagacca tcaacaccga cctgatccat gcgggcggat atgccgagta   2100
cgacacgcac aacttgtacg gcacgatgat gagcgcgacc agcagggagg cgatgctgaa   2160
ccgcagacca gcagtcaggc cacttgtgta agtcatccat cgtccttaag ccagacacag   2220
catgttaggg gctaacgggc agtagcatta cccggtcgac cttcgctgga gccggccgac   2280
aggtcggcca ctggctcggc gacaatttcg ccgattggga ccactaccgg tggacgatcg   2340
ccgagctgca ggaattcgcg gcgctgttcc agatcccgat ggtcggcagc gacatctgcg   2400
ggtacgacgg caacacgacg gacaacctgt gctcgcgctg ggtcttcctc ggcgccttct   2460
cgcccttctt ccgcgaccac tcggacaacc agtcgccgcc gcacgagctg taccgcactc   2520
cgcagatcgc ggcggccgcg cgcgccgcca tcgacatccg ctaccgtctg ctcgactacg   2580
cgtacacggt gctgtggacg cagacccaga ccggcgcgcc gatgctcaac cccatgttct   2640
```

-continued

```
tcgagtaccc ggccgacagc aacaccgccg acctgcagta ccagttcttc tggggcgaca      2700
gcatcatggt cgcgcccgtg accgacaacg actcgaccac cgtcaacgtc tacttcccga      2760
aggaccagtt ctacgacttc tacaccggcg cacctgtgtc cggggagggc aataccgtca      2820
ccctgaccga cgtcggcttc gacaccatcc cgctgtactt caagggcggg agcatcgtgc      2880
ccatgcgcgt gcgctcggcg aacacgacgg cggagctgcg gcagcaggac ttcgtcgtcg      2940
tcatcgcccc ggacagccac ggcgacgcga cgggccagct gtacctcgac gacgcgaga       3000
gcatcaacca gccgcacacc agcgagatcc agttctcgta ccgcggaggc catttcagca      3060
tgacaggcaa gtttgactat gatcccggca acgtggtcat cagccagatc acgctgctgg      3120
gtgcggacgg cgccggtaaa gggggttcgt ataacagcac caccaaggtg gcgacctaca      3180
aagtcaacgc gaagttgacg ggtaaattcg aagccagctt acactaa                    3227
```

<210> SEQ ID NO 3
<211> LENGTH: 1035
<212> TYPE: PRT
<213> ORGANISM: Rasamsonia-composticola

<400> SEQUENCE: 3

```
Met Arg Pro Thr Ser Leu Val Lys His Leu Ala Thr Ser Leu Leu
1               5                   10                  15

Phe Leu Ala Ala Asp Ala Ala Ile Val Arg Arg Asn Gly Ala Ser
            20                  25                  30

Pro Ser Cys Pro Gly Tyr Lys Ala Ser Asn Val Lys Thr Val Asp Gly
        35                  40                  45

Glu Ile Val Ser Ala Asp Leu Asn Leu Ala Gly Pro Ala Cys Asn Val
50                  55                  60

Tyr Gly Thr Asp Leu Asp Asp Leu Lys Leu Gln Val Glu Tyr Gln Ser
65                  70                  75                  80

Gly Pro Gly Val Arg Ala Asp Cys Leu Leu Pro Phe Asp Val Thr Gly
                85                  90                  95

Thr Val Arg Leu Val Asp Asn Asp Leu Thr Ser Ala Glu Gln Arg Leu
            100                 105                 110

His Val Lys Ile Tyr Asp Ala Ala Glu Gln Val Tyr Gln Val Pro Thr
        115                 120                 125

Ala Val Leu Pro Arg Pro Ser Ser Ala Asn Ile Pro Pro Ala Lys Ser
130                 135                 140

Asp Leu Lys Phe Ser Met Thr Asn Asp Pro Phe Ser Phe Thr Ile Lys
145                 150                 155                 160

Arg Arg Ser Asn Gly Glu Ile Leu Phe Asp Thr Ser Gly His Pro Leu
                165                 170                 175

Ile Phe Glu Ser Gln Tyr Leu Gly Leu Arg Thr Lys Leu Pro Asp Ser
            180                 185                 190

Pro Asn Ile Tyr Gly Leu Gly Glu His Thr Gly Ser Phe Arg Leu Pro
        195                 200                 205

Thr Lys Asn Tyr Thr Arg Thr Leu Trp Ser Arg Asp Ala Tyr Gly Thr
210                 215                 220

Pro Lys Asp Thr Asn Leu Tyr Gly Asn His Pro Val Tyr Phe Asp Tyr
225                 230                 235                 240

Arg Gly Ser Asn Gly Thr His Gly Val Phe Leu Leu Asn Ser Asn Gly
                245                 250                 255

Met Asp Val Asp Ile Asp Val Asp Ser Asp Gly Gln Tyr Leu Gln Tyr
            260                 265                 270
```

```
Asn Thr Leu Gly Gly Val Leu Asp Phe Tyr Phe Leu Ser Gly Pro Asp
            275                 280                 285

Pro Lys Ala Val Ala Thr Gln Tyr Ala Glu Thr Val Gly Lys Pro Val
    290                 295                 300

Met Met Pro Tyr Trp Gly Phe Gly Phe His Asn Cys Arg Tyr Gly Tyr
305                 310                 315                 320

Gln Asp Ile Tyr Glu Val Ala Glu Ile Ile Ala Asn Tyr Ser Ala Ala
                325                 330                 335

Asn Ile Pro Leu Glu Thr Gln Trp Thr Asp Ile Asp Tyr Met Asp Leu
                340                 345                 350

Arg Lys Val Phe Thr Leu Asp Pro Tyr Arg Tyr Pro Leu Lys Leu Val
            355                 360                 365

Gln Glu Val Val Ser Tyr Leu His Lys His Asn Gln His Tyr Ile Met
    370                 375                 380

Met Val Asp Pro Ala Val Ala Tyr Gln Asn Tyr Ser Ala Phe Asn Asn
385                 390                 395                 400

Gly Val Ala Ala Asp Ala Phe Leu Lys Phe Ser Asn Gly Ser Ile Tyr
                405                 410                 415

Gln Gly Val Val Trp Pro Gly Pro Thr Ala Phe Pro Asp Trp Phe Ala
            420                 425                 430

Pro Gln Thr Gln Glu Phe Trp Asn Ser Glu Phe Ser Thr Phe Phe Asp
    435                 440                 445

Pro Ala His Gly Val Asp Ile Asp Ala Leu Trp Ile Asp Met Asn Glu
450                 455                 460

Ala Ser Asn Phe Cys Asp Phe Pro Cys Ser Asn Pro Ala Ala Tyr Ala
465                 470                 475                 480

Ala Ala Asn Gly Asp Pro Pro Thr Pro Pro Val Arg Leu Ser Pro
                485                 490                 495

Pro Arg Pro Ile Pro Gly Phe Gly Pro Asp Phe Gln Pro Thr Cys Val
                500                 505                 510

Ala Thr Val Ser Phe Asp Cys Asp Ala Gln Thr Tyr Phe Gly Glu Asn
            515                 520                 525

Ile Leu Ile Leu Gly Asn Ser Thr Thr Leu Gly Ala Gly Asp Val His
    530                 535                 540

Met Ala Pro Val Met Ser Ala Asn Asn Tyr Pro Ile Trp Gln Leu Thr
545                 550                 555                 560

Val Gln Met Pro Pro Asn Gly Thr Phe Ser Tyr Gln Tyr Val Arg Lys
                565                 570                 575

Glu Ser Asp Gly Ser Tyr Ile Tyr Glu Gln Thr Asn Arg Thr Val Thr
            580                 585                 590

Thr Gly Asp Cys Thr Ser Gly Thr Leu Lys Val Ser Asp Thr Ile Thr
            595                 600                 605

Thr Ser Ser Gly Pro His Lys Arg Ser Glu Leu Arg Pro Leu Val Arg
    610                 615                 620

Ser Pro Phe Pro Ala Glu Asp Leu Thr Arg Arg Gln Ser Gly Ser Met
625                 630                 635                 640

Leu Gly Leu Pro Asn Arg Asn Leu Leu Asn Pro Pro Tyr Thr Ile His
                645                 650                 655

Asn Ala Ala Gly Asn Leu Ser Glu Lys Thr Ile Asn Thr Asp Leu Ile
                660                 665                 670

His Ala Gly Gly Tyr Ala Glu Tyr Asp Thr His Asn Leu Tyr Gly Thr
            675                 680                 685

Met Met Ser Ala Thr Ser Arg Glu Ala Met Leu Asn Arg Arg Pro Ala
```

```
                690                 695                 700
Val Arg Pro Leu Val Ile Thr Arg Ser Thr Phe Ala Gly Ala Gly Arg
705                 710                 715                 720

Gln Val Gly His Trp Leu Gly Asp Asn Phe Ala Asp Trp Asp His Tyr
                725                 730                 735

Arg Trp Thr Ile Ala Glu Leu Gln Glu Phe Ala Ala Leu Phe Gln Ile
                740                 745                 750

Pro Met Val Gly Ser Asp Ile Cys Gly Tyr Asp Gly Asn Thr Thr Asp
                755                 760                 765

Asn Leu Cys Ser Arg Trp Val Phe Leu Gly Ala Phe Ser Pro Phe Phe
770                 775                 780

Arg Asp His Ser Asp Asn Gln Ser Pro Pro His Glu Leu Tyr Arg Thr
785                 790                 795                 800

Pro Gln Ile Ala Ala Ala Arg Ala Ile Asp Ile Arg Tyr Arg
                805                 810                 815

Leu Leu Asp Tyr Ala Tyr Thr Val Leu Trp Thr Gln Thr Gln Thr Gly
                820                 825                 830

Ala Pro Met Leu Asn Pro Met Phe Phe Glu Tyr Pro Ala Asp Ser Asn
                835                 840                 845

Thr Ala Asp Leu Gln Tyr Gln Phe Phe Trp Gly Asp Ser Ile Met Val
                850                 855                 860

Ala Pro Val Thr Asp Asn Asp Ser Thr Thr Val Asn Val Tyr Phe Pro
865                 870                 875                 880

Lys Asp Gln Phe Tyr Asp Phe Tyr Thr Gly Ala Pro Val Ser Gly Glu
                885                 890                 895

Gly Asn Thr Val Thr Leu Thr Asp Val Gly Phe Asp Thr Ile Pro Leu
                900                 905                 910

Tyr Phe Lys Gly Gly Ser Ile Val Pro Met Arg Val Arg Ser Ala Asn
                915                 920                 925

Thr Thr Ala Glu Leu Arg Gln Gln Asp Phe Val Val Ile Ala Pro
930                 935                 940

Asp Ser His Gly Asp Ala Thr Gly Gln Leu Tyr Leu Asp Asp Gly Glu
945                 950                 955                 960

Ser Ile Asn Gln Pro His Thr Ser Glu Ile Gln Phe Ser Tyr Arg Gly
                965                 970                 975

Gly His Phe Ser Met Thr Gly Lys Phe Asp Tyr Asp Pro Gly Asn Val
                980                 985                 990

Val Ile Ser Gln Ile Thr Leu Leu Gly Ala Asp Gly Ala Gly Lys Gly
                995                 1000                1005

Gly Ser Tyr Asn Ser Thr Thr Lys Val Ala Thr Tyr Lys Val Asn
        1010                1015                1020

Ala Lys Leu Thr Gly Lys Phe Glu Ala Ser Leu His
        1025                1030                1035

<210> SEQ ID NO 4
<211> LENGTH: 1013
<212> TYPE: PRT
<213> ORGANISM: artificial sequence
<220> FEATURE:
<223> OTHER INFORMATION: Predicted-mature-form-of-TauSec098

<400> SEQUENCE: 4

Ala Ala Ile Val Arg Arg Asn Gly Ala Ser Pro Ser Cys Pro Gly Tyr
1               5                   10                  15

Lys Ala Ser Asn Val Lys Thr Val Asp Gly Glu Ile Val Ser Ala Asp
```

-continued

```
                 20                  25                  30
Leu Asn Leu Ala Gly Pro Ala Cys Asn Val Tyr Gly Thr Asp Leu Asp
             35                  40                  45
Asp Leu Lys Leu Gln Val Glu Tyr Gln Ser Gly Pro Gly Val Arg Ala
 50                  55                  60
Asp Cys Leu Leu Pro Phe Asp Val Thr Gly Thr Val Arg Leu Val Asp
 65                  70                  75                  80
Asn Asp Leu Thr Ser Ala Glu Gln Arg Leu His Val Lys Ile Tyr Asp
             85                  90                  95
Ala Ala Glu Gln Val Tyr Gln Val Pro Thr Ala Val Leu Pro Arg Pro
            100                 105                 110
Ser Ser Ala Asn Ile Pro Pro Ala Lys Ser Asp Leu Lys Phe Ser Met
            115                 120                 125
Thr Asn Asp Pro Phe Ser Phe Thr Ile Lys Arg Ser Asn Gly Glu
            130                 135                 140
Ile Leu Phe Asp Thr Ser Gly His Pro Leu Ile Phe Glu Ser Gln Tyr
145                 150                 155                 160
Leu Gly Leu Arg Thr Lys Leu Pro Asp Ser Pro Asn Ile Tyr Gly Leu
            165                 170                 175
Gly Glu His Thr Gly Ser Phe Arg Leu Pro Thr Lys Asn Tyr Thr Arg
            180                 185                 190
Thr Leu Trp Ser Arg Asp Ala Tyr Gly Thr Pro Lys Thr Asn Leu
            195                 200                 205
Tyr Gly Asn His Pro Val Tyr Phe Asp Tyr Arg Gly Ser Asn Gly Thr
            210                 215                 220
His Gly Val Phe Leu Leu Asn Ser Asn Gly Met Asp Val Asp Ile Asp
225                 230                 235                 240
Val Asp Ser Asp Gly Gln Tyr Leu Gln Tyr Asn Thr Leu Gly Gly Val
            245                 250                 255
Leu Asp Phe Tyr Phe Leu Ser Gly Pro Asp Pro Lys Ala Val Ala Thr
            260                 265                 270
Gln Tyr Ala Glu Thr Val Gly Lys Pro Val Met Met Pro Tyr Trp Gly
            275                 280                 285
Phe Gly Phe His Asn Cys Arg Tyr Gly Tyr Gln Asp Ile Tyr Glu Val
            290                 295                 300
Ala Glu Ile Ile Ala Asn Tyr Ser Ala Ala Asn Ile Pro Leu Glu Thr
305                 310                 315                 320
Gln Trp Thr Asp Ile Asp Tyr Met Asp Leu Arg Lys Val Phe Thr Leu
            325                 330                 335
Asp Pro Tyr Arg Tyr Pro Leu Lys Leu Val Gln Glu Val Val Ser Tyr
            340                 345                 350
Leu His Lys His Asn Gln His Tyr Ile Met Met Val Asp Pro Ala Val
            355                 360                 365
Ala Tyr Gln Asn Tyr Ser Ala Phe Asn Asn Gly Val Ala Ala Asp Ala
            370                 375                 380
Phe Leu Lys Phe Ser Asn Gly Ser Ile Tyr Gln Gly Val Val Trp Pro
385                 390                 395                 400
Gly Pro Thr Ala Phe Pro Asp Trp Phe Ala Pro Gln Thr Gln Glu Phe
            405                 410                 415
Trp Asn Ser Glu Phe Ser Thr Phe Phe Asp Pro Ala His Gly Val Asp
            420                 425                 430
Ile Asp Ala Leu Trp Ile Asp Met Asn Glu Ala Ser Asn Phe Cys Asp
            435                 440                 445
```

```
Phe Pro Cys Ser Asn Pro Ala Ala Tyr Ala Ala Asn Gly Asp Pro
    450                 455                 460

Pro Thr Pro Pro Pro Val Arg Leu Ser Pro Pro Arg Pro Ile Pro Gly
465                 470                 475                 480

Phe Gly Pro Asp Phe Gln Pro Thr Cys Val Ala Thr Val Ser Phe Asp
                485                 490                 495

Cys Asp Ala Gln Thr Tyr Phe Gly Glu Asn Ile Leu Ile Leu Gly Asn
                500                 505                 510

Ser Thr Thr Leu Gly Ala Gly Asp Val His Met Ala Pro Val Met Ser
        515                 520                 525

Ala Asn Asn Tyr Pro Ile Trp Gln Leu Thr Val Gln Met Pro Pro Asn
    530                 535                 540

Gly Thr Phe Ser Tyr Gln Tyr Val Arg Lys Glu Ser Asp Gly Ser Tyr
545                 550                 555                 560

Ile Tyr Glu Gln Thr Asn Arg Thr Val Thr Thr Gly Asp Cys Thr Ser
                565                 570                 575

Gly Thr Leu Lys Val Ser Asp Thr Ile Thr Ser Ser Gly Pro His
                580                 585                 590

Lys Arg Ser Glu Leu Arg Pro Leu Val Arg Ser Pro Phe Pro Ala Glu
        595                 600                 605

Asp Leu Thr Arg Arg Gln Ser Gly Ser Met Leu Gly Leu Pro Asn Arg
    610                 615                 620

Asn Leu Leu Asn Pro Pro Tyr Thr Ile His Asn Ala Ala Gly Asn Leu
625                 630                 635                 640

Ser Glu Lys Thr Ile Asn Thr Asp Leu Ile His Ala Gly Gly Tyr Ala
                645                 650                 655

Glu Tyr Asp Thr His Asn Leu Tyr Gly Thr Met Met Ser Ala Thr Ser
            660                 665                 670

Arg Glu Ala Met Leu Asn Arg Arg Pro Ala Val Arg Pro Leu Val Ile
        675                 680                 685

Thr Arg Ser Thr Phe Ala Gly Ala Gly Arg Gln Val Gly His Trp Leu
    690                 695                 700

Gly Asp Asn Phe Ala Asp Trp Asp His Tyr Arg Trp Thr Ile Ala Glu
705                 710                 715                 720

Leu Gln Glu Phe Ala Ala Leu Phe Gln Ile Pro Met Val Gly Ser Asp
                725                 730                 735

Ile Cys Gly Tyr Asp Gly Asn Thr Thr Asp Asn Leu Cys Ser Arg Trp
            740                 745                 750

Val Phe Leu Gly Ala Phe Ser Pro Phe Phe Arg Asp His Ser Asp Asn
        755                 760                 765

Gln Ser Pro Pro His Glu Leu Tyr Arg Thr Pro Gln Ile Ala Ala Ala
    770                 775                 780

Ala Arg Ala Ala Ile Asp Ile Arg Tyr Arg Leu Leu Asp Tyr Ala Tyr
785                 790                 795                 800

Thr Val Leu Trp Thr Gln Thr Gln Thr Gly Ala Pro Met Leu Asn Pro
                805                 810                 815

Met Phe Phe Glu Tyr Pro Ala Asp Ser Asn Thr Ala Asp Leu Gln Tyr
            820                 825                 830

Gln Phe Phe Trp Gly Asp Ser Ile Met Val Ala Pro Val Thr Asp Asn
        835                 840                 845

Asp Ser Thr Thr Val Asn Val Tyr Phe Pro Lys Asp Gln Phe Tyr Asp
    850                 855                 860
```

Phe Tyr Thr Gly Ala Pro Val Ser Gly Glu Gly Asn Thr Val Thr Leu
865                 870                 875                 880

Thr Asp Val Gly Phe Asp Thr Ile Pro Leu Tyr Phe Lys Gly Gly Ser
            885                 890                 895

Ile Val Pro Met Arg Val Arg Ser Ala Asn Thr Thr Ala Glu Leu Arg
        900                 905                 910

Gln Gln Asp Phe Val Val Ile Ala Pro Asp Ser His Gly Asp Ala
    915                 920                 925

Thr Gly Gln Leu Tyr Leu Asp Asp Gly Glu Ser Ile Asn Gln Pro His
930                 935                 940

Thr Ser Glu Ile Gln Phe Ser Tyr Arg Gly Gly His Phe Ser Met Thr
945                 950                 955                 960

Gly Lys Phe Asp Tyr Asp Pro Gly Asn Val Val Ile Ser Gln Ile Thr
            965                 970                 975

Leu Leu Gly Ala Asp Gly Ala Gly Lys Gly Gly Ser Tyr Asn Ser Thr
        980                 985                 990

Thr Lys Val Ala Thr Tyr Lys Val  Asn Ala Lys Leu  Thr Gly Lys Phe
        995                 1000                 1005

Glu Ala  Ser Leu His
    1010

<210> SEQ ID NO 5
<211> LENGTH: 3162
<212> TYPE: DNA
<213> ORGANISM: Rasamsonia-composticola

<400> SEQUENCE: 5
atggcaggct ccgccgccct tgttgccagc ctcgtctggc ttgctcaggc cttcgacgct      60
cttgcaggac cggtcagcag tacgactgcc gcagcaccat ctgctcaatt caccgtcccg     120
gccgctgcgg atgttggggc caacttgctt gccaacatcg acgatcccaa tgccgtcaac     180
gcccaggatg tctgtcccgg ttacacggcg tcgaacgtgc agaacaccga gtctgggttt     240
gtggcgaccc tgacgctggc ggggaaacca tgtaatgtgt acggaacgga cgtggagtcc     300
ctgaacctga cggttgagta ccaagctgcg gatcgactga acatcaatat cgtcccgacg     360
cacgtcgatt cttcaaacca gtcgtggtat ctgcttcccg aaaatgtagt gcccaaaccg     420
ggggtcgatg caggagccca agtcccggag agtgatctcg tcttcagctg gtcgaatgaa     480
ccctccttca atttcaaggt gatccggaaa gccacaggcg acattctctt cgacacggag     540
ggttctgtcc tggtgttcga aaaccagttc atcgagtttg cgagcgctct gccgagaac     600
tacaatctct acggtctggg agagcgtatc catggcctgc gactggggaa caacttcacc     660
gccacgacgt atgccgcgga tagcgcagac cctattgacc ggtgagtatc tgagatcgac     720
tgctcagtct gctctgttgg atctgaaaga agttataaaa ctgacctagc tcaggaacat     780
ctacgggacc catcccttt atctggacac ccggtactac gaggttgatt ccgagcatgg     840
gaggttcacg ttggtgacgg acaacgagac cgatttctcc aaggaatatc tgtcgctctc     900
gcatggagtt ttcctgagaa atgcccacgg acaggaggtg ctgctgcgtc ctcagagcat     960
cacctggcgg acactcggtg gcagcattga tctttacttc tacgccggtc cgacccaggc    1020
cgatgttacc cgcagctacc agaccagcac cgttggcctc ccggcaatgc agcagtactt    1080
cacccctggc tatcatcagt gccgctgggg atacagaaac tggtcggagc tagctgatgt    1140
agtggccaat ttcgagaaat tcgagatccc attggaaaat atctggtaag catacgcta    1200
tctgaaagag ttgctgggaa agtgatctga caacttcgtc tctccaggtc ggatattgat    1260

```
tacatgaacg agtaccgcga ctttgagaac gacccggttc gcttctccta cagcgaggga    1320
gccaaattcc tggaccagct ccacaagagt ggccgtcact catatcccgat tgtggacgcc   1380 gcgatctatg acccccaaccc taacaatgac tccgacgcgt aagtctagtc ttgtagggag   1440 gtgatagggga gtggagctga cttctcgatt aggtatgcga catatgatcg aggttctaag   1500
gacgatatct ggttgaagaa tcccgacggc agcgtgtaca tcggagccgt ctggcctggc    1560
tacacagtgt tcaccgattg gcaccatcca aaagccaacg agtggtgggc aaacgagctg    1620
gctctgtggc acgaaaaggt cgcttttgac ggaatctggc tggacatgaa cgaggtctcg    1680
tccttctgcg ttggcagctg tggaacaggg aacctgaccc tgaatcccgt gcacccgaac    1740
ttcgcgctcc cgggagagcc tggagctgtc atctacgact accccgagga cttcaacgtg    1800
acgaatgcca cggcggcggc gtctgcatct gccgcgtcct cgagccaagc tgctgcgaca    1860
gcgacagcta cttcttcgtc cacgactacc agctacctgg tgaccacgcc cactcctgga    1920
gtgcggaatg tcaactaccc tccctatgtg attaatcacg tgcaggaggg tcacgatctc    1980
gctgttcacg ccgtctcgcc caacgcaacc catgtcgatg gtgtgcagga gtacgacgtg    2040
cacaatctct ggggctacca ggagacaaat gcaacctacc atgccctgct gagcatcttc    2100
cccgggaaga gaccgttcat catctcccgt tccacgttcg ccggcagcgg cagatgggcc    2160
ggacactggg gtggcgacaa cgcctcgaaa tgggcgtaca tgttctttc tatcccgcag    2220 gcgctatcgt tctcgctgtt cggcatcccc atgttcggcg tcgacacctg cgggttcaac    2280
ggcaactcgg acgaagagct gtgcaaccgc tggatgcagc tctccgcctt cttcccttc    2340 taccgcaacc acaacgtcct gtcggccatc ccgcaggagc cctatgtctg gcatccgtc    2400 atcgaggcga gcaagtcggc aatgaggatc cgctacaccc tgctccctta cctctacaca    2460
ctgttctacc tcgcccacac cacggggtcg accgtcatgc gtgccttggc gtgggagttc    2520
cccaacgacc cgtccctcgc tgccgtggac cggcagttcc tcctgggccc gtcgctgatg    2580
gtcgtccccg tgctcgagcc gcaggtcgat accgtcaagg gcgtcttccc gggcgttgcc    2640
cagggccaag tctggtacga ctggtacacg cagaccgcgt tcgacgcgca gccaggcgtg    2700
aacacgacca tctccgcgcc gctgggccac atccccgtgt tcgtccgcgg cgggagcgtg    2760
ctccccatgc agcagccggc actggtgacg cgggacgtgc gcaacagccc tggtcgctg    2820 ctggtcgcgc tgggcagcga cggcacggcc tcggacagc tgtacgtgga cgacggcgag    2880
agcatcacac ctccggcgtc cctgcacgtc gacttcgtgg cggccaactt ctcgaccctc    2940
ttcgcgacgc ccgcggtgc gttcaaggac agcaacacgc tggctaacgt cacggtgctg    3000
ggcgtcccag ccgcgccgtc gtctgcagtc acttggaaca acgagacggt tccttcggag    3060
tcggtgtcgt acaatgccac ctccaaagtc ctcgtggtca atggactgca gagtcttacc    3120
cgtgacggag cctggagcag tgactgggtt ctgaagtggt aa                      3162
```

<210> SEQ ID NO 6
<211> LENGTH: 3111
<212> TYPE: DNA
<213> ORGANISM: artificial sequence
<220> FEATURE:
<223> OTHER INFORMATION: CDS-for-predicted-mature-form-of-TauSec099

<400> SEQUENCE: 6

```
ttcgacgctc ttgcaggacc ggtcagcagt acgactgccg cagcaccatc tgctcaattc      60
accgtcccgg ccgctgcgga tgttggggcc aacttgcttg ccaacatcga cgatcccaat     120
```

```
gccgtcaacg cccaggatgt ctgtcccggt tacacggcgt cgaacgtgca gaacaccgag    180
tctgggtttg tggcgaccct gacgctggcg gggaaaccat gtaatgtgta cggaacggac    240
gtggagtccc tgaacctgac ggttgagtac caagctgcgg atcgactgaa catcaatatc    300
gtcccgacgc acgtcgattc ttcaaaccag tcgtggtatc tgcttcccga aaatgtagtg    360
cccaaaccgg gggtcgatgc aggagcccaa gtcccggaga gtgatctcgt cttcagctgg    420
tcgaatgaac cctccttcaa tttcaaggtg atccggaaag ccacaggcga cattctcttc    480
gacacggagg gttctgtcct ggtgttcgaa aaccagttca tcgagtttgc gagcgctctg    540
ccggagaact acaatctcta cggtctggga gagcgtatcc atggcctgcg actggggaac    600
aacttcaccg ccacgacgta tgccgcggat agcgcagacc ctattgaccg gtgagtatct    660
gagatcgact gctcagtctg ctctgttgga tctgaaagaa gttataaaac tgacctagct    720
caggaacatc tacgggaccc atccctttta tctggacacc cggtactacg aggttgattc    780
cgagcatggg aggttcacgt tggtgacgga caacgagacc gatttctcca aggaatatct    840
gtcgctctcg catggagttt tcctgagaaa tgcccacgga caggaggtgc tgctgcgtcc    900
tcagagcatc acctggcgga cactcggtgg cagcattgat ctttacttct acgccggtcc    960
gacccaggcc gatgttaccc gcagctacca gaccagcacc gttggcctcc cggcaatgca   1020
gcagtacttc accctgggct atcatcagtg ccgctgggga tacagaaact ggtcggagct   1080
agctgatgta gtgccaatt tcgagaaatt cgagatccca ttggaaaata tctggtaagg   1140
catacgctat ctgaaagagt tgctgggaaa gtgatctgac aacttcgtct ctccaggtcg   1200
gatattgatt acatgaacga gtaccgcgac tttgagaacg acccggttcg cttctcctac   1260
agcgagggag ccaaattcct ggaccagctc cacaagagtg gccgtcacta catcccgatt   1320
gtggacgccg cgatctatga ccccaaccct aacaatgact ccgacgcgta agtctagtct   1380
tgtagggagg tgatagggag tggagctgac ttctcgatta ggtatgcgac atatgatcga   1440
ggttctaagg acgatatctg gttgaagaat cccgacggca gcgtgtacat cggagccgtc   1500
tggcctggct acacagtgtt caccgattgg caccatccaa aagccaacga gtggtgggca   1560
aacgagctgc tctgtggca cgaaaaggtc gcttttgacg gaatctggct ggacatgaac   1620
gaggtctcgt ccttctgcgt tggcagctgt ggaacaggga acctgaccct gaatcccgtg   1680
cacccgaact tcgcgctccc gggagagcct ggagctgtca tctacgacta ccccgaggac   1740
ttcaacgtga cgaatgccac ggcggcggcg tctgcatctg ccgcgtcctc gagccaagct   1800
gctgcgacag cgacagctac ttcttcgtcc acgactacca gctacctggt gaccacgccc   1860
actcctggag tgcggaatgt caactaccct ccctatgtga ttaatcacgt gcaggagggt   1920
cacgatctcg ctgttcacgc cgtctcgccc aacgcaaccc atgtcgatgg tgtgcaggag   1980
tacgacgtgc acaatctctg gggctaccag gagacaaatg caacctacca tgccctgctg   2040
agcatcttcc ccgggaagag accgttcatc atctcccgtt ccacgttcgc cggcagcggc   2100
agatgggccg gacactgggg tggcgacaac gcctcgaaat gggcgtacat gttctttct   2160 atcccgcagg cgctatcgtt ctcgctgttc ggcatcccca tgttcggcgt cgacacctgc   2220
gggttcaacg gcaactcgga cgaagagctg tgcaaccgct ggatgcagct ctccgccttc   2280 ttcccttct accgcaacca caacgtcctg tcggccatcc cgcaggagcc ctatgtctgg   2340
gcatccgtca tcgaggcgag caagtcggca atgaggatcc gctacaccct gctccttac   2400 ctctacacac tgttctacct cgcccacacc acggggtcga ccgtcatgcg tgccttggcg   2460
tgggagttcc ccaacgaccc gtccctcgct gccgtggacc ggcagttcct cctgggcccg   2520
```

```
tcgctgatgg tcgtccccgt gctcgagccg caggtcgata ccgtcaaggg cgtcttcccg    2580
ggcgttgccc agggccaagt ctggtacgac tggtacacgc agaccgcgtt cgacgcgcag    2640
ccaggcgtga acacgaccat ctccgcgccg ctgggccaca tccccgtgtt cgtccgcggc    2700
gggagcgtgc tccccatgca gcagccggca ctggtgacgc gggacgtgcg caacagcccc    2760
tggtcgctgc tggtcgcgct gggcagcgac ggcacggcct cgggacagct gtacgtggac    2820
gacggcgaga gcatcacacc tccggcgtcc ctgcacgtcg acttcgtggc ggccaacttc    2880
tcgaccctct tcgcgacggc ccgcggtgcg ttcaaggaca gcaacacgct ggctaacgtc    2940
acggtgctgg gcgtcccagc cgcgccgtcg tctgcagtca cttggaacaa cgagacggtt    3000
ccttcggagt cggtgtcgta caatgccacc tccaaagtcc tcgtggtcaa tggactgcag    3060
agtcttaccc gtgacggagc ctggagcagt gactgggttc tgaagtggta a            3111
```

<210> SEQ ID NO 7
<211> LENGTH: 990
<212> TYPE: PRT
<213> ORGANISM: Rasamsonia-composticola

<400> SEQUENCE: 7

```
Met Ala Gly Ser Ala Ala Leu Val Ala Ser Leu Val Trp Leu Ala Gln
1               5                   10                  15

Ala Phe Asp Ala Leu Ala Gly Pro Val Ser Thr Thr Ala Ala Ala
            20                  25                  30

Pro Ser Ala Gln Phe Thr Val Pro Ala Ala Asp Val Gly Ala Asn
        35                  40                  45

Leu Leu Ala Asn Ile Asp Asp Pro Asn Ala Val Asn Ala Gln Asp Val
50                  55                  60

Cys Pro Gly Tyr Thr Ala Ser Asn Val Gln Asn Thr Glu Ser Gly Phe
65                  70                  75                  80

Val Ala Thr Leu Thr Leu Ala Gly Lys Pro Cys Asn Val Tyr Gly Thr
                85                  90                  95

Asp Val Glu Ser Leu Asn Leu Thr Val Glu Tyr Gln Ala Ala Asp Arg
            100                 105                 110

Leu Asn Ile Asn Ile Val Pro Thr His Val Asp Ser Ser Asn Gln Ser
        115                 120                 125

Trp Tyr Leu Leu Pro Glu Asn Val Val Pro Lys Pro Gly Val Asp Ala
    130                 135                 140

Gly Ala Gln Val Pro Glu Ser Asp Leu Val Phe Ser Trp Ser Asn Glu
145                 150                 155                 160

Pro Ser Phe Asn Phe Lys Val Ile Arg Lys Ala Thr Gly Asp Ile Leu
                165                 170                 175

Phe Asp Thr Glu Gly Ser Val Leu Val Phe Glu Asn Gln Phe Ile Glu
            180                 185                 190

Phe Ala Ser Ala Leu Pro Glu Asn Tyr Asn Leu Tyr Gly Leu Gly Glu
        195                 200                 205

Arg Ile His Gly Leu Arg Leu Gly Asn Asn Phe Thr Ala Thr Thr Tyr
    210                 215                 220

Ala Ala Asp Ser Ala Asp Pro Ile Asp Arg Asn Ile Tyr Gly Thr His
225                 230                 235                 240

Pro Phe Tyr Leu Asp Thr Arg Tyr Tyr Glu Val Asp Ser Glu His Gly
                245                 250                 255

Arg Phe Thr Leu Val Thr Asp Asn Glu Thr Asp Phe Ser Lys Glu Tyr
            260                 265                 270
```

-continued

```
Leu Ser Leu Ser His Gly Val Phe Leu Arg Asn Ala His Gly Gln Glu
        275                 280                 285

Val Leu Leu Arg Pro Gln Ser Ile Thr Trp Arg Thr Leu Gly Gly Ser
    290                 295                 300

Ile Asp Leu Tyr Phe Tyr Ala Gly Pro Thr Gln Ala Asp Val Thr Arg
305                 310                 315                 320

Ser Tyr Gln Thr Ser Thr Val Gly Leu Pro Ala Met Gln Gln Tyr Phe
                325                 330                 335

Thr Leu Gly Tyr His Gln Cys Arg Trp Gly Tyr Arg Asn Trp Ser Glu
                340                 345                 350

Leu Ala Asp Val Val Ala Asn Phe Glu Lys Phe Glu Ile Pro Leu Glu
            355                 360                 365

Asn Ile Trp Ser Asp Ile Asp Tyr Met Asn Glu Tyr Arg Asp Phe Glu
        370                 375                 380

Asn Asp Pro Val Arg Phe Ser Tyr Ser Glu Gly Ala Lys Phe Leu Asp
385                 390                 395                 400

Gln Leu His Lys Ser Gly Arg His Tyr Ile Pro Ile Val Asp Ala Ala
                405                 410                 415

Ile Tyr Asp Pro Asn Pro Asn Asn Asp Ser Asp Ala Tyr Ala Thr Tyr
            420                 425                 430

Asp Arg Gly Ser Lys Asp Asp Ile Trp Leu Lys Asn Pro Asp Gly Ser
        435                 440                 445

Val Tyr Ile Gly Ala Val Trp Pro Gly Tyr Thr Val Phe Thr Asp Trp
    450                 455                 460

His His Pro Lys Ala Asn Glu Trp Trp Ala Asn Glu Leu Ala Leu Trp
465                 470                 475                 480

His Glu Lys Val Ala Phe Asp Gly Ile Trp Leu Asp Met Asn Glu Val
                485                 490                 495

Ser Ser Phe Cys Val Gly Ser Cys Gly Thr Gly Asn Leu Thr Leu Asn
                500                 505                 510

Pro Val His Pro Asn Phe Ala Leu Pro Gly Glu Pro Gly Ala Val Ile
            515                 520                 525

Tyr Asp Tyr Pro Glu Asp Phe Asn Val Thr Asn Ala Thr Ala Ala Ala
        530                 535                 540

Ser Ala Ser Ala Ala Ser Ser Ser Gln Ala Ala Ala Thr Ala Thr Ala
545                 550                 555                 560

Thr Ser Ser Ser Thr Thr Thr Ser Tyr Leu Val Thr Thr Pro Thr Pro
                565                 570                 575

Gly Val Arg Asn Val Asn Tyr Pro Pro Tyr Val Ile Asn His Val Gln
                580                 585                 590

Glu Gly His Asp Leu Ala Val His Ala Val Ser Pro Asn Ala Thr His
            595                 600                 605

Val Asp Gly Val Gln Glu Tyr Asp Val His Asn Leu Trp Gly Tyr Gln
610                 615                 620

Glu Thr Asn Ala Thr Tyr His Ala Leu Leu Ser Ile Phe Pro Gly Lys
625                 630                 635                 640

Arg Pro Phe Ile Ile Ser Arg Ser Thr Phe Ala Gly Ser Gly Arg Trp
                645                 650                 655

Ala Gly His Trp Gly Gly Asp Asn Ala Ser Lys Trp Ala Tyr Met Phe
                660                 665                 670

Phe Ser Ile Pro Gln Ala Leu Ser Phe Ser Leu Phe Gly Ile Pro Met
            675                 680                 685
```

Phe Gly Val Asp Thr Cys Gly Phe Asn Gly Asn Ser Asp Glu Glu Leu
690                 695                 700

Cys Asn Arg Trp Met Gln Leu Ser Ala Phe Pro Phe Tyr Arg Asn
705                 710                 715                 720

His Asn Val Leu Ser Ala Ile Pro Gln Glu Pro Tyr Val Trp Ala Ser
            725                 730                 735

Val Ile Glu Ala Ser Lys Ser Ala Met Arg Ile Arg Tyr Thr Leu Leu
            740                 745                 750

Pro Tyr Leu Tyr Thr Leu Phe Tyr Leu Ala His Thr Thr Gly Ser Thr
            755                 760                 765

Val Met Arg Ala Leu Ala Trp Glu Phe Pro Asn Asp Pro Ser Leu Ala
770                 775                 780

Ala Val Asp Arg Gln Phe Leu Leu Gly Pro Ser Leu Met Val Val Pro
785                 790                 795                 800

Val Leu Glu Pro Gln Val Asp Thr Val Lys Gly Val Phe Pro Gly Val
                805                 810                 815

Ala Gln Gly Gln Val Trp Tyr Asp Trp Tyr Thr Gln Thr Ala Phe Asp
            820                 825                 830

Ala Gln Pro Gly Val Asn Thr Thr Ile Ser Ala Pro Leu Gly His Ile
            835                 840                 845

Pro Val Phe Val Arg Gly Gly Ser Val Leu Pro Met Gln Gln Pro Ala
850                 855                 860

Leu Val Thr Arg Asp Val Arg Asn Ser Pro Trp Ser Leu Leu Val Ala
865                 870                 875                 880

Leu Gly Ser Asp Gly Thr Ala Ser Gly Gln Leu Tyr Val Asp Asp Gly
                885                 890                 895

Glu Ser Ile Thr Pro Pro Ala Ser Leu His Val Asp Phe Val Ala Ala
            900                 905                 910

Asn Phe Ser Thr Leu Phe Ala Thr Ala Arg Gly Ala Phe Lys Asp Ser
            915                 920                 925

Asn Thr Leu Ala Asn Val Thr Val Leu Gly Val Pro Ala Ala Pro Ser
            930                 935                 940

Ser Ala Val Thr Trp Asn Asn Glu Thr Val Pro Ser Glu Ser Val Ser
945                 950                 955                 960

Tyr Asn Ala Thr Ser Lys Val Leu Val Asn Gly Leu Gln Ser Leu
                965                 970                 975

Thr Arg Asp Gly Ala Trp Ser Ser Asp Trp Val Leu Lys Trp
            980                 985                 990

<210> SEQ ID NO 8
<211> LENGTH: 973
<212> TYPE: PRT
<213> ORGANISM: artificial sequence
<220> FEATURE:
<223> OTHER INFORMATION: Predicted-mature-TauSec099

<400> SEQUENCE: 8

Phe Asp Ala Leu Ala Gly Pro Val Ser Ser Thr Thr Ala Ala Pro
1               5                   10                  15

Ser Ala Gln Phe Thr Val Pro Ala Ala Ala Asp Val Gly Ala Asn Leu
            20                  25                  30

Leu Ala Asn Ile Asp Asp Pro Asn Ala Val Asn Ala Gln Asp Val Cys
        35                  40                  45

Pro Gly Tyr Thr Ala Ser Asn Val Gln Asn Thr Glu Ser Gly Phe Val
    50                  55                  60

```
Ala Thr Leu Thr Leu Ala Gly Lys Pro Cys Asn Val Tyr Gly Thr Asp
 65                  70                  75                  80

Val Glu Ser Leu Asn Leu Thr Val Glu Tyr Gln Ala Ala Asp Arg Leu
                 85                  90                  95

Asn Ile Asn Ile Val Pro Thr His Val Asp Ser Ser Asn Gln Ser Trp
            100                 105                 110

Tyr Leu Leu Pro Glu Asn Val Val Pro Lys Pro Gly Val Asp Ala Gly
        115                 120                 125

Ala Gln Val Pro Glu Ser Asp Leu Val Phe Ser Trp Ser Asn Glu Pro
    130                 135                 140

Ser Phe Asn Phe Lys Val Ile Arg Lys Ala Thr Gly Asp Ile Leu Phe
145                 150                 155                 160

Asp Thr Glu Gly Ser Val Leu Val Phe Glu Asn Gln Phe Ile Glu Phe
                165                 170                 175

Ala Ser Ala Leu Pro Glu Asn Tyr Asn Leu Tyr Gly Leu Gly Glu Arg
            180                 185                 190

Ile His Gly Leu Arg Leu Gly Asn Asn Phe Thr Ala Thr Thr Tyr Ala
        195                 200                 205

Ala Asp Ser Ala Asp Pro Ile Asp Arg Asn Ile Tyr Gly Thr His Pro
    210                 215                 220

Phe Tyr Leu Asp Thr Arg Tyr Tyr Glu Val Asp Ser Glu His Gly Arg
225                 230                 235                 240

Phe Thr Leu Val Thr Asp Asn Glu Thr Asp Phe Ser Lys Glu Tyr Leu
                245                 250                 255

Ser Leu Ser His Gly Val Phe Leu Arg Asn Ala His Gly Gln Glu Val
            260                 265                 270

Leu Leu Arg Pro Gln Ser Ile Thr Trp Arg Thr Leu Gly Gly Ser Ile
        275                 280                 285

Asp Leu Tyr Phe Tyr Ala Gly Pro Thr Gln Ala Asp Val Thr Arg Ser
    290                 295                 300

Tyr Gln Thr Ser Thr Val Gly Leu Pro Ala Met Gln Gln Tyr Phe Thr
305                 310                 315                 320

Leu Gly Tyr His Gln Cys Arg Trp Gly Tyr Arg Asn Trp Ser Glu Leu
                325                 330                 335

Ala Asp Val Val Ala Asn Phe Glu Lys Phe Glu Ile Pro Leu Glu Asn
            340                 345                 350

Ile Trp Ser Asp Ile Asp Tyr Met Asn Glu Tyr Arg Asp Phe Glu Asn
        355                 360                 365

Asp Pro Val Arg Phe Ser Tyr Ser Glu Gly Ala Lys Phe Leu Asp Gln
    370                 375                 380

Leu His Lys Ser Gly Arg His Tyr Ile Pro Ile Val Asp Ala Ala Ile
385                 390                 395                 400

Tyr Asp Pro Asn Pro Asn Asn Asp Ser Asp Ala Tyr Ala Thr Tyr Asp
                405                 410                 415

Arg Gly Ser Lys Asp Asp Ile Trp Leu Lys Asn Pro Asp Gly Ser Val
            420                 425                 430

Tyr Ile Gly Ala Val Trp Pro Gly Tyr Thr Val Phe Thr Asp Trp His
        435                 440                 445

His Pro Lys Ala Asn Glu Trp Trp Ala Asn Glu Leu Ala Leu Trp His
    450                 455                 460

Glu Lys Val Ala Phe Asp Gly Ile Trp Leu Asp Met Asn Glu Val Ser
465                 470                 475                 480

Ser Phe Cys Val Gly Ser Cys Gly Thr Gly Asn Leu Thr Leu Asn Pro
```

485                 490                 495
Val His Pro Asn Phe Ala Leu Pro Gly Glu Pro Gly Ala Val Ile Tyr
                500                 505                 510

Asp Tyr Pro Glu Asp Phe Asn Val Thr Asn Ala Thr Ala Ala Ala Ser
                515                 520                 525

Ala Ser Ala Ala Ser Ser Gln Ala Ala Thr Ala Thr Ala Thr
            530                 535                 540

Ser Ser Ser Thr Thr Thr Ser Tyr Leu Val Thr Thr Pro Thr Pro Gly
545                 550                 555                 560

Val Arg Asn Val Asn Tyr Pro Pro Tyr Val Ile Asn His Val Gln Glu
                565                 570                 575

Gly His Asp Leu Ala Val His Ala Val Ser Pro Asn Ala Thr His Val
                580                 585                 590

Asp Gly Val Gln Glu Tyr Asp Val His Asn Leu Trp Gly Tyr Gln Glu
                595                 600                 605

Thr Asn Ala Thr Tyr His Ala Leu Leu Ser Ile Phe Pro Gly Lys Arg
                610                 615                 620

Pro Phe Ile Ile Ser Arg Ser Thr Phe Ala Gly Ser Gly Arg Trp Ala
625                 630                 635                 640

Gly His Trp Gly Gly Asp Asn Ala Ser Lys Trp Ala Tyr Met Phe Phe
                645                 650                 655

Ser Ile Pro Gln Ala Leu Ser Phe Ser Leu Phe Gly Ile Pro Met Phe
                660                 665                 670

Gly Val Asp Thr Cys Gly Phe Asn Gly Asn Ser Asp Glu Glu Leu Cys
                675                 680                 685

Asn Arg Trp Met Gln Leu Ser Ala Phe Phe Pro Phe Tyr Arg Asn His
                690                 695                 700

Asn Val Leu Ser Ala Ile Pro Gln Glu Pro Tyr Val Trp Ala Ser Val
705                 710                 715                 720

Ile Glu Ala Ser Lys Ser Ala Met Arg Ile Arg Tyr Thr Leu Leu Pro
                725                 730                 735

Tyr Leu Tyr Thr Leu Phe Tyr Leu Ala His Thr Thr Gly Ser Thr Val
                740                 745                 750

Met Arg Ala Leu Ala Trp Glu Phe Pro Asn Asp Pro Ser Leu Ala Ala
                755                 760                 765

Val Asp Arg Gln Phe Leu Leu Gly Pro Ser Leu Met Val Val Pro Val
                770                 775                 780

Leu Glu Pro Gln Val Asp Thr Val Lys Gly Val Phe Pro Gly Val Ala
785                 790                 795                 800

Gln Gly Gln Val Trp Tyr Asp Trp Tyr Thr Gln Thr Ala Phe Asp Ala
                805                 810                 815

Gln Pro Gly Val Asn Thr Thr Ile Ser Ala Pro Leu Gly His Ile Pro
                820                 825                 830

Val Phe Val Arg Gly Gly Ser Val Leu Pro Met Gln Gln Pro Ala Leu
                835                 840                 845

Val Thr Arg Asp Val Arg Asn Ser Pro Trp Ser Leu Leu Val Ala Leu
                850                 855                 860

Gly Ser Asp Gly Thr Ala Ser Gly Gln Leu Tyr Val Asp Asp Gly Glu
865                 870                 875                 880

Ser Ile Thr Pro Pro Ala Ser Leu His Val Asp Phe Val Ala Ala Asn
                885                 890                 895

Phe Ser Thr Leu Phe Ala Thr Ala Arg Gly Ala Phe Lys Asp Ser Asn
                900                 905                 910

-continued

```
Thr Leu Ala Asn Val Thr Val Leu Gly Val Pro Ala Ala Pro Ser Ser
            915                 920                 925

Ala Val Thr Trp Asn Asn Glu Thr Val Pro Ser Glu Ser Val Ser Tyr
        930                 935                 940

Asn Ala Thr Ser Lys Val Leu Val Val Asn Gly Leu Gln Ser Leu Thr
945                 950                 955                 960

Arg Asp Gly Ala Trp Ser Ser Asp Trp Val Leu Lys Trp
                965                 970
```

ALPHA-GLUCOSIDASE, COMPOSITIONS AND METHODS

CROSS REFERENCE TO RELATED APPLICATION

This application is the National Stage application of International Application No. PCT/US2016/019649 (filed Feb. 25, 2016), which claims the benefit of priority from International Application No. PCT/CN2015/073269 (filed Feb. 25, 2015). Both of these prior applications are incorporated by reference in their entirety.

FIELD OF THE INVENTION

The present disclosure relates to engineered compositions comprising certain polypeptides isolated, derived or derivable (synthetic or engineered) from *Rasamsonia*, or from homologs of *Rasamsonia*, which have alpha-glucosidase activity. The present disclosure further relates to polynucleotides encoding such polypeptides, engineered nucleic acid constructs, vectors, host cells and mutant cells comprising genes encoding such polypeptides, which may also enable the production of such polypeptides. The disclosure additionally relates to compositions comprising such alpha-glucosidase polypeptides, or having alpha-glucosidase activities. Moreover, the disclosure relates to methods of recombinantly producing such polypeptides or such compositions, as well as methods of using or applying the polypeptides or compositions thus produced in industrial settings.

BACKGROUND

Starch is made up of a mixture of amylose (15-30% w/w) and amylopectin (70-85% w/w). The amylose part consists of linear chains of alpha-1,4-linked glucose units having a molecular weight (MW) ranging from about 60,000 to about 800,000. The amylopectin part is a branched polymer containing alpha-1,6 branch points every 24-30 glucose units; its MW may be as high as 100 million.

A number of enzymes are involved in the degradation of starch, including, for example, alpha-amylases, beta-amylases, amyloglucosidases, pullulanases, isoamylases, alpha-glucosidases, cyclodextrin glycosyltransferases and the like.

As a class, alpha-glucosidases (EC 3.2.1.20) are capable of catalyzing the liberation of glucose from non-reducing ends of alpha-glucosides, alpha-linked oligosaccharides, and/or alpha-glucans. These enzymes show diverse substrate specificities, however; some prefer alpha-linked di-, oligo-, and/or polyglucans, while others preferentially hydrolyze heterogeneous substrates such as aryl glucosides and sucrose. See, Chiba, S. (1988) Alpha-Glucosidases, pp. 104-105. The Amylase Research Society of Japan (ed.), Handbook of Amylases and Related Enzymes. Pergamon Press, Oxford, United Kingdom.

Alpha-glucosidase is a retaining glycosyl hydrolase (GH), capable of catalyzing transglycosylation. See, Chiba, S. (1997) Biosci. Biotechnol. Biochem. 61:1233-1239. For example, buckwheat alpha-glucosidase hydrolyzes soluble starch to produce kojibiose (2-O-alpha-glucosyl-glucose), nigerose (3-O-alpha-glucosyl-glucose), maltose, and/or isomaltose. See, Chiba, S. (1988), supra. Alpha-glucosidases from *Bacillus stearothermophilus* and brewer's yeast, on the other hand, hydrolyzes starch to produce oligosaccharides consisting of alpha-1,3, alpha-1,4, and/or alpha-1,6 linkages. See, Mala S., et al., (1999) Carbohydr. Res. 322:209-218.

Alpha-glucosidases are often used in conjunction with other starch-degrading enzymes, including, for example, alpha-amylase, glucoamylases, and the like, to drive more complete hydrolysis of starchy substrates into soluble fermentable sugars, which are useful for various downstream industrial applications. Depending on the industrial applications, alpha glucosidases or other enzymes suitable for these industrial processes can be diverse. There is as such always a need in the art for alternative alpha-glucosidases with improved or different properties such as pH optimum, temperature optimum, substrate specificities, and/or thermostability.

It is an object of the present disclosure to provide certain polypeptides having alpha-glucosidase activity, polynucleotides encoding the polypeptides, nucleic acid constructs that can be used to produce such polypeptides, compositions comprising thereof, as well as methods of making and using such polypeptides.

SUMMARY

The present disclosure relates to certain polypeptides having alpha-glucosidase activity derived or derivable (synthetic or engineered) from *Rasamsonia* having alpha-glucosidase activity, or polypeptides that are isolated *Rasamsonia* homologs, polynucleotides encoding such polypeptides, as well as to compositions comprising such polypeptides, methods of producing or using such polypeptides or compositions. The disclosure also pertains to certain nucleic acid constructs, vectors, host cells, or mutant cells comprising the polynucleotides, which are useful for producing such polypeptides.

In a first aspect, the disclosure provides a polypeptide having alpha-glucosidase activity comprising an amino acid sequence that is at least about 80% identical to that of SEQ ID NO:3 or 7. In some embodiments, the polypeptide having alpha-glucosidase activity of the first aspect comprises an amino acid sequence that is at least about 90% identical to that of SEQ ID NO: 3 or 7. In further embodiments, the polypeptide having alpha-glucosidase activity of this aspect comprises an amino acid sequence that is at least about 95% identical to that of SEQ ID NO:3 or 7.

In a second aspect, the disclosure provides a composition comprising a polypeptide having alpha-glucosidase activity, which polypeptide comprises an amino acid sequence that is at least about 80% identical, at least about 90%, at least about 95% identical to that of SEQ ID NO:3 or 7, and at least one or more of an alpha-amylase, a beta-amylase, a glucoamylase (amyloglucosidase), a pullulanase, an isoamylase, a different alpha glucosidase, and/or a cyclodextrin glycosyltransferase.

In some embodiments, the composition of the second aspect is one wherein the polypeptide having alpha-glucosidase activity, which polypeptide comprises an amino acid sequence that is at least about 80% identical, at least about 90%, at least about 95% identical to that of SEQ ID NO:3 or 7, is derived from a different microorganism as the an alpha-amylase, a beta-amylase, a glucoamylase (amyloglucosidase), a pullulanase, an isoamylase, a different alpha glucosidase, or a cyclodextrin glycosyltransferase in the composition.

In further embodiments, the composition of the second aspect is one prepared by admixing the polypeptide having alpha-glucosidase activity, which polypeptide comprises an amino acid sequence that is at least about 80% identical, at least about 90%, at least about 95% identical to that of SEQ ID NO:3 or 7 expressed by a host organism with the alpha-amylase, beta-amylase, glucoamylase (amyloglucosidase), pullulanase, isoamylase, different alpha glucosidase, or the cyclodextrin glycosyltransferase expressed by a second, different host organism.

In alternative embodiments, the composition of the second aspect is one prepared by co-expressing the polypeptide having alpha-glucosidase activity, which polypeptide comprises an amino acid sequence that is at least about 80% identical, at least about 90%, at least about 95% identical to that of SEQ ID NO:3 or 7 and the alpha-amylase, beta-amylase, glucoamylase (amyloglucosidase), pullulanase, isoamylase, different alpha glucosidase, or the cylodextrin glycosyltransferase in a same host microorganism In a third aspect, the disclosure provides a polynucleotide encoding the polypeptide of the first aspect.

In some embodiments, the polypeptide of the third aspect is one comprising a polynucleotide sequence that is at least about 85%, at least about 90%, at least about 95% identical to that of SEQ ID NO:2 or 6, together with at least one transcriptional or translational regulatory sequence that allows the polynucleotide sequence to be expressed by a host cell.

In some embodiments, the polynucleotide of this aspect is one wherein the transcriptional or translational regulatory sequence is one that is heterologous to the microorganism from which the polynucleotide sequence is derived.

In a fourth aspect, the disclosure provides a vector comprising the polynucleotide of the third aspect.

In a fifth aspect, the disclosure provides a host cell comprising the vector of the fourth aspect.

In some embodiments, the host cell of the fifth aspect is a *Trichoderma* or *Aspergillus* fungal host cell. Alternatively, the host cell of the fifth aspect is an *E. coli, Bacillus, Streptomyces*, or *Pseudomonas* cell In a sixth aspect, the disclosure provides a method of making the polypeptide of the first aspect, or the composition of the second aspect, comprising cultivating the host cell of the fifth aspect.

In some embodiments, the method of the sixth aspect further comprises a step during which the polypeptide is recovered, enriched and/or purified In a seventh aspect, the disclosure provides a method of applying the polypeptide of the first aspect, or the composition of the second aspect in grain and starch processing, or food and beverage applications.

BRIEF DESCRIPTION OF THE DRAWINGS

FIG. 1. Plasmid map of pGX256-TauSec098
FIG. 2. Plasmid map of pGX256-TauSec099

DETAILED DESCRIPTION

I. Overview

The present disclosure relates to certain polypeptides having alpha-glucosidase activity isolated, derived or derivable, either synthetically or using recombinant means, from *Rasamsonia*, or certain polypeptides isolated, derived or derivable from *Rasamsonia* homologs having alpha-glucosidase activity. The present disclosure further relates to certain polynucleotides encoding such polypeptides, nucleic constructs, vectors, host cells or mutant cells comprising such polynucleotides that can be useful for allowing such polypeptides to be produced in a recombinant fashion, in sufficiently large amounts for industrial applications. Furthermore, the present disclosure relates to certain compositions comprising such polypeptides, as well as methods of preparing such compositions and applying such compositions or polypeptides in industrial settings.

II. Abbreviations and Acronyms

The following abbreviations/acronyms have the following meanings unless otherwise specified:
cDNA complementary DNA
DNA deoxyribonucleic acid
EDTA ethylenediaminetetraacetic acid
kDa kiloDalton
MW molecular weight
PEG polyethyleneglycol
ppm parts per million, e.g., μg protein per gram dry solid
RNA ribonucleic acid
SDS-PAGE sodium dodecyl sulfate polyacrylamide gel electrophoresis
sp. species
Tm melting temperature
w/v weight/volume
w/w weight/weight
° C. degrees Centigrade
$H_2O$ water
g or gm grams
μg micrograms
mg milligrams
kg kilograms
μL and μl microliters
mL and ml milliliters
mm millimeters
μm micrometer
M molar
mM millimolar
μM micromolar
U units
sec seconds
min(s) minute/minutes
hr(s) hour/hours
Tris-HCl tris(hydroxymethyl)aminomethane hydrochloride
HEPES 4-(2-hydroxyethyl)-1-piperazineethanesulfonic acid
CV column volumes III. Definitions Prior to describing the present compositions and methods, the following terms and phrases are defined. Terms not defined should be accorded their ordinary meaning as used in the art.

Where a range of values is provided, it is understood that each intervening value, to the tenth of the unit of the lower limit unless the context clearly dictates otherwise, between the upper and lower limit of that range and any other stated or intervening value in that stated range, is encompassed within the present compositions and methods. The upper and lower limits of these smaller ranges may independently be included in the smaller ranges and are also encompassed within the present compositions and methods, subject to any specifically excluded limit in the stated range. Where the stated range includes one or both of the limits, ranges excluding either or both of those included limits are also included in the present compositions and methods.

Certain ranges are presented herein with numerical values being preceded by the term "about." The term "about" is used herein to provide literal support for the exact number that it precedes, as well as a number that is near to or approximately the number that the term precedes. In determining whether a number is near to or approximately a specifically recited number, the near or approximating unrecited number may be a number which, in the context in which it is presented, provides the substantial equivalent of the specifically recited number. For example, in connection with a numerical value, the term "about" refers to a range of −10% to +10% of the numerical value, unless the term is otherwise specifically defined in context. In another example, the phrase a "pH value of about 6" refers to pH values of from 5.4 to 6.6, unless the pH value is specifically defined otherwise.

The headings provided herein are not limitations of the various aspects or embodiments of the present compositions and methods which can be had by reference to the specification as a whole. Accordingly, the terms defined immediately below are more fully defined by reference to the specification as a whole.

The present document is organized into a number of sections for ease of reading; however, the reader will appreciate that statements made in one section may apply to other sections. In this manner, the headings used for different sections of the disclosure should not be construed as limiting.

Unless defined otherwise, all technical and scientific terms used herein have the same meaning as commonly understood by one of ordinary skill in the art to which the present compositions and methods belongs. Although any methods and materials similar or equivalent to those described herein can also be used in the practice or testing of the present compositions and methods, representative illustrative methods and materials are now described.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present compositions and methods are not entitled to antedate such publication by virtue of prior disclosure. Further, the dates of publication provided may be different from the actual publication dates which may need to be independently confirmed.

In accordance with this detailed description, the following abbreviations and definitions apply. Note that the singular forms "a," "an," and "the" include plural referents unless the context clearly dictates otherwise. Thus, for example, reference to "an enzyme" includes a plurality of such enzymes, and reference to "the dosage" includes reference to one or more dosages and equivalents thereof known to those skilled in the art, and so forth.

It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

It is further noted that the term "consisting essentially of," as used herein refers to a composition wherein the component(s) after the term is in the presence of other known component(s) in a total amount that is less than 30% by weight of the total composition and do not contribute to or interferes with the actions or activities of the component(s).

It is further noted that the term "comprising," as used herein, means including, but not limited to, the component(s) after the term "comprising." The component(s) after the term "comprising" are required or mandatory, but the composition comprising the component(s) may further include other non-mandatory or optional component(s).

It is also noted that the term "consisting of," as used herein, means including, and limited to, the component(s) after the term "consisting of." The component(s) after the term "consisting of" are therefore required or mandatory, and no other component(s) are present in the composition.

As will be apparent to those of skill in the art upon reading this disclosure, each of the individual embodiments described and illustrated herein has discrete components and features which may be readily separated from or combined with the features of any of the other several embodiments without departing from the scope or spirit of the present compositions and methods described herein. Any recited method can be carried out in the order of events recited or in any other order which is logically possible.

As used herein, the term "alpha-glucosidase activity" refers to an alpha-D-glucoside glucohydrolase activity (E.C. 3.2.1.20), which catalyzes the exohydrolysis of terminal, non-reducing 1,4-linked, alpha-D-glucose residues resulting in the release of alpha-D-glucose. Natural substrates of the alpha-glucosidase enzyme activity include, for example, maltose, maltotriose, maltotetraose, maltopentaose, starch (soluble), amylose, amylopectin, isomaltose, Kojibiose, sucrose, nigerose, turanose, melizitose, glycogen, and the like.

As used herein, the term "gene" means the segment of DNA involved in producing a polypeptide, that may or may not include regions preceding and following the coding region, e.g. 5' untranslated (51 UTR) or "leader" sequences and 3' UTR or "trailer" sequences, as well as intervening sequences (introns) between individual coding segments (exons). A gene may refer to one that is naturally occurring, or a mutant gene, or a synthetic gene.

As used herein, the term "% identity" is used interchangeably with the term "% homology" and refers to the level of nucleic acid or amino acid sequence identity between the nucleic acid sequences that encode any one of the inventive polypeptides or the inventive polypeptide's amino acid sequences, when aligned using a sequence alignment program.

As used herein, the term "vector" refers to a nucleic acid construct designed for transfer between different host cells.

As used herein, the term "expression vector" refers to a DNA construct comprising a DNA sequence encoding a polypeptide of interest, which coding sequence is operably linked to a suitable control sequence capable of effecting expression of the DNA in a suitable host. Such control sequences may include a promoter to effect transcription, an optional operator sequence to control transcription, a sequence encoding suitable ribosome binding sites on the mRNA, enhancers and sequences which control termination of transcription and translation.

As used herein, the term "plasmid" refers to a circular double-stranded (ds) DNA construct used as a cloning vector, and which forms an extra chromosomal self-replicating genetic element in many bacteria and some eukaryotes.

As used herein, the term "selectable marker-encoding nucleotide sequence" refers to a nucleotide sequence which is capable of expression in cells and where expression of the selectable marker confers to cells containing the expressed gene the ability to grow in the presence of a corresponding selective agent, or under corresponding selective growth conditions.

As used herein, the term "promoter" refers to a nucleic acid sequence that functions to direct transcription of a downstream gene. The promoter will generally be appropriate to the host cell in which the target gene is being expressed. The promoter, together with other transcriptional and translational regulatory nucleic acid sequences (also termed "control sequences"), are often used to express a given gene. In general, the transcriptional and translational regulatory sequences include, but are not limited to, promoter sequences, ribosomal binding sites, transcriptional start and stop sequences, translational start and stop sequences, and enhancer or activator sequences.

As used herein, the term "control sequences" is defined herein to include all components, which are necessary or advantageous for the expression of a polynucleotide encoding a polypeptide of the present disclosure. Each control sequence may be native or foreign to the nucleotide sequence encoding the polypeptide or native or foreign to each other. Such control sequences include, but are not limited to, a leader, polyadenylation sequence, propeptide sequence, promoter, signal peptide sequence, and transcription terminator. At a minimum, the control sequences include a promoter, and transcriptional and translational stop signals. The control sequences may be provided with linkers for the purpose of introducing specific restriction sites facilitating ligation of the control sequences with the coding region of the nucleotide sequence encoding a polypeptide.

As used herein, the term "operably linked" denotes herein a configuration in which a control sequence is placed at an appropriate position relative to the coding sequence of the polynucleotide sequence such that the control sequence directs the expression of the coding sequence of a polypeptide.

As used herein, the term "signal sequence" is a sequence of amino acids attached to the N-terminal portion of a protein, which facilitates the secretion of the protein outside the cell. The mature form of an extracellular protein lacks the signal sequence, which is cleaved off during the secretion process.

As used herein, the term "coding sequence" means a nucleotide sequence, which directly specifies the amino acid sequence of its protein product. The boundaries of the coding sequence are generally determined by an open reading frame, which usually begins with the ATG start codon or alternative start codons such as GTG and TTG and ends with a stop codon such as TAA, TAG and TGA. The coding sequence may be a DNA, cDNA, or recombinant nucleotide sequence.

As used herein, the terms "polypeptide" and "protein" are used interchangeably to refer to polymers of any length comprising amino acid residues linked by peptide bonds. The conventional one-letter or three-letter codes for amino acid residues are used herein. The polymer may be linear or branched, it may comprise modified amino acids, and it may be interrupted by non-amino acids. The terms also encompass an amino acid polymer that has been modified naturally or by intervention; for example, disulfide bond formation, glycosylation, lipidation, acetylation, phosphorylation, or any other manipulation or modification, such as conjugation with a labeling component. Also included within the definition are, for example, polypeptides containing one or more analogs of an amino acid (including, for example, unnatural amino acids, etc.), as well as other modifications known in the art.

As used herein, the terms "polypeptide fragment" is defined herein as a polypeptide having one or more amino acids deleted from the amino and/or carboxyl terminus of an amino acid sequence or a homologue thereof, wherein the fragment has alpha-glucosidase activity. For example, in one embodiment, a suitable fragment of the invention may be one that comprises at least 650 contiguous amino acid residues, at least contiguous 700 amino acid residues, at least contiguous 750 amino acid residues, at least 800 contiguous amino acid residues, at least 850 contiguous amino acid residues, at least 900 contiguous amino acid residues, or even at least contiguous 950 amino acid residues of SEQ ID NO:3, or of a homologous sequence that is at least about 70% identical to SEQ ID NO:3. Alternatively, in another embodiment, a suitable fragment of the invention may be one that comprises at least 650 contiguous amino acid residues, at least contiguous 700 amino acid residues, at least contiguous 750 amino acid residues, at least 800 contiguous amino acid residues, at least 850 contiguous amino acid residues, at least 900 contiguous amino acid residues, or even at least contiguous 950 amino acid residues of SEQ ID NO:3, or of a homologous sequence that is at least about 70% identical to SEQ ID NO:7.

As used herein, the term "recombinant", when used in reference to a subject cell, nucleic acid, polypeptides/enzymes or vector, indicates that the subject has been modified from its native state. Thus, for example, recombinant cells express genes that are not found within the native (non-recombinant) form of the cell, or express native genes at different levels or under different conditions than found in nature. Recombinant nucleic acids may differ from a native sequence by one or more nucleotides and/or are operably linked to heterologous sequences, e.g., a heterologous promoter, signal sequences that allow secretion, etc., in an expression vector. Recombinant polypeptides/enzymes may differ from a native sequence by one or more amino acids and/or are fused with heterologous sequences. A vector comprising a nucleic acid encoding a protein of interest is, for example, a recombinant vector.

As used herein, "Ascomycete fungal strain", refers to any organism in the Division Ascomycota in the Kingdom Fungi. Exemplary Ascomycetes fungal cells include but are not limited to filamentous fungi in the subphylum Pezizomycotina, such as *Trichoderma* spp, *Aspergillus* spp, and *Penicillium* spp.

As used herein, the "filamentous fungus" refers to all filamentous forms of the subdivision Eumycota and Oomycota. For example, suitable filamentous fungi include, without limitation, *Acremonium, Aspergillus, Emericella, Fusarium, Humicola, Mucor, Myceliophthora, Neurospora, Scytalidium, Thielavia, Tolypocladium,* or *Trichoderma* species. In some embodiments, a suitable filamentous fungus for the purpose of the present invention may be an *Aspergillus aculeatus, Aspergillus awamori, Aspergillus foetidus, Aspergillus japonicus, Aspergillus nidulans, Aspergillus niger,* or *Aspergillus oryzae*.

In some embodiments, a suitable filamentous fungus for the purpose of the present invention may be a *Fusarium bactridioides, Fusarium cerealis, Fusarium crookwellense, Fusarium culmorum, Fusarium graminearum, Fusarium graminum, Fusarium heterosporum, Fusarium negundi, Fusarium oxysporum, Fusarium reticulatum, Fusarium roseum, Fusarium sambucinum, Fusarium sarcochroum, Fusarium sporotrichioides, Fusarium sulphureum, Fusarium torulosum, Fusarium trichothecioides,* or *Fusarium venenatum*.

In some specific embodiments, the filamentous fungus is a *Humicola insolens, Humicola lanuginosa, Mucor miehei, Myceliophthora thermophila, Neurospora crassa, Scytalidium thermophilum,* or *Thielavia terrestris.*

In some embodiments, the filamentous fungus is a *Trichoderma harzianum, Trichoderma koningii, Trichoderma longibrachiatum, Trichoderma reesei,* e.g., RL-P37 (Sheir-Neiss et al., Appl. Microbiol. Biotechnology, 20 (1984) pp. 46-53; Montenecourt B. S., Can., 1-20, 1987), QM9414 (ATCC No. 26921), NRRL 15709, ATCC 13631, 56764, 56466, 56767, or *Trichoderma viride,* e.g., ATCC 32098 and 32086. In certain particular embodiments, the filamentous fungus is a *Trichoderma reesei* RutC30, which is available from the American Type Culture Collection as *Trichoderma reesei* ATCC 56765.

Related to this, in some embodiments, the disclosure provides a whole cell fermentation broth preparation comprising an alpha-glucosidase polypeptide of the invention produced by any one of the filamentous fungi described herein.

A "heterologous" nucleic acid construct or sequence has a portion of the sequence which is not native or existing in a native form to the cell in which it is expressed. Heterologous, with respect to a control sequence refers to a control sequence (i.e. promoter or enhancer) that does not function in nature to regulate the same gene the expression of which it is currently regulating. Generally, heterologous nucleic acid sequences are not endogenous to the cell or part of the genome in which they are present in the native state, and have been added to the cell, by infection, transfection, transformation, microinjection, electroporation, or the like. A "heterologous" nucleic acid construct may contain a control sequence/DNA coding sequence combination that is the same as, or different from a control sequence/DNA coding sequence combination found in the native cell.

As used herein, the term "host cell", includes any fungus, whether a unicellular organism, a cell derived from a multicellular organism and placed in tissue culture or a cell present as part of a multicellular organism, which is susceptible to transformation with a nucleic acid construct according to the disclosure. Such host cells, such as yeast and other fungal cells, or bacteria may be used for replicating DNA and producing polypeptides encoded by nucleotide sequences as used in the disclosure. Suitable cells for the present invention are generally filamentous fungi or yeasts. Particularly preferred are cells from filamentous fungi, preferably *Aspergillus,* such as *A. niger* and *A. tubingensis.* Other preferred organisms include any one of *Aspergillus oryzae, A. awamori, Trichoderma reesei, Trichoderma viride* and *Trichoderma longibrachiatum,* and the like.

As used herein, the terms, "wild-type," "parental," or "reference," with respect to a host organism, refer to a naturally-occurring host organism that does not include foreign genes or genetic materials introduced using genetic engineering, or, with respect to a polypeptide, refers to a man-made substitution, insertion, or deletion at one or more amino acid positions. Similarly, the terms "wild-type," "parental," or "reference," with respect to a polynucleotide, refer to a naturally-occurring polynucleotide that does not include a man-made nucleoside change. However, note that a polynucleotide encoding a wild-type, parental, or reference polypeptide is not limited to a naturally-occurring polynucleotide, and encompasses any polynucleotide encoding the wild-type, parental, or reference polypeptide.

As used herein, the term "variant," with respect to a polypeptide, refers to a polypeptide that differs from a specified wild-type, parental, or reference polypeptide in that it includes one or more naturally-occurring or man-made substitutions, insertions, or deletions of an amino acid. Similarly, the term "variant," with respect to a polynucleotide, refers to a polynucleotide that differs in nucleotide sequence from a specified wild-type, parental, or reference polynucleotide. The identity of the wild-type, parental, or reference polypeptide or polynucleotide will be apparent from context.

As used herein, the term "hybridization" refers to the process by which one strand of nucleic acid forms a duplex with, i.e., base pairs with, a complementary strand, as occurs during blot hybridization techniques and PCR techniques. Stringent hybridization conditions are exemplified by hybridization under the following conditions: 65° C. and 0.1×SSC (where 1×SSC=0.15 M NaCl, 0.015 M Na$_3$ citrate, pH 7.0). Hybridized, duplex nucleic acids are characterized by a melting temperature ($T_m$), where one half of the hybridized nucleic acids are unpaired with the complementary strand. Mismatched nucleotides within the duplex lower the $T_m$.

As used herein, the term "introduced" in the context of inserting a nucleic acid sequence into a cell, means "transfection", "transformation" or "transduction," as known in the art.

As used herein, "transformed" means a cell has been transformed by use of recombinant DNA techniques. Transformation typically occurs by insertion of one or more nucleotide sequences into a cell. The inserted nucleotide sequence may be a heterologous nucleotide sequence, i.e., is a sequence that is not natural to the cell that is to be transformed, such as a fusion protein.

As used herein, "prokaryote" and "prokaryotic" refer to cells which do not contain a nucleus and whose chromosomal material is thus not separated from the cytoplasm. Prokaryotes include, for example, bacteria. Prokaryotic host cells particularly embraced by the present disclosure include those amenable to genetic manipulation and growth in culture. Exemplary prokaryotes routinely used in recombinant protein expression include, but are not limited to, *E. coli, Bacillus licheniformis* (van Leen, et al. (1991) Bio/Technology 9:47-52), *Ralstonia eutropha* (Srinivasan, et al. (2002) Appl. Environ. Microbiol. 68:5925-5932), *Methylobacterium extorquens* (Belanger, et al. (2004) FEMS Microbiol Lett. 231 (2): 197-204), *Lactococcus lactis* (Odd-one, et al. (2009) Plasmid 62(2):108-18) and *Pseudomonas* sp. (e.g., *P. aerugenosa, P. fluorescens* and *P. syringae*). Prokaryotic host cells can be obtained from commercial sources (e.g., Clontech, Invitrogen, Stratagene and the like) or repositories such as American Type Culture Collection (Manassas, Va.).

As used herein, "eukaryotic cells" refer to cells that contain a nucleus and whose chromosomal material is separated from the cytoplasm with partition off different functions to various locations in the cell. In fact, specialized compartments called organelles exist within eukaryotic cells for this purpose. Different organelles play different roles in the cell; for instance, mitochondria generate energy; lysosomes break down and recycle organelles and macromolecules; and the endoplasmic reticulum helps build membranes and transport proteins throughout the cell.

As used herein, the term "expression" refers to the process by which a polypeptide is produced based on a nucleic acid sequence. The process includes both transcription and translation.

As used herein, the terms "recovered," "isolated," and "separated," refer to a compound, protein (polypeptides), cell, nucleic acid, amino acid, or other specified material or component that is removed from at least one other material or component with which it is naturally associated as found in nature. An "isolated" polypeptides, thereof, includes, but is not limited to, a culture broth containing secreted polypeptide expressed in a heterologous host cell.

As used herein, the term "enriched" refers to material (e.g., an isolated polypeptide or polynucleotide) that is in about 50% pure, at least about 60% pure, at least about 70% pure, or even at least about 70% pure.

As used herein, the term "purified" refers to material (e.g., an isolated polypeptide or polynucleotide) that is in a relatively pure state, e.g., at least about 90% pure, at least about 95% pure, at least about 98% pure, or even at least about 99% pure.

As used herein, the term "modification" means herein any chemical modification of the polypeptide comprising or comprising essentially of amino acids 25 to 1035 of SEQ ID NO:3, or comprising or comprising essentially of amino acids 22 to 990 of SEQ ID NO:7, or a homologous sequence thereof, for example, one having at least 70% sequence identity to SEQ ID NO:3 or 7, as well as genetic manipulation of the DNA encoding that polypeptide. The modification can be substitutions, deletions and/or insertions of one or more amino acids as well as changes or replacements of one or more amino acid side chains.

As used herein, the term "artificial variant" means a polypeptide having alpha-glucosidase activity produced by an organism expressing a modified nucleotide sequence of SEQ ID NO:1, or SEQ ID NO:5. The modified nucleotide sequence is obtained through human intervention by modification of the nucleotide sequence disclosed in SEQ ID NO:1, or SEQ ID NO:5.

As used herein, the term "starch" refers to any material comprised of the complex polysaccharide carbohydrates of plants, comprised of amylose and amylopectin with the formula (C6H10O5)x, wherein X can be any number. The term includes plant-based materials such as grains, cereal, grasses, tubers and roots, and more specifically materials obtained from wheat, barley, corn, rye, rice, sorghum, brans, cassava, millet, milo, potato, sweet potato, and tapioca. The meaning of the term "starch" encompasses granular starch. The term "granular starch" refers to raw, i.e., uncooked starch, e.g., starch that has not been subject to gelatinization.

As used herein, the term "synthetic" molecule is produced by in vitro chemical or enzymatic synthesis rather than by an organism.

As used herein, the term "enzyme units" refer to the amount of product formed per time under the specified conditions of the assay.

As used herein, the term "specific activity" refers to the number of moles of substrate that can be converted to product by an enzyme or enzyme preparation per unit time under specific conditions. Specific activity is generally expressed as units (U)/mg of protein.

As used herein, the term "pH range," with reference to an enzyme, refers to the range of pH values under which the enzyme exhibits some certain catalytic activity.

As used herein, the terms "pH stable" and "pH stability," with reference to an enzyme, relate to the ability of the enzyme to retain activity over a wide range of pH values for a predetermined period of time (e.g., 15 min., 30 min., 1 hour).

The terms "thermostable" and "thermostability," with reference to an enzyme, refer to the ability of the enzyme to retain activity after exposure to an elevated temperature. The thermostability of an enzyme, such as an amylase enzyme, is measured by its half-life ($t_{1/2}$) given in minutes, hours, or days, during which half the enzyme activity is lost under defined conditions. The half-life may be calculated by measuring residual alpha-amylase activity following exposure to (i.e., being challenge by) an elevated temperature.

As used herein, the term "degree of polymerization" (DP) refers to the number (n) of anhydro-glucopyranose units in a given saccharide. Examples of DP1 are the monosaccharides glucose and fructose. Examples of DP2 are the disaccharides maltose and sucrose. The term "DE," or "dextrose equivalent," is defined as the percentage of reducing sugar, i.e., D-glucose, as a fraction of total carbohydrate in a syrup.

As used herein, the term "fermented beverage" refers to any beverage produced by a method comprising a fermentation process, such as a microbial fermentation, e.g., a bacterial and/or fungal fermentation. "Beer" is an example of such a fermented beverage, and the term "beer" is meant to comprise any fermented wort produced by fermentation/brewing of a starch-containing plant material. Often, beer is produced exclusively from malt or adjunct, or any combination of malt and adjunct.

As used herein, the term "malt" refers to any malted cereal grain, such as malted barley or wheat.

As used herein, the term "mash" refers to an aqueous slurry of any starch and/or sugar containing plant material, such as grist, e.g., comprising crushed barley malt, crushed barley, and/or other adjunct or a combination thereof, mixed with water later to be separated into wort and spent grains.

As used herein, the term "wort" refers to the unfermented liquor run-off following extracting the grist during mashing.

As used herein, "a cultured cell material," or similar language, refers to a cell lysate or supernatant (including media) that includes an enzyme or a variant thereof as a component. The cell material may be from a heterologous host that is grown in culture for the purpose of producing the enzyme or variant thereof.

IV. Alpha-Glucosidase Polypeptides and Polynucleotides Encoding the Same

The present disclosure relates to certain polypeptides having alpha glucosidase activity isolated, derived or derivable (e.g., synthetic, or obtained using recombinant, genetic engineering means) from *Rasamsonia*, and certain other polypeptides isolated, derived or derivable from *Rasamsonia* homologs. The disclosure also relates to polynucleotides encoding such polypeptides, as well as to compositions comprising such polypeptides. Furthermore, the present disclosure pertains to certain nucleic acid constructs, vectors, host cells and/or mutant cells comprising such polynucleotides, which can be used to produce such polypeptides or compositions comprising such polypeptides. Also provided are methods of using such polypeptides or compositions in industrial settings.

1. Polypeptides Having Alpha-Glucosidase Activity

Alpha-glucosidases (EC 3.2.1.20) hydrolyze terminal, non-reducing alpha-1,4-linked glucose residues in various substrates, releasing glucose. They degrade disaccharides and oligosaccharides quickly while polysaccharides are attacked slowly. Maltose, maltose derivatives, sucrose, aryl-alpha-glucosides, and alkyl-alpha-glucosides can act as substrates. This group of enzyme plays essential roles in carbohydrate metabolism and in glycoprotein processing.

1.1 Classification of Alpha-Glucosidase

To date, a very large number of diverse glycoside hydrolases have been discovered. They are classified into glycoside hydrolase families (GH families) based on their amino-acid sequence similarities. As such, enzymes with the same GH family numbers do not necessarily exert the same enzymatic activities, and the converse is also true, that is, enzymes having the same catalytic activities or mechanisms do not always fall within the same GH families.

Glycoside hydrolases acting on alpha-glucose residues from the non-reducing end are found in GH families 4, 13, 31, 63, 97 and 122, with the majority falling within two GH families: 13 and 31. See, Henrissat, B. (1991) Biochem. J. 280:309-316; Kimura, A., et al. (1992) Biosci. Biotechnol. Biochem. 56:1368-1370; Henrissat, B. & Bairoch, A. (1993) Biochem. J. 293:781-788.

Glycosyl hydrolases having alpha-glucosidase activity can be found in a wide variety of organisms. See, Chiba, S. (1988), supra, at pp. 109-116. Alpha-glucosidases from bacteria, yeasts, and insects typically belong to GH13, and have sequence regions 1, 2, 3 and 4, in which the amino acids critical for catalytic reactions are conserved. See, Matsuura, Y. (2002) Biologia, Bratislava 57 (Suppl. 11):21-27; Svensson, B. et al. (2002) Biologia, Bratislava 57 (Suppl. 11): 5-19). Alpha-glucosidases from plants, animals, molds, and bacteria (two species) as well as alpha-glucan lyase (EC 4.2.2.13) and alpha-xylosidases (EC 3.2.1.-) are typically members of GH31. See, Bojsen, K. et al. (1999) Plant Mol. Biol. 40:445-454; Okayama, M. et al. (2004) Protein Expres. Purif. 37:170-179; and Frandsen, T. P. & Svensson, B. (1998) Plant Mol. Biol. 37:1-13.

Catalytic activity-wise, alpha-glucosidases are divided into three types. Type I alpha-glucosidases hydrolyze heterogeneous substrates, such as aryl glucosides and sucrose, more efficiently than they hydrolyze maltose. Type II alpha-glucosidases prefer maltose and isomaltose as substrates, and have low activities toward aryl glucosides. Type III alpha-glucosdiases have the same substrate specificity as type II but in addition can hydrolyze polysaccharides such as amylose and starch. See, Chiba S. (1988), supra; Chiba, S. (1997) Biosci. Biotechnol. Biochem., 61:1233-1239.

1.2 Activity of Alpha-Glucosidase

Alpha-glucosidases display broad substrate specificity for alpha-glucosides, which include ipanose, isomaltose, isopanose, maltotriose, turanose, and maltose. Aside from being able to hydrolyze synthetic alpha-glucoside and oligosaccharide substrates, alpha-glucosidases also can hydrolyze alpha-glucans such as soluble starch and glycogen.

The main physiological role of most exo-type glycosidases such as alpha-glucosidase is to produce monosaccharides that are utilized as carbon and energy sources. However, transglycosylation activities of exo-type glycosidases sometimes play physiologically important roles in gene regulation involved in carbohydrate utilization. Transglycosylation activity of the alpha-glucosidases has been applied in industries to produce isomaltooligosaccharides and also to conjugate sugars to biologically useful materials, aiming to improve their chemical properties and physiological functions. See, Yamamoto, I. et al. (1990) Biochim Biophys. Acta 1035:44-50; Murase, H. et al. (1997) Lipids. 32:73-78.

In general, alpha-glucosidases degrade disaccharides and oligosaccharides quickly while polysaccharides are attacked slowly. There are exceptions, however, for example, the alpha-glucosidase from rice showed starch granule-degrading and binding abilities. See, Nakai et al. (2004) Plant Polysaccharide Workshop, July 21-23. Similar phenomena were observed in all plant alpha-glucosidases. Alpha-glucosidases from mold (yeasts and fungi) tend not to have any degrading activity or binding ability toward raw starch. Plant and mold alpha-glucosidases are members of GH31. Therefore, it might be surmised that there are certain structural differences in alpha-glucosidases from plant and mold.

Most GH31 enzymes catalyze a retaining hydrolytic reaction, with the one clear exception being that GH31 glucan lyases catalyze an elimination reaction. It has been reported that a small amount of 1,5-anhydro-D-fructose (AF) is produced by an *Aspergillus niger* GH31 alpha-glucosidase from malto-oligosacharides via an elimination reaction, indicating that the *Aspergillus niger* alpha-glucosidase has the activity of alpha-1,4-glucan lyase. See, Maneesan J. et al. (2014) Biosci. Biotech. Biochem. 78:2064-2068.

1.3 Mechanism and Structure of Alpha-Glucosidases

GH31 proteins share the same catalytic domain containing a (β/α) 8-barrel fold in which two asparagine (Asp) residues on the β4 and β6 strands are the catalytic nucleophile and general acid/base catalyst, respectively. See, Ernst H A, et al. (2006) J. Mol. Biol. 358:1106-1124; Lovering A L, et al. (2005) J. Biol. Chem., 280:2105-2115; Okuyama M, et al. (2001) Eur. J. Biochem. 268:2270-2280.

In general, every hydrolysis of a glycosidic linkage by a glycosidase is a reaction in which the product retains (α→α or β→β) or inverts (α→β or β→α) the anomeric configuration of the substrate. Even if a substrate, such as starch or oligosaccharide, consists only of alpha-glucosyl residues, alpha-glucosidases produce alpha-anomer by a "retaining" reaction.

Retaining enzymes, such as the retaining-type alpha glucosidases, typically have two catalytic carboxylic acids separated by about 5.5 Å in their three-dimensional structures. See, Davies G. J. & Henrissat B. (1995) Structure, 3:853-859; McCarter J. D. & Withers S. G. (1994) Curr. Opin. Struct. Biol. 4:885-892. Such enzymes utilize a double displacement mechanism in which general acid protonation of the glucosidic oxygen and nucleophilic attack at C1 leads to CO bond cleavage and formation of a covalent enzyme glycosyl intermediate. In a subsequent deglycosylation step, the intermediate is attacked by an incoming water molecule, activated by a general base catalyst. See, McIntosh L. P. et al. (1996) Biochemistry, 35:9958-9966.

Both the glycosylation and the deglycosylation steps are proposed to proceed through transition states with substantial oxocarbenium ion character. See, Davies G. J. & Henrissat B. (1995), supra; McCarter J. D. & Withers S. G. (1994), supra.

The catalytic residues have been investigated using point mutations made on Aspartic acid and Glutamic acid residues, which are conserved in the amino acid sequences of GH31 alpha-glucosidases. Target acidic amino acids, candidates for catalytic residues, were six Aspartic acid residues, namely D218, D287, D355, D481, D647, and 877D, and two Glutamic acid residues, namely E484, and E714, which were replaced by Asparagine/Alanine/Glutamic acid and Glutamine/Alanine/Aspartic acid, respectively. Okuyama, M. (2001) Eur. J. Biochem. 268:2270-2280. From such studies, it was concluded that two of the Aspartic acid residues, D481 and D647, are the most likely catalytic residues, because D481N/A and D647/N/A substitutions resulted in loss of hydrolytic activity against maltose and PNP alpha-glucoside substrates, and of D-glucal-hydration activity. These essential residues, D481 and D647, are located in the conservative sequence segments observed in all the GH31 enzymes. See, Kimura, A. (2000) Trends Glycosci. Glycotechnol. 12:373-380; Okuyama, M. (2001) supra.

1.4 Sources of Alpha-Glucosidase

A polypeptide having alpha glucosidase activity, such as one of the present disclosure may be obtained from microorganisms of any genus. A preferred source of such polypeptides would be one that secrets such polypeptides extracellularly.

A polypeptide of the present disclosure may be one derived from a bacterial source. For example, the polypeptide may be derived from a gram positive bacterium, such as, e.g., a *Bacillus alkalophilus, Bacillus amyloliquefaciens, Bacillus brevis, Bacillus circulans, Bacillus coagulans, Bacillus lautus, Bacillus lentus, Bacillus licheniformis, Bacillus megaterium, Bacillus stearothermophilus, Bacillus subtilis*, or *Bacillus thuringiensis*; or a *Streptomyces* such as, e.g., a *Streptomyces lividans* or *Streptomyces murinus*; or a gram negative bacterium, such as, e.g., an *E. coli* or a *Pseudomonas* sp.

A polypeptide of the present disclosure may also be derived from a fungal source. For example, a polypeptide of the present disclosure may be derived from a yeast, such as, e.g., a *Candida, Kluyveromyces, Pichia, Saccharomyces, Schizosaccharomyces*, or *Yarrowia*. Alternatively a polypeptide of the present disclosure may be derived from a filamentous fungus, such as, e.g., an *Acremonium, Aspergillus, Aureobasidium, Cryptococcus, Filibasidium, Fusarium, Humicola, Magnaporthe, Mucor, Myceliophthora, Neocallimastix, Neurospora, Paecilomyces, Penicillium, Piromyces, Schizophyllum, Talaromyces, Thermoascus, Thielavia, Tolypocladium, Trichoderma* or *Rasamsonia*.

In a preferred aspect, the polypeptide is derived from a *Saccharomyces carlsbergensis, Saccharomyces cerevisiae, Saccharomyces diastaticus, Saccharomyces douglasii, Saccharomyces kluyveri, Saccharomyces norbensis*, or *Saccharomyces oviformis*.

In another preferred aspect, the polypeptide of the disclosure is derived from an *Aspergillus acufeatus, Aspergillus awamori, Aspergillus fumigatus, Aspergillus foetidus, Aspergillus japonicus, Aspergillus nidulans, Aspergillus niger, Aspergillus oryzae, Fusarium bactridioides, Fusarium cerealis, Fusarium crookwellense, Fusarium culmorum, Fusarium graminearum, Fusarium graminum, Fusarium heterosporum, Fusarium negundi, Fusarium oxysporum, Fusarium reticulatum, Fusarium roseum, Fusarium sambucinum, Fusarium sarcochroum, Fusarium sporotrichioides, Fusarium sulphureum, Fusarium torulosum, Fusarium trichothecioides, Fusarium venenatum, Humicola insolens, Humicola lanuginosa, Mucor miehei, Myceliophthora thermophila, Neurospora crassa, Penicillium purpurogenum, Trichoderma harzianum, Trichoderma koningii, Trichoderma longibrachiatum, Trichoderma reesei, Trichoderma viride, Rasamsonia argillacea, Rasamsonia brevistipitata, Rasamsonia byssochlamydoides, Rasamsonia cylindrospora, Rasamsonia composticola, Rasamsonia eburnean* or *Rasamsonia emersonii*.

For the aforementioned species, it is understood that the disclosure and source species would encompass both the perfect and imperfect states of such organsims, and other taxonomic equivalents thereof, e.g., anamorphs, regardless of the species name by which they are known. Those skilled in the art will readily recognize the identity of appropriate equivalents of such source species.

Strains of the above-mentioned species are readily accessible to the public in a number of culture collections, such as the American Type Culture Collection (ATCC), Deutsche Sammlung von Mikroorganismen and Zellkulturen GmbH (DSM), Centraalbureau Voor Schimmelcultures (CBS), and Agricultural Research Service Patent Culture Collection, Northern Regional Research Center (NRRL).

Such polypeptides may be identified and/or obtained from other sources including microorganisms isolated from nature (e.g., soil, composts, water, etc.). A variety of known techniques may be applied to isolate microorganisms from natural habitats. Polynucleotides can then be obtained using screening a genomic or cDNA library of various microorganisms. For example, polynucleotide sequences encoding polypeptides of interest can be detected using probe(s) of polynucleotide sequences, and thereafter the polynucleotides can be isolated, cloned, using various techniques well practiced by those skilled in the art (see, e.g., Sambrook et al., 1989, supra).

Suitably, the polypeptide is an isolated polypeptide derived or derivable from *Rasamsonia*, (e.g., synthetic or obtained via recombinant or genetic engineering means) from *Rasamsonia composticola*, comprising a polypeptide sequence of SEQ ID NO:3 or SEQ ID NO:7, or mature polypeptides thereof. Also suitably the polypeptide is one isolated, derived or derivable from a *Rasamsonia* homolog, for example, one that comprises a polypeptide sequence that is at least about 70% identical (e.g., at least about 70% identical, at least about 75% identical, at least about 80% identical, at least about 85% identical, at least about 90% identical, at least about 91% identical, at least about 92% identical, at least about 93% identical, at least about 94% identical, at least about 95% identical, at least about 96% identical, at least about 97% identical, at least about 98% identical, at least about 99% identical, or even higher % identical but not 100% identical) to SEQ ID NO:3 or SEQ ID NO:7, or the sequences of the mature polypeptides thereof. Furthermore, suitably the polypeptide is one that is isolated, derived or derivable from *Rasamsonia*, comprising a polypeptide that is a contiguous stretch of at least about 550 amino acid residues, at least about 600 amino acid residues, at least about 650 amino acid residues, at least about 700 amino acid residues, at least about 750 amino acid residues, at least about 800 amino acid residues, or even at least about 850 amino acid residues of SEQ ID NO:3 or 7.

2. Alpha-Glucosidase from *Rasamsonia*

An aspect of the present disclosure relates to polypeptides having alpha-glucosidase activity isolated, derived, or derivable from the microorganism genus *Rasamsonia*. *Rasamsonia*, particular the type species *Rasamsonia emersonii*, was initially identified via a polyphasic study of thermotolerant and thermophilic species in Trichocomaceae. See, Houbraken et al. (2012) Antonie van Leeuwenhoek 101:403-421). To date, six species of the genus *Rasamsonia* were reported, of which five were transferred from *Talaromyces* or *Geosmithia*, and one was newly described. See, Houbraken et al. (2012) supra.

A number of enzymes derived from this genus of microorganisms have been developed for commercial use. For example, a thermostable extracellular enzyme from *Rasamsonia emersonii* has been used in the wheat-baking process. Waters et al. (2010) J. Agric. Food Chem. 58:7415-7422.

The microorganism *Rasamsonia composticola* is thermophilic with optimal growth temperature of 45-50° C., and minimum growth temperature of 30° C. See, Yuan-Ying Su & Lei Cai (2012) Mycol. Progress, doi: 10.1007/s11557-012-0827-9.

2.1 Polypeptides of *Rasamsonia* Alpha-Glucosidase

In one aspect, polypeptides of alpha-glucosidase isolated, derived, or derivable from *Rasamsonia* are provided. In another aspect, polypeptides having alpha-glucosidase activity isolated, derived, or derivable from homologs of *Rasamsonia* are provided.

The sequence of polypeptides with alpha-glucosidase activity derived or derivable from *Rasamsonia* or homologs thereof may be (1) as set forth in SEQ ID NO:3 or 7; or (2)

comprising SEQ ID NO:3 or 7, or any contiguous stretch of SEQ ID NO:3 or 7 of at least 500 amino acid residues in length; or (3) an isolated, synthetic or engineered molecule with alpha glucosidase activity, comprising a polypeptide sequence that is at least about 70% identical (e.g., at least about 70% identical, at least about 75% identical, at least about 80% identical, at least about 85% identical, at least about 90% identical, at least about 91% identical, at least about 92% identical, at least about 93% identical, at least about 94% identical, at least about 95% identical, at least about 96% identical, at least about 97% identical, at least about 98% identical, at least about 99% identical, or even at a higher % identity, but not 100% identical) to that of SEQ ID NO:3 or 7, or to any contiguous stretch of SEQ ID NO:3 or 7 of at least 500 amino acid residues in length.

In some embodiments, certain of the present alpha-glucosidase polypeptides each has a defined degree of amino acid sequence identity to SEQ ID NO:3 or 7, or to a contiguous stretch of amino acid sequence of SEQ ID NO:3 or 7 of at least 500 amino acid residues in length, for example, at least about 70%, (e.g., at least about 70%, at least about 75%, at least about 80%, at least about 85%, at least about 90%, at least about 91%, at least about 92%, at least about 93%, at least about 94%, at least about 95%, at least about 96%, at least about 97%, at least about 98%, at least about 99%, or even higher identity but not 100% identity). In some embodiments, such polypeptides may be synthetic polypeptides, or may be ones isolated from species that are not the same as where SEQ ID NO:3 or 7 are natively present, or may even be ones that are engineered or derived from additions, mutations, substitutions, deletions of SEQ ID NO:3 or 7.

In some embodiments, each of the present alpha-glucosidase polypeptides comprises conservative substitution(s) of one or several amino acid residues relative to the amino acid sequence of SEQ ID NO:3 or 7. The amino acid changes are of such a nature that the physical and/or chemical properties of the polypeptides are altered. For example, amino acid changes may improve the thermal stability of the polypeptide, alter the substrate specificity, change the pH optimum, and the like.

In some embodiments, the present alpha-glucosidase polypeptides are each derived from a parental alpha-glucosidase having a defined degree of amino acid sequence identity to SEQ ID NO:3 or 7, for example, at least about 70% (e.g., at least about 70%, at least about 75%, at least about 80%, at least about 85%, at least about 90%, at least about 91%, at least about 92%, at least about 93%, at least about 94%, at least about 95%, at least about 96%, at least about 97%, at least about 98%, or even at least about 99% or higher, but not 100% identity).

Examples of conservative amino acid substitutions are listed in the Table 1. Some conservative mutations can be produced by genetic manipulation, while others are produced by introducing synthetic amino acids into a polypeptide other means.

TABLE 1

Conservative amino acid substitutions

| For Amino Acid | Code | Replace with any of |
|---|---|---|
| Alanine | A | D-Ala, Gly, beta-Ala, L-Cys, D-Cys |
| Arginine | R | D-Arg, Lys, D-Lys, homo-Arg, D-homo-Arg, Met, Ile, D-Met, D-Ile, Orn, D-Orn |
| Asparagine | N | D-Asn, Asp, D-Asp, Glu, D-Glu, Gln, D-Gln |

TABLE 1-continued

Conservative amino acid substitutions

| For Amino Acid | Code | Replace with any of |
|---|---|---|
| Aspartic Acid | D | D-Asp, D-Asn, Asn, Glu, D-Glu, Gln, D-Gln |
| Cysteine | C | D-Cys, S-Me-Cys, Met, D-Met, Thr, D-Thr |
| Glutamine | Q | D-Gln, Asn, D-Asn, Glu, D-Glu, Asp, D-Asp |
| Glutamic Acid | E | D-Glu, D-Asp, Asp, Asn, D-Asn, Gln, D-Gln |
| Glycine | G | Ala, D-Ala, Pro, D-Pro, b-Ala, Acp |
| Isoleucine | I | D-Ile, Val, D-Val, Leu, D-Leu, Met, D-Met |
| Leucine | L | D-Leu, Val, D-Val, Leu, D-Leu, Met, D-Met |
| Lysine | K | D-Lys, Arg, D-Arg, homo-Arg, D-homo-Arg, Met, D-Met, Ile, D-Ile, Orn, D-Orn |
| Methionine | M | D-Met, S-Me-Cys, Ile, D-Ile, Leu, D-Leu, Val, D-Val |
| Phenylalanine | F | D-Phe, Tyr, D-Thr, L-Dopa, His, D-His, Trp, D-Trp, Trans-3,4, or 5-phenylproline, cis-3,4, or 5-phenylproline |
| Proline | P | D-Pro, L-I-thioazolidine-4-carboxylic acid, D-or L-1-oxazolidine-4-carboxylic acid |
| Serine | S | D-Ser, Thr, D-Thr, allo-Thr, Met, D-Met, Met(O), D-Met(O), L-Cys, D-Cys |
| Threonine | T | D-Thr, Ser, D-Ser, allo-Thr, Met, D-Met, Met(O), D-Met(O), Val, D-Val |
| Tyrosine | Y | D-Tyr, Phe, D-Phe, L-Dopa, His, D-His |
| Valine | V | D-Val, Leu, D-Leu, Ile, D-Ile, Met, D-Met |

In some embodiments, the present alpha-glucosidase polypeptides may each comprise a deletion, insertion, substitution or addition of one or a few amino acid residues relative to the amino acid sequence of SEQ ID NO:3 or 7. In all cases, the expression "one or a few amino acid residues" refers to 10 or less, i.e., 1, 2, 3, 4, 5, 6, 7, 8, 9, or 10, amino acid residues.

Single or multiple amino acid substitutions can be made and tested using known methods of mutagenesis, recombination, and/or shuffling, followed by a relevant screening procedure, such as those disclosed by Reidhaar-Olson & Sauer, (1988) Science 241:53-57; Bowie and Sauer, (1989) Proc. Natl. Acad. Sci. USA 86: 2152-2156; WO 95/17413; or WO 95/22625. Other useful methods include error-prone PCR, phage display (see, e.g., Lowman et al (1991) Biochem. 30:10832-10837; U.S. Pat. No. 5,223,409; WO 92/06204), and region-directed mutagenesis (see, e.g., Derbyshire et al., (1986) Gene 46: 145; Ner et al. (1988) DNA 7:127).

Mutagenesis/shuffling methods can be used to achieve the same purpose; alternatively they can be combined with high-throughput, automatic screening methods to detect activity of cloned, mutagenized polypeptides expressed by host cells. Mutagenized DNA molecules that encode active polypeptides can be recovered from the host cells and rapidly sequenced using standard methods in the art. These methods allow the rapid determination of the importance of individual amino acid residues in a polypeptide of interest, and can be applied to polypeptides of unknown structure.

It will be apparent to those skilled in the art that such substitutions can be made outside the regions critical to the function of the molecule and still result in an active polypeptide. Amino acid residues essential to the activity of the polypeptide encoded by an isolated polynucleotide of the disclosure, and therefore preferably not subject to substitution, may be identified according to procedures known in the art, such as site-directed mutagenesis or alanine-scanning mutagenesis (see, e.g., Cunningham & Wells (1989) Science 244:1081-1085). In the latter technique, single alanine mutations are introduced at every residue in the molecule, and the resultant mutant molecules are tested for biological activity (i.e., alpha-glucosidase activity) to identify amino acid residues that are critical to the activity of the molecule. See also, Hilton et al. (1996) J. Biol. Chem. 271:4699-4708.

The active sites of the enzymes or other biological interaction can also be determined by physical analysis of structure, as determined by such techniques as nuclear magnetic resonance, crystallography, electron diffraction, or photo affinity labeling, in conjunction with mutation of putative contact site amino acids. See, e.g., de Vos et al. (1992) Science 255:306-312; Smith et al. (1992) J. Mol. Biol. 224: 899-904; Wlodaver et al. (1992) FEBS Lett. 309:59-64.

The identities of essential amino acids can also be inferred from analysis of identities with polypeptides which are related to a polypeptide according to the disclosure.

The present alpha-glucosidase may be "precursor," "immature," or "full-length," in which case they include a signal sequence, or "mature," in which case they lack a signal sequence. The present alpha-glucosidase polypeptides may also be truncated to remove the N or C-termini, so long as the resulting polypeptides retain alpha-glucosidase activity.

2.2 Polynucleotides of *Rasamsonia* Alpha-Glucosidase

In another aspect, nucleotide sequences encoding an alpha-glucosidase polypeptide are provided.

In certain embodiments, the nucleotide sequence is set forth as SEQ ID NO:1 or 5. In a further embodiment, the nucleotide sequence is one encoding the mature polypeptide, comprising the coding region of SEQ ID NO:1 or 5.

The present disclosure also encompasses nucleotide sequences which encode a polypeptide having the amino acid sequence of SEQ ID NO:3 or 7, or the mature polypeptide thereof, or a somewhat different but still functional (i.e., has alpha-glucosidase activity) variant thereof (e.g., one that is at least about 80%, 90% or 95% identical to SEQ ID NO:3 or 7), which differ from SEQ ID NO:1 or 5 by virtue of the degeneracy of the genetic code.

The nucleic acid may encode an alpha-glucosidase polypeptide having a specified degree of amino acid sequence identity to SEQ ID NO:3 or 7, or to a contiguous stretch of at least 500 amino acid residues of SEQ ID NO:3 or 7. In some embodiments, the nucleic acid encodes an alpha-glucosidase having at least about 70%, at least about 75%, at least about 80%, at least about 85%, at least about 90%, at least about 91%, at least about 92%, at least about 93%, at least about 94%, at least about 95%, at least about 96%, at least about 97%, at least about 98%, or even at least about 99% or higher amino acid sequence identity to SEQ ID NO:3 or 7, or to a contiguous stretch of at least 500 amino acid residues of SEQ ID NO:3 or 7.

The techniques used to isolate or clone a polynucleotide encoding a polypeptide are known in the art including isolation from genomic DNA, preparation from cDNA, or a combination thereof. The cloning of the polynucleotides of the present disclosure from such genomic DNA can be effected, e.g., by using the polymerase chain reaction (PCR) or probe screening of expression libraries to detect cloned DNA fragments with shared structural features. See, e.g., Innis et al. (1990) PCR: A Guide to Methods and Application, Academic Press, New York. Other nucleic acid amplification procedures such as ligase chain reaction (LCR), ligated activated transcription (LAT) and nucleotide sequence-based amplification (NASBA) may be used. The polynucleotides may be cloned from a cell of *Aspergillus, Trichoderma* or another or related organism and thus, for example, may be an allelic or species variant of the polypeptide encoding region of the nucleotide sequence.

In yet another aspect, the present invention relates to isolated polypeptides having alpha-glucosidase activity which are encoded by polynucleotides which hybridize under very low stringency conditions, preferably low stringency conditions, more preferably medium stringency conditions, more preferably medium-high stringency conditions, even more preferably high stringency conditions, and most preferably very high stringency conditions with (i) nucleotides 43 to 2643 of SEQ ID NO:1, or nucleotides 58 to 3164 of SEQ ID NO: 5; (ii) the cDNA sequence contained in nucleotides 43 to 2643 of SEQ ID NO:1, or in nucleotides 58 to 3164 of SEQ ID NO: 5; (iii) a subsequence of (i) or (ii), or (iv) a complementary strand of (i), (ii), or (iii). Hybridization techniques are common place and readily available to those skilled in the art who wishes to practice them. See, J. Sambrook et al. (1989) Molecular Cloning, A Laboratory Manual, 2d edition, Cold Spring Harbor, N.Y.

The nucleotide sequence of SEQ ID NO:1, or SEQ ID NO:5; or subsequence thereof, as well as the amino acid sequence of SEQ ID NO:3 or SEQ ID NO:7; or fragments thereof, may be used to design a nucleic acid probe to identify and clone DNA encoding polypeptides having alpha-glucosidase activity from strains of different genera or species according to methods well known in the art.

In particular, such probes can be used for hybridization with the genomic or cDNA of the genus or species of interest, following standard southern blotting procedures, in order to identify and isolate the corresponding gene therein. Such probes can be considerably shorter than the entire sequence, but should be at least 14, preferably at least 25, more preferably at least 35, and most preferably at least 70 nucleotides in length. It is, however, preferred that the nucleic acid probe is at least 100 nucleotides in length. For example, the nucleic acid probe may be at least 200 nucleotides, preferably at least 300 nucleotides, more preferably at least 400 nucleotides, or most preferably at least 500 nucleotides in length. Even longer probes may be used, e.g., nucleic acid probes which are at least 600 nucleotides, at least preferably at least 700 nucleotides, more preferably at least 800 nucleotides, or most preferably at least 900 nucleotides in length. Both DNA and RNA probes can be used. The probes are typically labeled for detecting the corresponding gene (for example, with $^{32}P$, $^{3}H$, $^{35}S$, biotin, or avidin). Such probes are encompassed by the present disclosure.

A genomic DNA or cDNA library prepared from such other organisms may, therefore, be screened for DNA which hybridizes with the probes described above and which encodes a polypeptide having alpha-glucosidase activity. Genomic or other DNA from such other organisms may be separated by agarose or polyacrylamide gel electrophoresis, or other separation techniques. DNA from the libraries or the separated DNA may be transferred to and immobilized on nitrocellulose or other suitable carrier material. In order to identify a clone or DNA which is homologous with SEQ ID NO:1, or SEQ ID NO:5, or subsequences thereof, the carrier material is used in a southern blot. For purposes of the present disclosure, hybridization indicates that the nucleotide sequence hybridizes to a labeled nucleic acid probe corresponding to the nucleotide sequence shown in SEQ ID NO:1, or SEQ ID NO:5, their complementary strands, or subsequences thereof, under very low to very high stringency conditions. Molecules to which the nucleic acid probe hybridizes under these conditions can be detected using X-ray film.

In some embodiments, the alpha-glucosidase polypeptides of the instant disclosure are encoded by polynucleotide or nucleic acid sequences that hybridize under stringent conditions to a nucleic acid sequence that is complementary one encoding SEQ ID NO:3 or 7, or a fragment of at least 500 contiguous amino acid residues in length of SEQ ID NO:3 or 7.

In another example, the nucleic acid hybridizes under stringent or very stringent conditions to a nucleic acid complementary to a nucleic acid encoding an amylase having at least about 70%, at least about 75%, at least about 80%, at least about 85%, at least about 90%, at least about 91%, at least about 92%, at least about 93%, at least about 94%, at least about 95%, at least about 96%, at least about 97%, at least about 98%, or even at least about 99%, identity to SEQ ID NO:3 or 7.

In some embodiments, the present compositions and methods include nucleic acids that encode any recombinant or engineered *Rasamsonia* alpha-glucosidase having deletions, insertions, or substitutions, such as those mentioned above. It will be appreciated that due to the degeneracy of the genetic code, a plurality of nucleic acids may encode the same polypeptide having the same amino acid sequence.

The present alpha-glucosidase polypeptide may be a "chimeric" or "hybrid" polypeptide, in that it includes at least a portion of a first alpha-glucosidase polypeptide, and at least a portion of a second alpha-glucosidase polypeptide. The present alpha-glucosidases may further include heterologous signal sequence, an epitope to allow tracking or purification, or the like. Examples of heterologous signal sequences are from *Humicola grisea* Cel7A, *Aspergillus niger* glaA and *Trichoderma reesei* CBH1.

A nucleic acid that encodes an alpha-glucosidase can be operably linked to various promoters and regulators in a vector suitable for expressing the alpha-glucosidase in host cells. Examples of promoters are from *Aspergillus oryzae* TAKA amylase, *Rhizomucor miehei* aspartic proteinase, *Aspergillus niger* neutral alpha-amylase, *Aspergillus niger* acid stable alpha-amylase, *Aspergillus niger* glucoamylase. Such a nucleic acid can also be linked to other coding sequences, e.g., to encode a chimeric polypeptide.

Nucleic acids may encode a "full-length" ("fl" or "FL") alpha-glucosidase, which includes a signal sequence, only the mature form of an alpha glucosidase, which lacks the signal sequence, or a truncated form of an alpha-glucosidase, which lacks the N or C-terminus of the mature form. The nucleic acid sequences are suitably of sufficient length to encode an active alpha-glucosidase enzyme.

3. Production of a Polypeptide Having Alpha-Glucosidase Activity

The alpha-glucosidase polypeptides of the invention can be produced in host cells, for example, by secretion or intracellular expression. A cultured cell material (e.g., a whole-cell broth) comprising an alpha-glucosidase can be obtained following secretion of the alpha-glucosidase into the cell medium. Optionally, the alpha-glucosidase can be isolated from the host cells, or even isolated from the cell broth, depending on the desired purity of the final alpha-glucosidase polypeptide. A gene encoding an alpha-glucosidase can be cloned and expressed using methods known in the art. Suitable host cells may be bacterial, fungal (including yeast and filamentous fungi), and plant (including algae) cells. Particularly useful host cell may be *Aspergillus niger*, *Aspergillus oryzae* or *Trichoderma reesei*. Other suitable host cells may be bacterial, e.g., *Bacillus subtilis*, *B. licheniformis*, or *Streptomyces* cells.

Additionally, the host may express one or more other enzymes, proteins, peptides, or other substances, some of which may be beneficial to various intended industrial applications. For example, the host cell may produce biochemicals in addition to enzymes, which may enhance the catalytic efficacy of the alpha-glucosidase polypeptides.

3.1. Vectors

A DNA construct comprising a nucleic acid encoding an alpha-glucosidase polypeptide can be constructed such that it is suitable to be expressed in a host cell. Because of the known degeneracy in the genetic code, different polynucleotides that encode an identical amino acid sequence can be designed and made with routine skill. It is also known that, depending on the desired host cells, codon optimization may be required prior to attempting expression.

A polynucleotide encoding an alpha-glucosidase polypeptide of the present disclosure can be incorporated into a vector. Vectors can be transferred to a host cell using known transformation techniques, such as those disclosed below.

A suitable vector may be one that can be transformed into and replicated within a host cell. For example, a vector comprising a nucleic acid encoding an alpha-glucosidase polypeptide of the present disclosure can be transformed and replicated in a bacterial host cell as a means of propagating and amplifying the vector. The vector may also be suitably transformed into an expression host, such that the encoding polynucleotide is expressed as a functional alpha-glucosidase enzyme.

Suitable expression host cells may be filamentous fungal cells. The Fungal Genetics Stock Center (FGSC) Catalogue of Strains lists a number of suitable vectors for expression in fungal host cells. See FGSC, Catalogue of Strains, University of Missouri, at www.fgsc.net (last modified Jan. 17, 2007). A representative useful vector is pTrex3gM (see, Published US Patent Application 20130323798) and pTTT (see, Published US Patent Application 20110020899), which can be inserted into genome of host. The vectors pTrex3gM and pTTT can both be modified with routine skill such that they comprise and express a polynucleotide encoding an alpha-glucosidase polypeptide of the invention.

A vector useful for this purpose typically includes the components of a cloning vector, such as, for example, an element that permits autonomous replication of the vector in the selected host organism and one or more phenotypically detectable markers for selection purposes. The expression vector normally comprises control nucleotide sequences such as a promoter, operator, ribosome binding site, translation initiation signal and optionally, a repressor gene or one or more activator genes. Additionally, the expression vector may comprise a sequence coding for an amino acid sequence capable of targeting the alpha-glucosidase to a host cell organelle such as a peroxisome, or to a particular host cell compartment. Such a targeting sequence includes but is not limited to the sequence, SKL. For expression under the direction of control sequences, the nucleic acid sequence of the alpha-glucosidase is operably linked to the control sequences in proper manner with respect to expression.

A polynucleotide encoding an alpha-glucosidase polypeptide of the present invention can be operably linked to a promoter, which allows transcription in the host cell. The promoter may be any DNA sequence that shows transcriptional activity in the host cell of choice and may be derived from genes encoding proteins either homologous or heterologous to the host cell. Examples of promoters for directing the transcription of the DNA sequence encoding an alpha-glucosidase, especially in a bacterial host, include the promoter of the lac operon of *E. coli*, the *Streptomyces coelicolor* agarase gene dagA or celA promoters, the promoters of the *Bacillus licheniformis* amylase gene (amyL), the promoters of the *Bacillus stearothermophilus* maltogenic amylase gene (amyM), the promoters of the *Bacillus*

*amyloliquefaciens* amylase (amyQ), the promoters of the *Bacillus subtilis* xylA and xylB genes, and the like.

For transcription in a fungal host, examples of useful promoters include those derived from the gene encoding *Aspergillus oryzae* TAKA amylase, *Rhizomucor miehei* aspartic proteinase, *Aspergillus niger* neutral α-amylase, *Aspergillus niger* acid stable α-amylase, *Aspergillus niger* glucoamylase, *Rhizomucor miehei* lipase, *Aspergillus oryzae* alkaline protease, *Aspergillus oryzae* triose phosphate isomerase, *Aspergillus nidulans* acetamidase and the like. When a gene encoding an alpha-glucosidase is expressed in a bacterial species such as an *E. coli*, a suitable promoter can be selected, for example, from a bacteriophage promoter including a T7 promoter and a phage lambda promoter. Along these lines, examples of suitable promoters for the expression in a yeast species include but are not limited to the Gal 1 and Gal 10 promoters of *Saccharomyces cerevisiae* and the *Pichia pastoris* AOX1 or AOX2 promoters. Expression in filamentous fungal host cells often involves cbh1, which is an endogenous, inducible promoter from *T. reesei*. See Liu et al. (2008) *Acta Biochim. Biophys. Sin* (Shanghai) 40(2): 158-65.

The coding sequence can be operably linked to a signal sequence. The DNA encoding the signal sequence may be a DNA sequence naturally associated with the alpha-glucosidase gene of interest to be expressed, or may be from a different genus or species as the alpha-glucosidase. A signal sequence and a promoter sequence comprising a DNA construct or vector can be introduced into a fungal host cell and can be derived from the same source. For example, the signal sequence may be the *Trichoderma reesei* cbh1 signal sequence, which is operably linked to a cbh1 promoter.

An expression vector may also comprise a suitable transcription terminator and, in eukaryotes, polyadenylation sequences operably linked to the DNA sequence encoding an alpha-glucosidase. Termination and polyadenylation sequences may suitably be derived from the same sources as the promoter.

The vector may further comprise a DNA sequence enabling the vector to replicate in the host cell. Examples of such sequences are the origins of replication of plasmids pUC19, pACYC177, pUB110, pE194, pAMB1, and 0.1702.

The vector may also comprise a selectable marker, e.g., a gene the product of which complements a defect in the isolated host cell, such as the dal genes from *B. subtilis* or *B. licheniformis*, or a gene that confers antibiotic resistance such as, e.g., ampicillin, kanamycin, chloramphenicol or tetracycline resistance. Furthermore, the vector may comprise *Aspergillus* selection markers such as amdS, argB, niaD and xxsC, a marker giving rise to hygromycin resistance, or the selection may be accomplished by co-transformation, such as known in the art. See e.g., Published PCT Application WO 91/17243.

Intracellular expression may be advantageous in some respects, e.g., when using certain bacteria or fungi as host cells to produce large amounts of alpha-glucosidase for subsequent enrichment or purification. Alternatively, extracellular secretion of alpha-glucosidase into the culture medium can also be used to make a cultured cell material comprising the isolated alpha-glucosidase.

The procedures used to ligate the DNA construct encoding an alpha-glucosidase, the promoter, terminator and other elements, respectively, and to insert them into suitable vectors containing the information necessary for replication, are known to persons skilled in the art and readily available. See, e.g., Sambrook et al., MOLECULAR CLONING: A LABORATORY MANUAL, $2^{nd}$ ed., Cold Spring Harbor, 1989, and $3^{rd}$ ed., 2001.

3.2. Transformation and Culture of Host Cells

An isolated cell, either comprising a DNA construct or an expression vector, is advantageously used as a host cell in the recombinant production of an alpha-glucosidase. The cell may be transformed with the DNA construct encoding the enzyme, conveniently by integrating the DNA construct (in one or more copies) in the host chromosome. This integration is generally considered to be an advantage, as the DNA sequence is more likely to be stably maintained in the cell. Integration of the DNA constructs into the host chromosome may be performed according to conventional methods, e.g., by homologous or heterologous recombination. Alternatively, the cell may be transformed with an expression vector in connection with the different types of host cells.

Examples of suitable bacterial host organisms are Gram positive bacterial species such as Bacillaceae including *Bacillus subtilis, Bacillus licheniformis, Bacillus lentus, Bacillus brevis, Geobacillus* (formerly *Bacillus*) *stearothermophilus, Bacillus alkalophilus, Bacillus amyloliquefaciens, Bacillus coagulans, Bacillus lautus, Bacillus megaterium*, and *Bacillus thuringiensis; Streptomyces* species such as *Streptomyces murinus*; lactic acid bacterial species including *Lactococcus* sp. such as *Lactococcus lactis; Lactobacillus* sp. including *Lactobacillus reuteri; Leuconostoc* sp.; *Pediococcus* sp.; and *Streptococcus* sp. Alternatively, strains of a Gram negative bacterial species belonging to Enterobacteriaceae including *E. coli*, or to Pseudomonadaceae can be selected as the host organism.

A suitable yeast host organism can be selected from the biotechnologically relevant yeasts species such as but not limited to yeast species such as *Pichia* sp., *Hansenula* sp., or *Kluyveromyces, Yarrowinia, Schizosaccharomyces* species or a species of *Saccharomyces*, including *Saccharomyces cerevisiae* or a species belonging to *Schizosaccharomyces* such as, for example, *S. pombe* species. A strain of the methylotrophic yeast species, *Pichia pastoris*, can be used as the host organism. Alternatively, the host organism can be a *Hansenula* species. Suitable host organisms among filamentous fungi include species of *Aspergillus*, e.g., *Aspergillus niger, Aspergillus oryzae, Aspergillus tubigensis, Aspergillus awamori*, or *Aspergillus nidulans*. Alternatively, strains of a *Fusarium* species, e.g., *Fusarium oxysporum* or of a *Rhizomucor* species such as *Rhizomucor miehei* can be used as the host organism. Other suitable strains include *Thermomyces* and *Mucor* species. In addition, *Trichoderma* sp. can be used as a host. An alpha-glucosidase expressed by a fungal host cell can be glycosylated, i.e., will comprise a glycosyl moiety. The glycosylation pattern can be the same or different as present in the wild-type alpha-glucosidase. The type and/or degree of glycosylation may impart changes in enzymatic and/or biochemical properties.

It is advantageous to delete genes from expression hosts, where the gene deficiency can be cured by the transformed expression vector. Known methods may be used to obtain a fungal host cell having one or more inactivated genes. Gene inactivation may be accomplished by complete or partial deletion, by insertional inactivation or by any other means that renders a gene nonfunctional for its intended purpose, such that the gene is prevented from expression of a functional protein. In some instances, gene inactivation may be accomplished using siRNA methodologies. Any gene from a *Trichoderma* sp. or other filamentous fungal host that has been cloned can be deleted, for example, cbh1, cbh2, egl1, and egl2 genes. Gene deletion may be accomplished by inserting a form of the desired gene to be inactivated into a plasmid by methods known in the art.

Introduction of a DNA construct or vector into a host cell includes techniques such as transformation; electroporation; nuclear microinjection; transduction; transfection, e.g., lipofection mediated and DEAE-Dextrin mediated transfection; incubation with calcium phosphate DNA precipitate; high velocity bombardment with DNA-coated microprojectiles; and protoplast fusion. General transformation techniques are known in the art. See, e.g., Sambrook et al. (2001), supra. The expression of heterologous protein in *Trichoderma* is described, for example, in U.S. Pat. No. 6,022,725. Reference is also made to Cao et al. (2000) *Science* 9:991-1001 for transformation of *Aspergillus* strains. Genetically stable transformants can be constructed with vector systems whereby the nucleic acid encoding an alpha-glucosidase is stably integrated into a host cell chromosome. Transformants are then selected and purified by known techniques.

The preparation of *Trichoderma* sp. for transformation, for example, may involve the preparation of protoplasts from fungal mycelia. See Campbell et al. (1989) *Curr. Genet.* 16: 53-56. The mycelia can be obtained from germinated vegetative spores. The mycelia are treated with an enzyme that digests the cell wall, resulting in protoplasts. The protoplasts are protected by the presence of an osmotic stabilizer in the suspending medium. These stabilizers include sorbitol, mannitol, potassium chloride, magnesium sulfate, and the like. Usually the concentration of these stabilizers varies between 0.8 M and 1.2 M, e.g., a 1.2 M solution of sorbitol can be used in the suspension medium.

Uptake of DNA into the host *Trichoderma* sp. strain depends upon the calcium ion concentration. Generally, between about 10-50 mM $CaCl_2$ is used in an uptake solution. Additional suitable compounds include a buffering system, such as TE buffer (10 mM Tris, pH 7.4; 1 mM EDTA) or 10 mM MOPS, pH 6.0 and polyethylene glycol. The polyethylene glycol is believed to fuse the cell membranes, thus permitting the contents of the medium to be delivered into the cytoplasm of the *Trichoderma* sp. strain. This fusion frequently leaves multiple copies of the plasmid DNA integrated into the host chromosome.

Usually transformation of *Trichoderma* sp. uses protoplasts or cells that have been subjected to a permeability treatment, typically at a density of $10^5$ to $10^7$/mL, particularly $2\times10^6$/mL. A volume of 100 μL of these protoplasts or cells in an appropriate solution (e.g., 1.2 M sorbitol and 50 mM·$CaCl_2$) may be mixed with the desired DNA. Generally, a high concentration of PEG is added to the uptake solution. From 0.1 to 1 volume of 25% PEG 4000 can be added to the protoplast suspension; however, it is useful to add about 0.25 volumes to the protoplast suspension. Additives, such as dimethyl sulfoxide, heparin, spermidine, potassium chloride and the like, may also be added to the uptake solution to facilitate transformation. Similar procedures are available for other fungal host cells. See, e.g., U.S. Pat. No. 6,022,725.

3.3. Expression

A method of producing an alpha-glucosidase may comprise cultivating a host cell under conditions conducive to the production of the enzyme and recovering the enzyme from the cells and/or culture medium.

The medium used to cultivate the cells may be any conventional medium suitable for growing the host cell and obtaining expression of an alpha-glucosidase polypeptide. Suitable media and media components are available from commercial suppliers or may be prepared according to published recipes (e.g., as described in catalogues of the American Type Culture Collection).

An alpha-glucosidase polypeptide secreted from the host cells can be used, with minimal post-production processing, as a whole broth preparation. In some embodiments, the preparation of a spent whole fermentation broth of a recombinant microorganism can be achieved using any cultivation method known in the art resulting in the expression of an alpha-glucosidase of interest. Fermentation may, therefore, be understood as comprising shake flask cultivation, small- or large-scale fermentation (including continuous, batch, fed-batch, or solid state fermentations) in laboratory or industrial fermenters performed in a suitable medium and under conditions allowing the alpha-glucosidase to be expressed or isolated. The term "spent whole fermentation broth" is defined herein as unfractionated contents of fermentation material that includes culture medium, extracellular proteins (e.g., enzymes), and cellular biomass. It is understood that the term "spent whole fermentation broth" also encompasses cellular biomass that has been lysed or permeabilized using methods well known in the art.

Host cells may be cultured under suitable conditions that allow expression of an alpha-glucosidase. Expression of the enzymes may be constitutive such that they are continually produced, or inducible, requiring a stimulus to initiate expression. In the case of inducible expression, protein production can be initiated when required by, for example, addition of an inducer substance to the culture medium, for example dexamethasone or IPTG or sophorose. Polypeptides can also be produced recombinantly in an in vitro cell-free system, such as the TNT™ (Promega) rabbit reticulocyte system.

An expression host also can be cultured in the appropriate medium for the host, under aerobic conditions. Shaking or a combination of agitation and aeration can be provided, with production occurring at the appropriate temperature for that host, e.g., from about 25° C. to about 75° C. (e.g., 30° C. to 45° C.), depending on the needs of the host and production of the desired alpha-glucosidase. Culturing can occur from about 12 to about 100 hours or greater (and any hour value there between, e.g., from 24 to 72 hours). Typically, the culture broth is at a pH of about 4.0 to about 8.0, again depending on the culture conditions needed for the host relative to production of an alpha-glucosidase.

3.4. Fermentation

Any of the fermentation methods well known in the art can suitably used to ferment the transformed or the derivative fungal strain as described above. In some embodiments, fungal cells are grown under batch or continuous fermentation conditions.

A classical batch fermentation is a closed system, where the composition of the medium is set at the beginning of the fermentation, and the composition is not altered during the fermentation. At the beginning of the fermentation, the medium is inoculated with the desired organism(s). In other words, the entire fermentation process takes place without addition of any components to the fermentation system throughout.

Alternatively, a batch fermentation qualifies as a "batch" with respect to the addition of the carbon source. Moreover, attempts are often made to control factors such as pH and oxygen concentration throughout the fermentation process. Typically the metabolite and biomass compositions of the batch system change constantly up to the time the fermentation is stopped. Within batch cultures, cells progress through a static lag phase to a high growth log phase and finally to a stationary phase, where growth rate is diminished or halted. Left untreated, cells in the stationary phase would eventually die. In general, cells in log phase are responsible for the bulk of production of product.

A suitable variation on the standard batch system is the "fed-batch fermentation" system. In this variation of a typical batch system, the substrate is added in increments as the fermentation progresses. Fed-batch systems are useful when it is known that catabolite repression would inhibit the metabolism of the cells, and/or where it is desirable to have limited amounts of substrates in the fermentation medium. Measurement of the actual substrate concentration in fed-batch systems is difficult and is therefore estimated on the basis of the changes of measurable factors, such as pH, dissolved oxygen and the partial pressure of waste gases, such as CO2. Batch and fed-batch fermentations are well known in the art.

Continuous fermentation is another known method of fermentation. It is an open system where a defined fermentation medium is added continuously to a bioreactor, and an equal amount of conditioned medium is removed simultaneously for processing. Continuous fermentation generally maintains the cultures at a constant density, where cells are maintained primarily in log phase growth. Continuous fermentation allows for the modulation of one or more factors that affect cell growth and/or product concentration. For example, a limiting nutrient, such as the carbon source or nitrogen source, can be maintained at a fixed rate and all other parameters are allowed to moderate. In other systems, a number of factors affecting growth can be altered continuously while the cell concentration, measured by media turbidity, is kept constant. Continuous systems strive to maintain steady state growth conditions. Thus, cell loss due to medium being drawn off should be balanced against the cell growth rate in the fermentation. Methods of modulating nutrients and growth factors for continuous fermentation processes, as well as techniques for maximizing the rate of product formation, are well known in the art of industrial microbiology.

3.5. Methods for Enriching and Purification

Separation and concentration techniques are known in the art and conventional methods can be used to prepare a concentrated solution or broth comprising an alpha-glucosidase polypeptide of the invention.

After fermentation, a fermentation broth is obtained, the microbial cells and various suspended solids, including residual raw fermentation materials, are removed by conventional separation techniques in order to obtain an alpha-glucosidase solution. Filtration, centrifugation, microfiltration, rotary vacuum drum filtration, ultrafiltration, centrifugation followed by ultrafiltration, extraction, or chromatography, or the like, are generally used.

It may at times be desirable to concentrate a solution or broth comprising an alpha-glucosidase polypeptide to optimize recovery. Use of un-concentrated solutions or broth would typically increase incubation time in order to collect the enriched or purified enzyme precipitate.

The enzyme-containing solution can be concentrated using conventional concentration techniques until the desired enzyme level is obtained. Concentration of the enzyme containing solution may be achieved by any of the techniques discussed herein. Examples of methods of enrichment and purification include but are not limited to rotary vacuum filtration and/or ultrafiltration.

The alpha-glucosidase-containing solution or broth may be concentrated until such time the enzyme activity of the concentrated alpha-glucosidase polypeptide-containing solution or broth is at a desired level.

Concentration may be performed using, e.g., a precipitation agent, such as a metal halide precipitation agent. Metal halide precipitation agents include but are not limited to alkali metal chlorides, alkali metal bromides and blends of two or more of these metal halides. Exemplary metal halides include sodium chloride, potassium chloride, sodium bromide, potassium bromide and blends of two or more of these metal halides. The metal halide precipitation agent, sodium chloride, can also be used as a preservative.

The metal halide precipitation agent is used in an amount effective to precipitate an alpha-glucosidase. The selection of at least an effective amount and an optimum amount of metal halide effective to cause precipitation of the enzyme, as well as the conditions of the precipitation for maximum recovery including incubation time, pH, temperature and concentration of enzyme, will be readily apparent to one of ordinary skill in the art, after routine testing.

Generally, at least about 5% w/v (weight/volume) to about 25% w/v of metal halide is added to the concentrated enzyme solution, and usually at least 8% w/v. Generally, no more than about 25% w/v of metal halide is added to the concentrated enzyme solution and usually no more than about 20% w/v. The optimal concentration of the metal halide precipitation agent will depend, among others, on the nature of the specific alpha-glucosidase polypeptide and on its concentration in the concentrated enzyme solution.

Another alternative way to precipitate the enzyme is to use organic compounds. Examples of organic compound precipitating agents include: 4-hydroxybenzoic acid, alkali metal salts of 4-hydroxybenzoic acid, alkyl esters of 4-hydroxybenzoic acid, and blends of two or more of these organic compounds. The addition of the organic compound precipitation agents can take place prior to, simultaneously with or subsequent to the addition of the metal halide precipitation agent, and the addition of both precipitation agents, organic compound and metal halide, may be carried out sequentially or simultaneously.

Generally, the organic precipitation agents may be selected from alkali metal salts of 4-hydroxybenzoic acid, such as sodium or potassium salts, and linear or branched alkyl esters of 4-hydroxybenzoic acid, wherein the alkyl group contains from 1 to 12 carbon atoms, or blends of two or more of these organic compounds. The organic compound precipitation agents may be, for example, linear or branched alkyl esters of 4-hydroxybenzoic acid, wherein the alkyl group contains from 1 to 10 carbon atoms, or blends of two or more of these organic compounds. Examples of organic compounds are linear alkyl esters of 4-hydroxybenzoic acid, wherein the alkyl group contains from 1 to 6 carbon atoms, and blends of two or more of these organic compounds. Methyl esters of 4-hydroxybenzoic acid, propyl esters of 4-hydroxybenzoic acid, butyl ester of 4-hydroxybenzoic acid, ethyl ester of 4-hydroxybenzoic acid and blends of two or more of these organic compounds can also be used. Additional suitable organic compounds may include but are not limited to 4-hydroxybenzoic acid methyl ester (named methyl PARABEN), or 4-hydroxybenzoic acid propyl ester (named propyl PARABEN), either can be used as alpha-glucosidase preservative agents. For further descriptions, see, e.g., U.S. Pat. No. 5,281,526.

Addition of the organic compound precipitation agent may provide the advantage of high flexibility of the precipitation conditions with respect to pH, temperature, alpha-glucosidase concentration, precipitation agent concentration, or time of incubation.

The organic compound precipitation agent is used in an amount effective to improve precipitation of the enzyme by means of the metal halide precipitation agent. The selection of at least an effective amount and an optimum amount of organic compound precipitation agent, as well as the conditions of the precipitation for maximum recovery including incubation time, pH, temperature and concentration of enzyme, will be readily apparent to one of ordinary skill in the art, in light of the present disclosure, after routine testing.

Generally, at least about 0.01% w/v of organic compound precipitation agent is added to the concentrated enzyme solution and usually at least about 0.02% w/v. Generally, no more than about 0.3% w/v of organic compound precipitation agent is added to the concentrated enzyme solution and usually no more than about 0.2% w/v.

The concentrated polypeptide solution, containing the metal halide precipitation agent, and the organic compound precipitation agent, can be adjusted to a pH, which will, of necessity, depend on the enzyme to be enriched or purified. Generally, the pH is adjusted at a level near the isoelectric point of the alpha-glucosidase. The pH can be adjusted at a pH in a range from about 2.5 pH units below the isoelectric point (pI) up to about 2.5 pH units above the isoelectric point.

The incubation time necessary to obtain an enriched or purified enzyme precipitate depends on the nature of the specific enzyme, the concentration of enzyme, and the specific precipitation agent(s) and its (their) concentration. Generally, the time effective to precipitate the enzyme is between about 1 to about 30 hours; usually it does not exceed about 25 hours. In the presence of the organic compound precipitation agent, the time of incubation can still be reduced to less about 10 hours and in most cases even about 6 hours.

Generally, the temperature during incubation is maintained between about 4° C. and about 50° C.

The overall recovery of enriched or purified enzyme precipitate, and the efficiency with which the process is conducted, is improved by agitating the solution comprising the enzyme, the added metal halide and the added organic compound. The agitation step is done both during addition of the metal halide and the organic compound, and during the subsequent incubation period. Suitable agitation methods include mechanical stirring or shaking, vigorous aeration, or any similar technique.

After the incubation period, the enriched or purified enzyme can then be separated from the dissociated pigment and other impurities and collected by conventional separation techniques, such as filtration, centrifugation, microfiltration, rotary vacuum filtration, ultrafiltration, press filtration, cross membrane microfiltration, cross flow membrane microfiltration, or the like. Further enrichment or purification of the enzyme precipitate can be obtained by washing the precipitate with water.

For production scale recovery, alpha-glucosidase polypeptides can be enriched or partially purified as generally described above by removing cells via flocculation with polymers. Alternatively, the enzyme can be enriched or purified by microfiltration followed by concentration by ultrafiltration using available membranes and equipment. However, for some applications, the enzyme does not need to be enriched or purified, and whole broth culture can be lysed and used without further treatment. The enzyme can then be processed, for example, into granules.

4. Composition

It is an object of the present disclosure to provide a starch or oligosaccharide degradation composition in the presence of an alpha-glucosidase polypeptide isolated, derived or derivable from *Rasamsonia* or an engineered variant of alpha glucosidase isolated, derived or derivable from a *Rasamsonia* homolog.

In one aspect, the present disclosure provides a composition comprising a polypeptide having alpha-glucosidase activity that is isolated, derived or derivable from a *Rasamsonia*, or a *Rasamsonia* homolog, wherein the polypeptide comprises an amino acid sequence that is (1) SEQ ID NO:3 or 7; (2) at least about 70% identical to SEQ ID NO:3 or 7 or to a fragment thereof that is at least 500 contiguous amino acid residues or longer, and at least one other starch or oligosaccharide degradation enzyme.

Such other starch or oligosaccharide degradation enzymes may be an alpha-amylase, a beta-amylase, a glucoamylase (or amyloglucosidase), a pullulanase, an isoamylase, a different alpha-glucosidase, a cyclodextrin glycosyltransferase, or a combination of one or more of the above.

Alpha-amylases are a well-known class of enzymes involved in starch degradation. Alpha-amylases are also called alpha-1,4-glucan-4-glucanohydrolases, falling within E.C. 3.2.1.1. They are known to catalyze the hydrolysis of starch and other linear and branched 1,4-glucosidic oligo- and polysaccharides. Alpha-amylases can be derived from a wide selection of organisms including bacteria, such as from species of the genus *Bacillus*, e.g., *Bacillus licheniformis*; from species of fungi, such as *Aspergillus niger* or *Aspergillus oryzae*, from plants such as barley or other grains, and from animals such as various mammals. The three dimensional structures of the alpha-amylases are well studied and understood. These enzymes comprise three distinct domains or regions of polypeptides that form substructures within the same alpha-amylase molecules. See, e.g., Machius et al. (1995) J. Mol. Biol. 246:545-559. For the purpose of the present disclosure, alpha-amylases include enzymes that are capable of catalyzing the hydrolysis of starch and other linear and branched 1,4-glucosidic oligo- and polysaccharides. In some embodiments, suitable alpha amylases may be polypeptides comprising an amino acid sequence that is at least 60% identical to that of the alpha-amylase of *Bacillus licheniformis, Aspergillus niger*, or *Aspergillus oryzae*, which polypeptides comprise the same three distinct domains or regions of polypeptides that form substructures within the same amylase molecules according to Machius et al. (supra).

Glucoamylases are another class of well-studied starch degradation enzymes, and more specifically exo-acting carbohydrolases. They are also called glucan 1,4-alpha-glucohydrolases, and belong to EC 3.2.1.3. They catalyze the hydrolyses and removal of successive glucose units from the non-reducing ends of starch or related oligo- and polysaccharide molecules, linear or branched, such as amylose and amylopectins. Glucoamylases can be derived from bacterial, fungal, yeast, or plant sources. When they are sourced from fungi, especially filamentous fungi, for example, *Aspergillus*, they are extracellularly produced. See, e.g., Svensson et al. (1983) Carlsberg Res. Commun. 48:529-544; Boel et al., (1984) EMBO J. 3:1097-1102. Same were found from other filamentous fungi, such as *Talaromyces* (U.S. Pat. Nos. 4,247,637; 6,255,084 and 6,620,924); *Rhizopus* (Ashikari et al., (1986) Agric. Biol. Chem. 50:957-964; Ashikari et al., (1989) App. Microbiol. and Biotech. 32:129-133 and U.S. Pat. No. 4,863,864); *Humicola* (WO 05/052148 and U.S. Pat. No. 4,618,579) and *Mucor* (Houghton-Larsen et al., (2003) Appl. Microbiol. Biotechnol. 62:210-217). For the purpose of the present disclosure, glucoamylases include enzymes that are capable of catalyzing the hydrolyses and removal of successive glucose units from the non-reducing ends of starch or molecules such as amylose and amylopectins. In some embodiments, suitable glucoamylases may be polypeptides comprising an amino acid sequence that is at least about 70% (e.g., at least about 70%, at least about 75%, at least 80%, at least 85%, at least 90% or higher) identical to that of the glucoamylase of *Aspergillus, Talaromyces, Rhizopus, Humicola* or *Mucor.*

Pullulanases are an amylolytic endoenzyme that degrades pullulan. They fall within the category of glucanases and EC 3.2.1.41, also known as pullulan-6-glucanohydrolase (debranching enzyme). More specifically pullulanases hydrolytically cleave pullulan alpha-glucan polysaccharides, a chain of maltotriose units linked by alpha-1,6-glucosidic bonds, It can be derived, for example, extracellularly, as cell surface-anchored lipoprotein by Gram-negative bacteria of the genus *Klebsiella*. Gram-positive bacteria produce pullulanases as secreted proteins. Type I pullulanases have specificity towards alpha-1,6-linkages. Type II pullulanases also have capability to hydrolyze alpha 1,4-linkages. It can also be derived from other bacteria and archaea. In some embodiments, suitable pullulanases may be a Type I or Type II pullulanase comprising an amino acid sequence that is at least about 80% (at least 80%, at least 85%, at least 90% or higher) identical to that of the pullulanase of *Klebsiella, Bacillus* or an archaea.

Isoamylases are debranching enzymes of E.C. 3.2.1.68. They catalyze the (sometimes partial) hydrolysis of 1,6-alpha-linkages in amylopectin, glycogen, and beta-limit dextrins into branched and linear oligosaccharides that results in the formation of alpha-limit dextrins. They prefer amylopectin and glycogen as substrates, much more than pullulan. Isoamylases can be derived from various microbial sources, including bacteria such as, for example, *Bacillus, Streptococcus, Streptomyces, Staphylococcus, Enterococcus, Lactobacillus, Lactococcus, Clostridium, Geobacillus, Oceanobacillus Dyella, Fulvimonas, Frateuria and Rhodanobacter, E. coli, Pseudomonas, Salmonella, Campylobacter, Helicobacter, Flavobacterium, Fusobacterium, Ilyobacter, Neisseria*, or *Ureaplasma*. In some embodiments, suitable isoamylase may comprise an amino acid sequence that is at last about 60% (at least about 60%, at least about 65%, at least about 70%, at least about 75%, at least 80%, at least 85%, at least 90% or higher) identical to that of the isoamylases of a *Bacillus, Streptococcus, Streptomyces, Staphylococcus, Enterococcus, Lactobacillus, Lactococcus, Clostridium, Geobacillus, Oceanobacillus Dyella, Fulvimonas, Frateuria and Rhodanobacter, E. coli, Pseudomonas, Salmonella, Campylobacter, Helicobacter, Flavobacterium, Fusobacterium, Ilyobacter, Neisseria*, or *Ureaplasma*.

Cyclodextrin glycosyltransferases are also called cyclodextrin glucanotransferase or CGTase, falling within E.C. 2.3.1.19. They catalyze a number of reactions with the most important one being the synthesis of non-reducing cyclic destrins known as cyclodextrins starting from starch, amylose and other polysaccharides. They are most commonly sourced from bacteria, for example, a number of *Bacillus* species. In some embodiments, a suitable cyclodextrin glycosyltransferase is one comprising an amino acid sequence that is at least about 70% (e.g., at least about 70%, at least about 75%, at least about 80%, at least about 85%, at least about 90% or higher) identical to a cyclodextrin glycosyltransferase of a *Bacillus*.

In some embodiments, the composition comprises an alpha-glucosidase polypeptide isolated, derived or derivable from *Rasamsonia* or an engineered variant thereof, and one or more of starch or oligosaccharide degradation enzymes selected from an alpha-amylase, a beta-amylase, a glucoamylase, an amyloglucosidase, a pullulanase, an isoamylase, an alpha-glucosidase, or an cyclodextrin glycosyltransferase, wherein at least one of the one or more starch or oligosaccharide degradation enzyme is from a different organism as the alpha-glucosidase (i.e., is heterologous to the alpha-glucosidase). In certain embodiments, the starch or oligosaccharide degradation enzyme of the composition is from a microorganism that is not a *Rasamsonia* species.

The above composition of the disclosure is suitable for use in a process for producing fermentation products, such as ethanol. In one embodiment, the composition is used in a process for producing fermentation products in addition to a carbohydrate-source generating enzyme and an alpha-amylase, preferably a glucoamylase and an acid alpha-amylase, respectively. The carbohydrate-source generating enzyme may be any carbohydrate-source generating enzyme.

In certain embodiment the carbohydrate-source generating enzyme is a glucoamylase derived from a strain of *Aspergillus*, for example, *Aspergillus niger* or *Aspergillus awamori*; a strain of *Talaromyces*, for example *Talaromyces emersonii*; or a strain of *Athelia*, for example *Athelia rolfsii*; a strain of *Trametes*, for example, *Trametes cingulata*; a strain of the genus *Pachykytospora*, for example a strain of *Pachykytospora papyracea*; or a strain of the genus *Leucopaxillus*, for example *Leucopaxillus giganteus*; or a strain of the genus *Peniophora*, for example a strain of the species *Peniophora rufomarginata*; or a mixture of one or more thereof.

In some embodiments, the carbohydrate-source generating enzyme is an alpha-amylase. For example the alpha-amylase is suitably an acid alpha-amylase, and particularly an acid fungal alpha-amylase. In another example, the alpha-amylase may be a fungal alpha-amylase. For example, the alpha-amylase is suitably derived from the genus *Aspergillus*, such as a strain of *Aspergillus niger, Aspergillus oryzae, Aspergillus awamori*, or *Aspergillus kawachii*; or of the genus *Rhizomucor*, such as a strain of *Rhizomucor pusillus*; or the genus *Meripilus*, such as a strain of *Meripilus giganteus*; or the genus *Bacillus*, such as a strain of *Bacillus stearothermophilus*.

In particular embodiments, several types of cells expressing various carbohydrate-source generating enzymes may be used together or sequentially to degrade different kinds of oligosaccharide contained in the same oligosaccharide substrate. The oligosaccharide substrate can be placed in contact with a culture medium containing the cells, glucose or the like as a carbon source, as well as a nitrogen source by the cells, including an organic nitrogen source (e.g., peptone, meat extract, yeast extract, corn steep liquor) or an inorganic nitrogen source (e.g., ammonium sulfate, ammonium chloride). If necessary, the culture medium may further contain inorganic salts (e.g., sodium ion, potassium ion, calcium ion, magnesium ion, sulfate ion, chlorine ion, phosphate ion). Moreover, the medium may also be supplemented with trace components such as vitamins, oligo-elements and amino acids.

The compositions of the present disclosure can suitably and readily be prepared in accordance with methods known in the art. The compositions of interest comprising an alpha-glucosidase polypeptide of the invention can be a liquid or a solid composition.

5. Use of the Composition Thus Made

The present disclosure is also related to methods for using the composition comprising a polypeptide of the invention having alpha-glucosidase activity.

The composition can be used to produce fermented malt drinks, e.g., (low-caloric) beer, according to a method described in, for example, published PCT application WO 2002/55652. Fermented malt beverages with reinforced filling taste and fullness of mouthfeel can be produced by addition of a polypeptide having alpha-glucosidase activity prior to heat treatment in a wort production process in the course of manufacturing fermented malt beverages. Low-calorie beers can be manufactured in which a polypeptide having alpha-glucosidase activity is added in the fermentation process in the brewing of beer.

In one example, the method of use relates to the production of a fermented malt beverage, wherein a polypeptide having alpha-glucosidase activity of the present disclosure is added prior to heat treatment of wort in a wort production process.

The composition of the present disclosure may also be used in grain procession or production of alcohol from cereal grains according to the method described in a published patent application DE 2944483. A variety of enzymes are able to catalyze starch hydrolysis, and can be used in the production of fermentation products, such as ethanol, from starch-containing material. Generally there are two distinct approaches. The most commonly used process, often referred to as a "conventional process", includes liquefying gelatinized starch at high temperature using typically a bacterial alpha-amylase, followed by simultaneous saccharification and fermentation carried out in the presence of a glucoamylase and a fermenting organism. The other process, also known, is often referred to as a "raw starch hydrolysis"-process (RSH process), which includes simultaneously saccharifying and fermenting granular starch below the initial gelatinization temperature typically in the presence of an acid fungal alpha-amylase and a glucoamylase. An alpha-glucosidase can suitably be used in either of these processes for producing fermentation products from starch-containing material.

The composition thus made can likewise be used in food applications. A number of enzymes are used in bakery, cheese making, starch processing and production of fruit juices and other drinks, providing benefits such as improved texture, appearance and nutritional value, generate desirable flavors and aromas, and the like. Some methods and agents of improving the quality of a starch-containing food have been mentioned in the art in order that the degradation of the starch-containing food is suppressed and the quality of thereof can be maintained for long periods of time. An alpha-glucosidase polypeptide and/or a composition comprising such a polypeptide, with or without other enzymes, can be useful in such applications.

In one example, enzymes are used in cooked rice, and an alpha-glucosidase polypeptide of the invention can be included in this use. There has been disclosed a method of improvement of cooked rice where polished rice is mixed with enzymes such as amylase, protease and lipase, salt and cyclodextrin followed by boiling (see, published Japanese Patent No. 58-86050); a method for the suppression of retrogradation of cooked rice where an aqueous solution of a saccharified type amylase (beta-amylase, glucoamylase) is sprayed onto rice after cooking (see, published Japanese Patent No. 60-199355); a composition for improvement of cooked rice containing cyclodextrin, one or more members of amylolytic enzymes, proteinases and cellulases, emulsifiers and water-soluble gelatin (see, published Japanese Patent No. 59-2664). An alpha-glucosidase can be suitably incorporated in such methods to further enhance the beneficial effects.

In another example, the alpha-glucosidase polypeptides of the invention can be used in conjunction with other enzymes in baking applications. When time passes after baking, an inner part of the bread becomes hard and dry in texture. This change in the bread is referred to as retrogradation of bread. Many methods have been investigated to modify the formulations by adding an emulsifier or an enzyme, such as amylase, or by increasing the amounts of sugar, fat/oil or water in manufacturing bread.

In order to simplify the process of the manufacture of bread, frozen dough has been widely used in recent years. However, the thawed dough becomes soft due to growth of ice crystals, production of carbon dioxide, etc. during freezing storage and, further, the generation of gas lowers due to the death of yeast. Therefore, when bread is manufactured using such dough, problems such as a decrease in volume and a promotion of retrogradation occur. With regard to an improving agent without emulsifier, there has been disclosed that an improving agent containing a maltotriose productive enzyme or hemicellulase is used for frozen dough (see, Japanese Patent Laid-Open No. 07-322811). An alpha-glucosidase polypeptide of the present disclosure can suitably be incorporated into such a process to help prevent retrogradation.

In yet another example, alpha-glucosidase polypeptides of the invention can be used in conjunction with other enzymes in noodle manufacture. It is noted that noodles are generally prepared by cooking raw noodles. Generally, it is demanded that those noodles have adequate hardness, elasticity, toughness and smoothness (slippery feel) after being cooked, have good texture with a good slippery smoothness through the throat and cannot be softened by hot water or by boiling. There exists a published patent application describing the use of an alpha-glucosidase having a saccharide transferring activity, which converts an alpha-1,4-bond to an alpha-1,6-bond, in noodle manufacture. See, published PCT application WO2005096839.

The present disclosure is further described by the following examples which should not be construed as limiting the scope of the disclosure.

EXAMPLES

Aspects of the present methods and compositions may be further understood in light of the following examples, which should not be construed as limiting. Modifications to materials and methods will be apparent to those skilled in the art.

Example 1

Synthesis of TauSec098 Gene

A first polypeptide sequence of SEQ ID NO:3 was identified to potentially encoding an alpha-glucosidase. This polypeptide was named TauSec098, Annotation of SEQ ID NO:3 indicated that this enzyme most likely belongs to Glycosyl hydrolases family 31 and contains a CBM_20 domain at its N-terminal based on the PFAM search (http://pfam.sanger.ac.uk/).

It was noted that, at the N-terminus, the protein has a signal peptide with a length of 22 amino acids as predicted by SignalP version 4.0 (Nordahl Petersen et al. (2011) Nature Methods, 8:785-786). The presence of a signal sequence suggested that TauSec098 is a secreted enzyme.

The nucleotide sequence of the TauSec098 gene is set forth as SEQ ID NO: 1. The predicted signal sequence is shown in italics and lowercase.

atgcggccaacttccctcgtcaagcacttggctgcgaccagcctcctctt
tctcgcggcggatgcaGCTGCTATCGTCCGCCGCAACGGCGCCTCTCCTT
CATGCCCCGGCTATAAAGCGAGTAACGTGAAGACCGTCGACGGTGAAATC
GTCAGCGCGGATCTCAATCTCGCGGGTCCCGCCTGCAATGTGTATGGCAC
GGATCTGGACGATCTGAAGCTGCAGGTTGAGTACCAATCAGGTAAGTCGC
ACAGCATCGCCGTCTGCAGCTTATCGGCAGCATGTGATCGGCGCCTGGAC
TAGGGCTTAGGGCCTGGGGTTAGGGCTGACTGCTTGCTGCCGTTCGATGT
GACTGGAACTGTACGGTTGGTTGACAACGATCTGACATCTGCAGAACAAC
GCCTCCATGTGAAGATCTACGATGCCGCCGAGCAGGTCTACCAGGTGCCC
ACCGCGGTGCTTCCCCGGCCCAGCAGCGCCAACATCCCCCCGGCCAAGTC
GGACCTGAAGTTCTCCATGACCAACGACCCCTTCTCCTTTACCATCAAGC
GCAGATCAAACGGCGAAATCCTCTTCGACACCTCCGGCCATCCGCTGATC
TTCGAGTCGCAGTATCTGGGCCTCCGTACCAAGCTGCCGGACTCGCCCAA
CATCTACGGCCTGGGAGAGCACACCGGTTCTTTCCGCCTGCCCACCAAGA
ATTACACCCGCACGCTGTGGTCGCGCGATGCGTACGGTACGCCCAAAGAC
ACCAACCTGTACGGCAACCACCCGGTGTACTTCGACTACGCGGCAGCAA
CGGCACCCATGGCGTGTTCCTGCTGAACAGCAACGGCATGGACGTCGATA
TCGACGTCGACTCGGACGGACAGTACCTGCAGTACAACACCCTGGGGGGC
GTGCTGGACTTCTACTTCCTCAGCGGGCCGGATCCCAAGGCCGTCGCGAC
GCAGTATGCCGAGACGGTCGGAAAACCGGTCATGATGCCCTACTGGGGAT
TCGGCTTCCACAACTGCAGATATGGATACCAGGACATCTATGAGGTTGCT
GAGATCATTGCCAACTACAGTGCCGCAAACATTCCGCTTGAGACCCAATG
GACTGATATCGGTATGCTTTCCATCCCGGTGCCGTGGTTTTTGCTTCTCA
GCGTGGCTGACTGTTGCAGACTATATGGATCTGAGGAAAGTGTTTACGCT
GGACCCCTATCGCTATCCATTGAAGCTCGTCCAAGAGGTTGTCTCTTATC
TCCACAAGCACAACCAGCACTACATCATGATGGTGGACCCTGCAGTGGCA
TACCAGAACTATTCAGCGTTCAACAACGGCGTCGCTGCCGACGCTTTCCT
GAAGTTCTCGAATGGCTCCATCTACCAGGGTGTCGTCTGGCCGGGGCCGA
CGGCGTTCCCGGACTGGTTCGCACCCCAGACACAGGAGTTTTGGAATAGC
GAGTTCTCGACCTTCTTTGACCCCGCCCACGGCGTCGACATCGATGCCCT
TTGGATCGACATGAACGAGGCGTCCAACTTCTGCGACTTTCCCTGCTCGA
ACCCCGCCGCGTATGCGGCAGCCAACGGCGATCCGCCCACGCCTCCGCCG
GTCCGCTTGAGCCCCCGAGGCCGATTCCTGGATTTGGCCCTGACTTCCA
GCCGACGTGTGTCGCCACGGTGTCGTTCGATTGCGATGCGCAGACCTACT
TTGGCGAGAACATCCTCATCCTGGGTAACTCGACGACACTGGGAGCCGGC
GACGTTCACATGGCGCCAGTCATGAGCGCGAACAACTACCCGATCTGGCA
GCTGACCGTCCAGATGCCGCCGAATGGGACGTTCTCGTACCAGTACGTTC
GCAAGGAATCGGACGGCAGTTACATCTACGAACAGACGAATCGCACGGTC
ACGACGGGCGACTGCACCAGCGGCACGCTTAAGGTGTCCGACACCATCAC
CACCAGCTCTGGACCGCACAAGAGATCCGAATTACGGCCGCTGGTGCGCT
CGCCGTTCCCGGCGGAGGACCTGACCAGGCGCCAGTCTGGATCGATGTTG GGCCTGCCCAACAGGAACCTGCTGAATCCGCCATACACCATCCACAATGC
GGCTGGCAACCTGAGTGAGAAGACCATCAACACCGACCTGATCCATGCGG
GCGGATATGCCGAGTACGACACGCACAACTTGTACGGCACGATGATGAGC
GCGACCAGCAGGGAGGCGATGCTGAACCGCAGACCAGCAGTCAGGCCACT
TGTGTAAGTCATCCATCGTCCTTAAGCCAGACACAGCATGTTAGGGGCTA
ACGGGCAGTAGCATTACCCGGTCGACCTTCGCTGGAGCCGGCCGACAGGT
CGGCCACTGGCTCGGCGACAATTTCGCCGATTGGGACCACTACCGGTGGA
CGATCGCCGAGCTGCAGGAATTCGCGGCGCTGTTCCAGATCCCGATGGTC
GGCAGCGACATCTGCGGGTACGACGGCAACACGACGGACAACCTGTGCTC
GCGCTGGGTCTTCCTCGGCGCCTTCTCGCCCTTCTTCCGCGACCACTCGG
ACAACCAGTCGCCGCCGCACGAGCTGTACCGCACTCCGCAGATCGCGGCG
GCCGCGCGCGCCGCCATCGACATCCGCTACCGTCTGCTCGACTACGCGTA
CACGGTGCTGTGGACGCAGACCCAGACCGGCGCGCCGATGCTCAACCCCA
TGTTCTTCGAGTACCCGGCCGACAGCAACACCGCCGACCTGCAGTACCAG
TTCTTCTGGGGCGACAGCATCATGGTCGCGCCCGTGACCGACAACGACTC
GACCACCGTCAACGTCTACTTCCCGAAGGACCAGTTCTACGACTTCTACA
CCGGCGCACCTGTGTCCGGGGAGGGCAATACCGTCACCCTGACCGACGTC
GGCTTCGACACCATCCCGCTGTACTTCAAGGGCGGGAGCATCGTGCCCAT
GCGCGTGCGCTCGGCGAACACGACGGCGGAGCTGCGGCAGCAGGACTTCG
TCGTCGTCATCGCCCCGGACAGCCACGGCGACGCGACGGGCCAGCTGTAC
CTCGACGACGGCGAGAGCATCAACCAGCCGCACACCAGCGAGATCCAGTT
CTCGTACCGCGGAGGCCATTTCAGCATGACAGGCAAGTTTGACTATGATC
CCGGCAACGTGGTCATCAGCCAGATCACGCTGCTGGGTGCGGACGGCGCC
GGTAAAGGGGGTTCGTATAACAGCACCACCAAGGTGGCGACCTACAAAGT
CAACGCGAAGTTGACGGGTAAATTCGAAGCCAGCTTACACTAA The DNA coding sequence of the predicted mature form of TauSec098 is set forth as SEQ ID NO: 2.

GCTGCTATCGTCCGCCGCAACGGCGCCTCTCCTTCATGCCCCGGCTATAA
AGCGAGTAACGTGAAGACCGTCGACGGTGAAATCGTCAGCGCGGATCTCA
ATCTCGCGGGTCCCGCCTGCAATGTGTATGGCACGGATCTGGACGATCTG
AAGCTGCAGGTTGAGTACCAATCAGGTAAGTCGCACAGCATCGCCGTCTG
CAGCTTATCGGCAGCATGTGATCGGCGCCTGGACTAGGGCTTAGGGCCTG
GGGTTAGGGCTGACTGCTTGCTGCCGTTCGATGTGACTGGAACTGTACGG
TTGGTTGACAACGATCTGACATCTGCAGAACAACGCCTCCATGTGAAGAT
CTACGATGCCGCCGAGCAGGTCTACCAGGTGCCCACCGCGGTGCTTCCCC
GGCCCAGCAGCGCCAACATCCCCCCGGCCAAGTCGGACCTGAAGTTCTCC
ATGACCAACGACCCCTTCTCCTTTACCATCAAGCGCAGATCAAACGGCGA
AATCCTCTTCGACACCTCCGGCCATCCGCTGATCTTCGAGTCGCAGTATC
TGGGCCTCCGTACCAAGCTGCCGGACTCGCCCAACATCTACGGCCTGGGA
GAGCACACCGGTTCTTTCCGCCTGCCCACCAAGAATTACACCCGCACGCT

-continued

```
GTGGTCGCGCGATGCGTACGGTACGCCCAAAGACACCAACCTGTACGGCA
ACCACCCGGTGTACTTCGACTACCGCGGCAGCAACGGCACCCATGGCGTG
TTCCTGCTGAACAGCAACGGCATGGACGTCGATATCGACGTCGACTCGGA
CGGACAGTACCTGCAGTACAACACCCTGGGGGCGTGCTGGACTTCTACT
TCCTCAGCGGGCCGGATCCCAAGGCCGTCGCGACGCAGTATGCCGAGACG
GTCGGAAAACCGGTCATGATGCCCTACTGGGGATTCGGCTTCCACAACTG
CAGATATGGATACCAGGACATCTATGAGGTTGCTGAGATCATTGCCAACT
ACAGTGCCGCAAACATTCCGCTTGAGACCCAATGGACTGATATCGGTATG
CTTTCCATCCCGGTGCCGTGGTTTTTGCTTCTCAGCGTGGCTGACTGTTG
CAGACTATATGGATCTGAGGAAAGTGTTTACGCTGGACCCCTATCGCTAT
CCATTGAAGCTCGTCCAAGAGGTTGTCTCTTATCTCCACAAGCACAACCA
GCACTACATCATGATGGTGGACCCTGCAGTGGCATACCAGAACTATTCAG
CGTTCAACAACGGCGTCGCTGCCGACGCTTTCCTGAAGTTCTCGAATGGC
TCCATCTACCAGGGTGTCGTCTGGCCGGGGCCGACGGCGTTCCCGGACTG
GTTCGCACCCCAGACACAGGAGTTTTGGAATAGCGAGTTCTCGACCTTCT
TTGACCCCGCCCACGGCGTCGACATCGATGCCCTTTGGATCGACATGAAC
GAGGCGTCCAACTTCTGCGACTTTCCCTGCTCGAACCCCGCCGCGTATGC
GGCAGCCAACGGCGATCCGCCCACGCCTCCGCCGGTCCGCTTGAGCCCCC
CGAGGCCGATTCCTGGATTTGGCCCTGACTTCCAGCCGACGTGTGTCGCC
ACGGTGTCGTTCGATTGCGATGCGCAGACCTACTTTGGCGAGAACATCCT
CATCCTGGGTAACTCGACGACACTGGGAGCCGGCGACGTTCACATGGCGC
CAGTCATGAGCGCGAACAACTACCCGATCTGGCAGCTGACCGTCCAGATG
CCGCCGAATGGGACGTTCTCGTACCAGTACGTTCGCAAGGAATCGGACGG
CAGTTACATCTACGAACAGACGAATCGCACGGTCACGACGGGCGACTGCA
CCAGCGGCACGCTTAAGGTGTCCGACACCATCACCACCAGCTCTGGACCG
CACAAGAGATCCGAATTACGGCCGCTGGTGCGCTCGCCGTTCCCGGCGGA
GGACCTGACCAGGCGCCAGTCTGGATCGATGTTGGGCCTGCCCAACAGGA
ACCTGCTGAATCCGCCATACACCATCCACAATGCGGCTGGCAACCTGAGT
GAGAAGACCATCAACACCGACCTGATCCATGCGGGCGGATATGCCGAGTA
CGACACGCACAACTTGTACGGCACGATGATGAGCGCGACCAGCAGGGAGG
CGATGCTGAACCGCAGACCAGCAGTCAGGCCACTTGTGTAAGTCATCCAT
CGTCCTTAAGCCAGACACAGCATGTTAGGGGCTAACGGGCAGTAGCATTA
CCCGGTCGACCTTCGCTGGAGCCGGCCGACAGGTCGGCCACTGGCTCGGC
GACAATTTCGCCGATTGGGACCACTACCGGTGGACGATCGCCGAGCTGCA
GGAATTCGCGGCGCTGTTCCAGATCCCGATGGTCGGCAGCGACATCTGCG
GGTACGACGGCAACACGACGGACAACCTGTGCTCGCGCTGGGTCTTCCTC
GGCGCCTTCTCGCCCTTCTTCCGCGACCACTCGGACAACCAGTCGCCGCC
GCACGAGCTGTACCGCACTCCGCAGATCGCGGCGGCCGCGCGCGCCGCCA
TCGACATCCGCTACCGTCTGCTCGACTACGCGTACACGGTGCTGTGGACG
CAGACCCAGACCGGCGCGCCGATGCTCAACCCCATGTTCTTCGAGTACCC
GGCCGACAGCAACACCGCCGACCTGCAGTACCAGTTCTTCTGGGGCGACA
GCATCATGGTCGCGCCCGTGACCGACAACGACTCGACCACCGTCAACGTC
TACTTCCCGAAGGACCAGTTCTACGACTTCTACACCGGCGCACCTGTGTC
CGGGGAGGGCAATACCGTCACCCTGACCGACGTCGGCTTCGACACCATCC
CGCTGTACTTCAAGGGCGGGAGCATCGTGCCCATGCGCGTGCGCTCGGCG
AACACGACGGCGGAGCTGCGGCAGCAGGACTTCGTCGTCGTCATCGCCCC
GGACAGCCACGGCGACGCGACGGGCCAGCTGTACCTCGACGACGGCGAGA
GCATCAACCAGCCGCACACCAGCGAGATCCAGTTCTCGTACCGCGGAGGC
CATTTCAGCATGACAGGCAAGTTTGACTATGATCCCGGCAACGTGGTCAT
CAGCCAGATCACGCTGCTGGGTCGGACGGCGCCGGTAAAGGGGGTTCGT
ATAACAGCACCACCAAGGTGGCGACCTACAAAGTCAACGCGAAGTTGACG
GGTAAATTCGAAGCCAGCTTACACTAA
```

The amino acid sequence of the TauSec098 precursor protein is set forth as SEQ ID NO: 3. The predicted signal sequence is shown in italics and lowercase.

*mrptslvkhlastallflaada*AAIVRRNGASPSCPGYKASNVKTVDGEI
VSADLNLAGPACNVYGTDLDDLKLQVEYQSGPGVRADCLLPFDVTGTVRL
VDNDLTSAEQRLHVKIYDAAEQVYQVPTAVLPRPSSANIPPAKSDLKFSM
TNDPFSFTIKRRSNGEILFDTSGHPLIFESQYLGLRTKLPDSPNIYGLGE
HTGSFRLPTKNYTRTLWSRDAYGTPKDTNLYGNHPVYFDYRGSNGTHGVF
LLNSNGMDVDIDVDSDGQYLQYNTLGGVLDFYFLSGPDPKAVATQYAETV
GKPVMMPYWGFGFHNCRYGYQDIYEVAEIIANYSAANIPLETQWTDIDYM
DLRKVFTLDPYRYPLKLVQEVVSYLHKHNQHYIMMVDPAVAYQNYSAFNN
GVAADAFLKFSNGSIYQGVVWPGPTAFPDWFAPQTQEFWNSEFSTFFDPA
HGVDIDALWIDMNEASNFCDFPCSNPAAYAAANGDPPTPPPVRLSPPRPI
PGFGPDFQPTCVATVSFDCDAQTYFGENILILGNSTTLGAGDVHMAPVMS
ANNYPIWQLTVQMPPNGTFSYQYVRKESDGSYIYEQTNRTVTTGDCTSGT
LKVSDTITTSSGPHKRSELRPLVRSPFPAEDLTRRQSGSMLGLPNRNLLN
PPYTIHNAAGNLSEKTINTDLIHAGGYAEYDTHNLYGTMMSATSREAMLN
RRPAVRPLVITRSTFAGAGRQVGHWLGDNFADWDHYRWTIAELQEFAALF
QIPMVGSDICGYDGNTTDNLCSRWVFLGAFSPFFRDHSDNQSPPHELYRT
PQIAAAARAAIDIRYRLLDYAYTVLWTQTQTGAPMLNPMFFEYPADSNTA
DLQYQFFWGDSIMVAPVTDNDSTTVNVYFPKDQFYDFYTGAPVSGEGNTV
TLTDVGFDTIPLYFKGGSIVPMRVRSANTTAELRQQDFVVVIAPDSHGDA
TGQLYLDDGESINQPHTSEIQFSYRGGHFSMTGKFDYDPGNVVISQITLL
GADGAGKGGSYNSTTKVATYKVNAKLTGKFEASLH The amino acid sequence of the predicted mature form of TauSec098 is set forth as SEQ ID NO: 4.

AAIVRRNGASPSCPGYKASNVKTVDGEIVSADLNLAGPACNVYGTDLDDL
KLQVEYQSGPGVRADCLLPFDVTGTVRLVDNDLTSAEQRLHVKIYDAAEQ

-continued
VYQVPTAVLPRPSSANIPPAKSDLKFSMTNDPFSFTIKRRSNGEILFDTS

GHPLIFESQYLGLRTKLPDSPNIYGLGEHTGSFRLPTKNYTRTLWSRDAY

GTPKDTNLYGNHPVYFDYRGSNGTHGVFLLNSNGMDVDIDVDSDGQYLQY

NTLGGVLDFYFLSGPDPKAVATQYAETVGKPVMMPYWGFGEHNCRYGYQD

IYEVAEIIANYSAANIPLETQWTDIDYMDLRKVFTLDPYRYPLKLVQEVV

SYLHKHNQHYIMMVDPAVAYQNYSAFNNGVAADAFLKFSNGSIYQGVVWP

GPTAFPDWFAPQTQEFWNSEFSTFFDPAHGVDIDALWIDMNEASNECDFP

CSNPAAYAAANGDPPTPPPVRLSPPRPIPGFGPDFQPTCVATVSFDCDAQ

TYFGENILILGNSTTLGAGDVHMAPVMSANNYPIWQLTVQMPPNGTFSYQ

YVRKESDGSYIYEQTNRTVTTGDCTSGTLKVSDTITTSSGPHKRSELRPL

VRSPFPAEDLTRRQSGSMLGLPNRNLLNPPYTIHNAAGNLSEKTINTDLI

HAGGYAEYDTHNLYGTMMSATSREAMLNRRPAVRPLVITRSTFAGAGRQV

GHWLGDNFADWDHYRWTIAELQEFAALFQIPMVGSDICGYDGNTTDNLCS

RWVFLGAFSPFFRDHSDNQSPPHELYRTPQIAAAARAAIDIRYRLLDYAY

TVLWTQTQTGAPMLNPMFFEYPADSNTADLQYQFFWGDSIMVAPVTDNDS

TTVNVYFPKDQFYDFYTGAPVSGEGNTVTLTDVGFDTIPLYFKGGSIVPM

RVRSANTTAELRQQDFVVVIAPDSHGDATGQLYLDDGESINQPHTSEIQF

SYRGGHFSMTGKFDYDPGNVVISQITLLGADGAGKGGSYNSTTKVATYKV

NAKLTGKFEASLH

Example 2

Expression of Alpha-Glucosidase TauSec098

The synthetic TauSec098 gene was cloned into a *Trichoderma reesei* expression vector pGXT (the same as the pTTTpyr2 vector as described in published PCT Application WO2015/017256, incorporated by reference here) by Generay (Generay Biotech Co., Ltd, Shanghai, China) and the resulting plasmid was labeled pGX256-TauSec098. A plasmid map of pGX256-TauSec098 is provided in FIG. 1. The sequence of the TauSec098 gene was confirmed by DNA sequencing.

The plasmid pGX256-TauSec098 was transformed into a quad-deleted *Trichoderma reesei* strain (described in published PCT application WO 05/001036) using protoplast transformation (Te'o et al. (2002) J. Microbiol. Methods 51:393-99). Transformants were selected on a medium containing acetamide as a sole source of nitrogen (acetamide 0.6 g/L; cesium chloride 1.68 g/L; glucose 20 g/L; potassium dihydrogen phosphate 15 g/L; magnesium sulfate heptahydrate 0.6 g/L; calcium chloride dihydrate 0.6 g/L; iron (II) sulfate 5 mg/L; zinc sulfate 1.4 mg/L; cobalt (II) chloride 1 mg/L; manganese (II) sulfate 1.6 mg/L; agar 20 g/L; pH 4.25). Transformed colonies (about 50-100) appeared in about 1 week.

After growth on acetamide plates, the spores of transformants were collected and transferred into new acetamide agar plates. After 5 days of growth on acetamide plates, $1 \times 10^8$ spores were inoculated into 30 ml Glucose/Sophorose defined media in 250 ml shake flask. The shake flask was shaked at 28° C. for 5 days. Supernatants from these cultures were used to confirm the protein expression by SDS-PAGE analysis and assay for enzyme activity.

Example 3

Synthesis of TauSec099 Gene

A second polypeptide of SEQ ID NO:5 was identified as potentially encoding for another alpha glucosidase. This second polypeptide was named TauSec099.

The corresponding protein encoded by the TauSec099 gene is depicted in SEQ ID NO: 7.

Annotation of TauSec099 indicated that it most likely belongs to Glycosyl hydrolases family 31 based on the PFAM search (http://pfam.sanger.ac.uk/). It was also noted that, at the N-terminus, the protein has a signal peptide with a length of 17 amino acids as predicted by SignalP version 4.0 (Petersen et al. (2011) Nature Methods, 8:785-786). The presence of a signal sequence suggests that TauSec099 is a secreted enzyme.

The nucleotide sequence of the TauSec099 gene is set forth as SEQ ID NO: 5. The predicted signal sequence is shown in italics and lowercase.

*atggcaggctccgccgcccttgttgccagcctcgtctggcttgctcaggc* cTTCGACGCTCTTGCAGGACCGGTCAGCAGTACGACTGCCGCAGCACCAT

CTGCTCAATTCACCGTCCCGGCCGCTGCGGATGTTGGGGCCAACTTGCTT

GCCAACATCGACGATCCCAATGCCGTCAACGCCCAGGATGTCTGTCCCGG

TTACACGGCGTCGAACGTGCAGAACACCGAGTCTGGGTTTGTGGCGACCC

TGACGCTGGCGGGGAAACCATGTAATGTGTACGGAACGGACGTGGAGTCC

CTGAACCTGACGGTTGAGTACCAAGCTGCGGATCGACTGAACATCAATAT

CGTCCCGACGCACGTCGATTCTTCAAACCAGTCGTGGTATCTGCTTCCCG

AAAATGTAGTGCCCAAACCGGGGGTCGATGCAGGAGCCCAAGTCCCGGAG

AGTGATCTCGTCTTCAGCTGGTCGAATGAACCCTCCTTCAATTTCAAGGT

GATCCGGAAAGCCACAGGCGACATTCTCTTCGACACGGAGGGTTCTGTCC

TGGTGTTCGAAAACCAGTTCATCGAGTTTGCGAGCGCTCTGCCGGAGAAC

TACAATCTCTACGGTCTGGGAGAGCGTATCCATGGCTGCGACTGGGGAA

CAACTTCACCGCCACGACGTATGCCGCGGATAGCGCAGACCCTATTGACC

GGTGAGTATCTGAGATCGACTGCTCAGTCTGCTCTGTTGGATCTGAAAGA

AGTTATAAAACTGACCTAGCTCAGGAACATCTACGGGACCCATCCCTTTT

ATCTGGACACCCGGTACTACGAGGTTGATTCCGAGCATGGGAGGTTCACG

TTGGTGACGGACAACGAGACCGATTTCTCCAAGGAATATCTGTCGCTCTC

GCATGGAGTTTTCCTGAGAAATGCCCACGGACAGGAGGTGCTGCTGCGTC

CTCAGAGCATCACCTGGCGGACACTCGGTGGCAGCATTGATCTTTACTTC

TACGCCGGTCCGACCCAGGCCGATGTTACCCGCAGCTACCAGACCAGCAC

CGTTGGCCTCCCGGCAATGCAGCAGTACTTCACCCTGGGCTATCATCAGT

GCCGCTGGGGATACAGAAACTGGTCGGAGCTAGCTGATGTAGTGGCCAAT

TTCGAGAAATTCGAGATCCCATTGGAAAATATCTGGTAAGGCATACGCTA

TCTGAAAGAGTTGCTGGGAAAGTGATCTGACAACTTCGTCTCTCCAGGTC

GGATATTGATTACATGAACGAGTACCGCGACTTTGAGAACGACCCGGTTC

GCTTCTCCTACAGCGAGGGAGCCAAATTCCTGGACCAGCTCCACAAGAGT

GGCCGTCACTACATCCCGATTGTGGACGCCGCGATCTATGACCCCAACCC

TAACAATGACTCCGACGCGTAAGTCTAGTCTTGTAGGGAGGTGATAGGGA
GTGGAGCTGACTTCTCGATTAGGTATGCGACATATGATCGAGGTTCTAAG
GACGATATCTGGTTGAAGAATCCCGACGGCAGCGTGTACATCGGAGCCGT
CTGGCCTGGCTACACAGTGTTCACCGATTGGCACCATCCAAAAGCCAACG
AGTGGTGGGCAAACGAGCTGGCTCTGTGGCACGAAAAGGTCGCTTTTGAC
GGAATCTGGCTGGACATGAACGAGGTCTCGTCCTTCTGCGTTGGCAGCTG
TGGAACAGGGAACCTGACCCTGAATCCCGTGCACCCGAACTTCGCGCTCC
CGGGAGAGCCTGGAGCTGTCATCTACGACTACCCCGAGGACTTCAACGTG
ACGAATGCCACGGCGGCGGCGTCTGCATCTGCCGCGTCCTCGAGCCAAGC
TGCTGCGACAGCGACAGCTACTTCTTCGTCCACGACTACCAGCTACCTGG
TGACCACGCCCACTCCTGGAGTGCGGAATGTCAACTACCCTCCCTATGTG
ATTAATCACGTGCAGGAGGGTCACGATCTCGCTGTTCACGCCGTCTCGCC
CAACGCAACCCATGTCGATGGTGTGCAGGAGTACGACGTGCACAATCTCT
GGGGCTACCAGGAGACAAATGCAACCTACCATGCCCTGCTGAGCATCTTC
CCCGGGAAGAGACCGTTCATCATCTCCCGTTCCACGTTCGCCGGCAGCGG
CAGATGGGCCGACACTGGGGTGGCGACAACGCCTCGAAATGGGCGTACA
TGTTCTTTTCTATCCCGCAGGCGCTATCGTTCTCGCTGTTCGGCATCCCC
ATGTTCGGCGTCGACACCTGCGGGTTCAACGGCAACTCGGACGAAGAGCT
GTGCAACCGCTGGATGCAGCTCTCCGCCTTCTTCCCCTTCTACCGCAACC
ACAACGTCCTGTCGGCCATCCCGCAGGAGCCCTATGTCTGGGCATCCGTC
ATCGAGGCGAGCAAGTCGGCAATGAGGATCCGCTACACCCTGCTCCCTTA
CCTCTACACACTGTTCTACCTCGCCCACACCACGGGGTCGACCGTCATGC
GTGCCTTGGCGTGGGAGTTCCCCAACGACCCGTCCCTCGCTGCCGTGGAC
CGGCAGTTCCTCCTGGGCCCGTCGCTGATGGTCGTCCCCGTGCTCGAGCC
GCAGGTCGATACCGTCAAGGGCGTCTTCCCGGGCGTTGCCCAGGGCCAAG
TCTGGTACGACTGGTACACGCAGACCGCGTTCGACGCGCAGCCAGGCGTG
AACACGACCATCTCCGCGCCGCTGGGCCACATCCCCGTGTTCGTCCGCGG
CGGGAGCGTGCTCCCCATGCAGCAGCCGGCACTGGTGACGCGGGACGTGC
GCAACAGCCCCTGGTCGCTGCTGGTCGCGCTGGGCAGCGACGGCACGGCC
TCGGACAGCTGTACGTGGACGACGGCGAGAGCATCACACCTCCGGCGTC
CCTGCACGTCGACTTCGTGGCGGCCAACTTCTCGACCCTCTTCGCGACGG
CCCGCGGTGCGTTCAAGGACAGCAACACGCTGGCTAACGTCACGGTGCTG
GGCGTCCCAGCCGCGCCGTCGTCTGCAGTCACTTGGAACAACGAGACGGT
TCCTTCGGAGTCGGTGTCGTACAATGCCACCTCCAAAGTCCTCGTGGTCA
ATGGACTGCAGAGTCTTACCCGTGACGGAGCCTGGAGCAGTGACTGGGTT
CTGAAGTGGTAA

The DNA coding sequence of the predicted mature form of TauSec099 is set forth as SEQ ID NO: 6.

TTCGACGCTCTTGCAGGACCGGTCAGCAGTACGACTGCCGCAGCACCATC
TGCTCAATTCACCGTCCCGGCCGCTGCGGATGTTGGGGCCAACTTGCTTG
CCAACATCGACGATCCCAATGCCGTCAACGCCCAGGATGTCTGTCCCGGT
TACACGGCGTCGAACGTGCAGAACACCGAGTCTGGGTTTGTGGCGACCCT
GACGCTGGCGGGGAAACCATGTAATGTGTACGGAACGGACGTGGAGTCCC
TGAACCTGACGGTTGAGTACCAAGCTGCGGATCGACTGAACATCAATATC
GTCCCGACGCACGTCGATTCTTCAAACCAGTCGTGGTATCTGCTTCCCGA
AAATGTAGTGCCCAAACCGGGGGTCGATGCAGGAGCCCAAGTCCCGGAGA
GTGATCTCGTCTTCAGCTGGTCGAATGAACCCTCCTTCAATTTCAAGGTG
ATCCGGAAAGCCACAGGCGACATTCTCTTCGACACGGAGGGTTCTGTCCT
GGTGTTCGAAAACCAGTTCATCGAGTTTGCGAGCGCTCTGCCGGAGAACT
ACAATCTCTACGGTCTGGGAGAGCGTATCCATGCCTGCGACTGGGGAAC
AACTTCACCGCCACGACGTATGCCGCGGATAGCGCAGACCCTATTGACCG
GTGAGTATCTGAGATCGACTGCTCAGTCTGCTCTGTTGGATCTGAAAGAA
GTTATAAAACTGACCTAGCTCAGGAACATCTACGGGACCCATCCCTTTTA
TCTGGACACCCGGTACTACGAGGTTGATTCCGAGCATGGGAGGTTCACGT
TGGTGACGGACAACGAGACCGATTTCTCCAAGGAATATCTGTCGCTCTCG
CATGGAGTTTTCCTGAGAAATGCCCACGGACAGGAGGTGCTGCTGCGTCC
TCAGAGCATCACCTGGCGGACACTCGGTGGCAGCATTGATCTTTACTTCT
ACGCCGGTCCGACCCAGGCCGATGTTACCCGCAGCTACCAGACCAGCACC
GTTGGCCTCCCGGCAATGCAGCAGTACTTCACCCTGGGCTATCATCAGTG
CCGCTGGGGATACAGAAACTGGTCGGAGCTAGCTGATGTAGTGGCCAATT
TCGAGAAATTCGAGATCCCATTGGAAAATATCTGGTAAGGCATACGCTAT
CTGAAAGAGTTGCTGGGAAAGTGATCTGACAACTTCGTCTCTCCAGGTCG
GATATTGATTACATGAACGAGTACCGCGACTTTGAGAACGACCCGGTTCG
CTTCTCCTACAGCGAGGGAGCCAAATTCCTGGACCAGCTCCACAAGAGTG
GCCGTCACTACATCCCGATTGTGGACGCCGCGATCTATGACCCCAACCCT
AACAATGACTCCGACGCGTAAGTCTAGTCTTGTAGGGAGGTGATAGGGAG
TGGAGCTGACTTCTCGATTAGGTATGCGACATATGATCGAGGTTCTAAGG
ACGATATCTGGTTGAAGAATCCCGACGGCAGCGTGTACATCGGAGCCGTC
TGGCCTGGCTACACAGTGTTCACCGATTGGCACCATCCAAAAGCCAACGA
GTGGTGGGCAAACGAGCTGGCTCTGTGGCACGAAAAGGTCGCTTTTGACG
GAATCTGGCTGGACATGAACGAGGTCTCGTCCTTCTGCGTTGGCAGCTGT
GGAACAGGGAACCTGACCCTGAATCCCGTGCACCCGAACTTCGCGCTCCC
GGGAGAGCCTGGAGCTGTCATCTACGACTACCCCGAGGACTTCAACGTGA
CGAATGCCACGGCGGCGGCGTCTGCATCTGCCGCGTCCTCGAGCCAAGCT
GCTGCGACAGCGACAGCTACTTCTTCGTCCACGACTACCAGCTACCTGGT
GACCACGCCCACTCCTGGAGTGCGGAATGTCAACTACCCTCCCTATGTGA
TTAATCACGTGCAGGAGGGTCACGATCTCGCTGTTCACGCCGTCTCGCCC
AACGCAACCCATGTCGATGGTGTGCAGGAGTACGACGTGCACAATCTCTG
GGGCTACCAGGAGACAAATGCAACCTACCATGCCCTGCTGAGCATCTTCC
CCGGGAAGAGACCGTTCATCATCTCCCGTTCCACGTTCGCCGGCAGCGGC

```
AGATGGGCCGGACACTGGGGTGGCGACAACGCCTCGAAATGGGCGTACAT

GTTCTTTTCTATCCCGCAGGCGCTATCGTTCTCGCTGTTCGGCATCCCCA

TGTTCGGCGTCGACACCTGCGGGTTCAACGGCAACTCGGACGAAGAGCTG

TGCAACCGCTGGATGCAGCTCTCCGCCTTCTTCCCCTTCTACCGCAACCA

CAACGTCCTGTCGGCCATCCCGCAGGAGCCCTATGTCTGGGCATCCGTCA

TCGAGGCGAGCAAGTCGGCAATGAGGATCCGCTACACCCTGCTCCCTTAC

CTCTACACACTGTTCTACCTCGCCCACACCACGGGGTCGACCGTCATGCG

TGCCTTGGCGTGGGAGTTCCCCAACGACCCGTCCCTCGCTGCCGTGGACC

GGCAGTTCCTCCTGGGCCCGTCGCTGATGGTCGTCCCCGTGCTCGAGCCG

CAGGTCGATACCGTCAAGGGCGTCTTCCCGGGCGTTGCCCAGGGCCAAGT

CTGGTACGACTGGTACACGCAGACCGCGTTCGACGCGCAGCCAGGCGTGA

ACACGACCATCTCCGCGCCGCTGGGCCACATCCCCGTGTTCGTCCGCGGC

GGGAGCGTGCTCCCCATGCAGCAGCCGGCACTGGTGACGCGGGACGTGCG

CAACAGCCCCTGGTCGCTGCTGGTCGCGCTGGGCAGCGACGGCACGGCCT

CGGGACAGCTGTACGTGGACGACGGCGAGAGCATCACACCTCCGGCGTCC

CTGCACGTCGACTTCGTGGCGGCCAACTTCTCGACCCTCTTCGCGACGGC

CCGCGGTGCGTTCAAGGACAGCAACACGCTGGCTAACGTCACGGTGCTGG

GCGTCCCAGCCGCGCCGTCGTCTGCAGTCACTTGGAACAACGAGACGGTT

CCTTCGGAGTCGGTGTCGTACAATGCCACCTCCAAAGTCCTCGTGGTCAA

TGGACTGCAGAGTCTTACCCGTGACGGAGCCTGGAGCAGTGACTGGGTTC

TGAAGTGGTAA
```

The amino acid sequence of the TauSec099 precursor protein is set forth as SEQ ID NO: 7. The predicted signal sequence is shown in italics and lowercase

```
magsaalvaslvwlaqaFDALAGPVSSTTAAAPSAQFTVPAAADVGANLL

ANIDDPNAVNAQDVCPGYTASNVQNTESGFVATLTLAGKPCNVYGTDVES

LNLTVEYQAADRLNINIVPTHVDSSNQSWYLLPENVVPKPGVDAGAQVPE

SDLVFSWSNEPSFNFKVIRKATGDILFDTEGSVLVFENQFIEFASALPEN

YNLYGLGERIHGLRLGNNFTATTYAADSADPIDRNIYGTHPFYLDTRYYE

VDSEHGRFTLVTDNETDFSKEYLSLSHGVFLRNAHGQEVLLRPQSITWRT

LGGSIDLYFYAGPTQADVTRSYQTSTVGLPAMQQYFTLGYHQCRWGYRNW

SELADVVANFEKFEIPLENIWSDIDYMNEYRDFENDPVRFSYSEGAKFLD

QLHKSGRHYIPIVDAAIYDPNPNNDSDAYATYDRGSKDDIWLKNPDGSVY

IGAVWPGYTVFTDWHHPKANEWWANELALWHEKVAFDGIWLDMNEVSSFC

VGSCGTGNLTLNPVHPNFALPGEPGAVIYDYPEDFNVTNATAAASASAAS

SSQAAATATATSSSTTTSYLVTTPTPGVRNVNYPPYVINHVQEGHDLAVH

AVSPNATHVDGVQEYDVHNLWGYQETNATYHALLSIFPGKRPFIISRSTF

AGSGRWAGHWGGDNASKWAYMFFSIPQALSFSLFGIPMFGVDTCGFNGNS

DEELCNRWMQLSAFFPFYRNHNVLSAIPQEPYVWASVIEASKSAMRIRYT

LLPYLYTLFYLAHTTGSTVMRALAWEFPNDPSLAAVDRQFLLGPSLMVVP

VLEPQVDTVKGVFPGVAQGQVWYDWYTQTAFDAQPGVNTTISAPLGHIPV

FVRGGSVLPMQQPALVTRDVRNSPWSLLVALGSDGTASGQLYVDDGESIT

PPASLHVDFVAANFSTLFATARGAFKDSNTLANVTVLGVPAAPSSAVTWN

NETVPSESVSYNATSKVLVVNGLQSLTRDGAWSSDWVLKW
```

The amino acid sequence of the predicted mature form of TauSec099 is set forth as SEQ ID NO: 8.

```
FDALAGPVSSTTAAAPSAQFTVPAAADVGANLLANIDDPNAVNAQDVCPG

YTASNVQNTESGFVATLTLAGKPCNVYGTDVESLNLTVEYQAADRLNINI

VPTHVDSSNQSWYLLPENVVPKPGVDAGAQVPESDLVFSWSNEPSFNEKV

IRKATGDILFDTEGSVLVFENQFIEFASALPENYNLYGLGERIHGLRLGN

NFTATTYAADSADPIDRNIYGTHPFYLDTRYYEVDSEHGRFTLVTDNETD

FSKEYLSLSHGVFLRNAHGQEVLLRPQSITWRTLGGSIDLYFYAGPTQAD

VTRSYQTSTVGLPAMQQYFTLGYHQCRWGYRNWSELADVVANFEKFEIPL

ENIWSDIDYMNEYRDFENDPVRFSYSEGAKFLDQLHKSGRHYIPIVDAAI

YDPNPNNDSDAYATYDRGSKDDIWLKNPDGSVYIGAVWPGYTVFTDWHHP

KANEWWANELALWHEKVAFDGIWLDMNEVSSFCVGSCGTGNLTLNPVHPN

FALPGEPGAVIYDYPEDFNVTNATAAASASAASSSQAAATATATSSSTTT

SYLVTTPTPGVRNVNYPPYVINHVQEGHDLAVHAVSPNATHVDGVQEYDV

HNLWGYQETNATYHALLSIFPGKRPFIISRSTFAGSGRWAGHWGGDNASK

WAYMFFSIPQALSFSLEGIPMFGVDTCGENGNSDEELCNRWMQLSAFFPF

YRNHNVLSAIPQEPYVWASVIEASKSAMRIRYTLLPYLYTLFYLAHTTGS

TVMRALAWEFPNDPSLAAVDRQFLLGPSLMVVPVLEPQVDTVKGVFPGVA

QGQVWYDWYTQTAFDAQPGVNTTISAPLGHIPVFVRGGSVLPMQQPALVT

RDVRNSPWSLLVALGSDGTASGQLYVDDGESITPPASLHVDEVAANFSTL

FATARGAFKDSNTLANVTVLGVPAAPSSAVTWNNETVPSESVSYNATSKV

LVVNGLQSLTRDGAWSSDWVLKW
```

Example 4

Expression of Alpha-Glucosidase TauSec099

The synthetic TauSec099 gene was cloned into the *Trichoderma reesei* expression vector pGXT by Generay (Generay Biotech Co., Ltd, Shanghai, China) and the resulting plasmid was labeled pGX256-TauSec099. A plasmid map of pGX256-TauSec099 is provided in FIG. 2. The sequence of the TauSec099 gene was confirmed by DNA sequencing.

The plasmid pGX256-TauSec099 was transformed into a quad-deleted *Trichoderma reesei* strain (described in published PCT application WO 05/001036) using protoplast transformation (Te'o et al. (2002) supra). Transformants were selected on a medium containing acetamide as a sole source of nitrogen (acetamide 0.6 g/L; cesium chloride 1.68 g/L; glucose 20 g/L; potassium dihydrogen phosphate 15 g/L; magnesium sulfate heptahydrate 0.6 g/L; calcium chloride dihydrate 0.6 g/L; iron (II) sulfate 5 mg/L; zinc sulfate 1.4 mg/L; cobalt (II) chloride 1 mg/L; manganese (II) sulfate 1.6 mg/L; agar 20 g/L; pH 4.25). Transformed colonies (about 50-100) appeared in about 1 week.

After growth on acetamide plates, the spores of transformants were collected and transferred into new acetamide agar plates. After 5 days of growth on acetamide plates, 1×10⁸ spores were inoculated into 30 mL Glucose/Sophorose defined media in 250 mL shake flask. The shake flask was shaked at 28° C. for 5 days. Supernatants from these cultures were used to confirm the protein expression by SDS-PAGE analysis and assay for enzyme activity.

Example 5

Purification of TauSec098 and TauSec099

Both TauSec098 and TauSec099 were purified via hydrophobic interaction chromatography, respectively.

About 180 mL concentrated crude broth from the shake flask fermentation was added ammonium sulphate to a final concentration of 1 M. This solution was then loaded onto a 50 mL HiPrep phenyl-FF Sepharose column (GE Healthcare) pre-equilibrated with 20 mM sodium acetate pH 5.0 with 1 M ammonium sulphate (buffer A). After washing with the same buffer for 3 column volumes (CVs), the column was eluted stepwise with 75%, 50% and 0% buffer A in 3 CVs each, followed by 2 CVs of MilliQ H2O. All fractions were analysed on SDS-PAGE.

The target protein was mainly present in the flow through fraction, which were concentrated and buffer exchanged to remove the excess ammonium sulfate using the 10 KDa Amicon Ultra-15 devices. The final product was above 90% pure and stored in 40% glycerol at −80° C. before use.

Example 6

Substrate Specificity of TauSec098 and TauSec099

Substrate specificities of TauSec098 and TauSec099 were assayed based on the release of glucose by alpha-glucosidase from isomaltose, maltose, panose, maltulose, sucrose, leucrose, nigerose, and kojibiose, respectively.

The rates of glucose release for both enzymes were measured using a coupled glucose oxidase/peroxidase (GOX/HRP) method (see, Ngo & Lenhoff (1980) Anal. Biochem. 105:389-397). Glucose was quantified as the rate of oxidation of 2,2'-Azino-bis 3-ethylbenzothiazoline-6-sulfonic acid (ABTS) by peroxide which was generated from coupled GOX/HRP enzymes reacted with glucose.

Substrate solutions were prepared by mixing 9 mL of each substrate mentioned above (1% in water, w/v), 1 mL of 0.5 M pH 5.0 sodium acetate buffer, and 40 µL of 0.5 M calcium chloride in a 15-mL conical tube. Coupled enzyme (GOX/HRP) solution with ABTS was prepared in 50 mM sodium acetate buffer (pH 5.0), with the final concentrations of 2.74 mg/mL ABTS, 0.1 U/mL HRP, and 1 U/mL GOX.

Serial dilutions of alpha-glucosidase samples and glucose standard were prepared in Milli Q water. For nigerose and kojibiose, alpha-glucosidase samples were tested with only one final dosage at 10 ppm due to limit stock of substrate solutions. Each alpha-glucosidase sample (10 µL) was transferred into a new microtiter plate (Corning 3641) containing 90 µL of substrate solution preincubated at 50° C. for 5 min at 600 rpm.

The reactions were carried out at 50° C. for 10 min (for isomaltose, maltose, panose, maltulose, nigerose, and kojibiose) and for 60 min (for sucrose and leucrose) with shaking (600 rpm) in a thermomixer (Eppendorf), 10 µL of reaction mixtures as well as 10 µL of serial dilutions of glucose standard were quickly transferred to new microtiter plates (Corning 3641), respectively, followed by the addition of 90 µL of ABTS/GOX/HRP solution. The microtiter plates containing the reaction mixture were immediately measured at 405 nm at 11 seconds intervals for 5 min on SoftMax Pro plate reader (Molecular Device). The output was the reaction rate, Vo, for each enzyme concentration. Linear regression was used to determine the slope of the plot Vo vs. enzyme dose. The specific activity of alpha-glucosidase was calculated based on the glucose standard curve using Equation 1:

$$\text{Specific Activity (Unit/mg)} = \text{Slope (enzyme)/slope (std)} \times 1000 \quad (1),$$

where 1 Unit=1 µmol glucose/min.

For nigerose and kojibiose, the value of the reaction rate with enzyme dosage at 10 ppm was directly used to indicate the enzyme activity. Using the method mentioned above, substrate specificity of TauSec098 and TauSec099 was determined compared with benchmarks, Oligo-1,6-glucosidase (a product purchased from Megazyme) and TrTG (purified from DuPont product, TG L-2000) as shown in Table 2.

TABLE 2

Substrate specificity of purified TauSec 098 and TauSec099 compared with Oligo-1,6-glucosidase and TrTG.

| Enzyme | Activity on Isomaltose (U/mg) | Activiy on Maltose (U/mg) | Activity on Panose (U/mg) | Activity on Maltulose (U/mg) | Activity on Sucrose (U/mg) | Activity on Leucrose (U/mg) | Activity on Nigerose (10 ppm) | Activity on Kojibiose (10 ppm) |
|---|---|---|---|---|---|---|---|---|
| Oligo-1,6-glucosidase | 118.2 | 0.0 | 54.3 | 11.8 | 1.8 | 1.3 | 19.6 | 23.5 |
| TrTG purified | 194.0 | 235.6 | 127.7 | 3.5 | 0.0 | 68.9 | 254.0 | 165.8 |
| TauSec098 | 54.9 | 123.8 | 23.8 | 21.7 | 2.4 | 1.8 | 305.6 | 270.1 |
| TauSec099 | 244.0 | 97.7 | 50.8 | 4.6 | 0.3 | 70.6 | 184.8 | 128.7 |

Example 7 pH Effect on Alpha-Glucosidase Activity of TauSec098 and TauSec099

The effect of pH (from 3.0 to 10.0) on alpha-glucosidase activity of TauSec098 and TauSec099 was monitored using isomaltose as a substrate, respectively. Buffer working solutions consisted of the combination of glycine/sodium acetate/HEPES (250 mM), with pH varying from 3.0 to 10.0. Substrate solutions were prepared by mixing isomaltose (1% in water, w/v) with 250 mM buffer solution at a ratio of 9:1, containing calcium chloride at a final concentration of 2 mM. Enzyme working solutions were prepared in water at a certain dose (showing signal within linear range as per dose response curve). All the incubations were carried out at 50° C. for 10 min following the same protocol as described above for activity of alpha-glucosidase to isomaltose substrate. Enzyme activity at each pH was reported as relative activity compared to enzyme activity at optimum pH. The pH profiles of TauSec098 and TauSec099 were shown in Table 3. TauSec098 and TauSec099 were found to both have an optimum pH at 4.0 and retain greater than 70% of maximum activity between pH<3.0 and 5.8 for TauSec098 and pH<3.0 and 5.4 for TauSec099.

TABLE 3 pH profiles for TauSec098 and TauSec099

| pH | Relative activity (%) | |
|---|---|---|
|  | TauSec098 | TauSec099 |
| 3 | 84 | 97 |
| 4 | 100 | 100 |
| 5 | 89 | 83 |
| 6 | 66 | 51 |
| 7 | 43 | 26 |
| 8 | 20 | 7 |
| 9 | 9 | 2 |
| 10 | 2 | 0 |

Example 8

Temperature Effect on Alpha-Glucosidase Activity of TauSec098 and TauSec099

The effect of temperature (from 40° C. to 84° C.) on α-glucosidase activity of TauSec098 and TauSec099 was monitored using isomaltose as a substrate, respectively. Substrate solutions were prepared by mixing 9 mL of isomaltose (1% in water, w/v), 1 mL of 0.5 M pH 5.0 sodium acetate buffer, and 40 μL of 0.5 M calcium chloride in a 15-mL conical tube. Enzyme working solutions were prepared in water at a certain dose (showing signal within linear range as per dose response curve). Incubations were done at temperatures from 40° C. to 84° C., respectively, for 10 min following the same protocol as described above for activity of alpha-glucosidase towards isomaltose. Activity at each temperature was reported as relative activity compared to enzyme activity at optimum temperature. The temperature profiles of TauSec098 and TauSec099 were shown in Table 4. TauSec098 and TauSec099 were found to both have an optimum temperature at 69° C. and were able to keep higher than 70% of maximum activity between 58° C. and 80° C. for TauSec098 and 58° C. and 77° C. for TauSec099.

TABLE 4

Temperature- activity profile of TauSec098 and TauSec099

| Temp. (° C.) | Relative activity (%) | |
|---|---|---|
|  | TauSec098 | TauSec099 |
| 40 | 32 | 24 |
| 44.7 | 41 | 31 |
| 49.4 | 50 | 42 |
| 55 | 62 | 60 |
| 59.7 | 73 | 73 |
| 65 | 90 | 90 |
| 69.2 | 100 | 100 |
| 74.6 | 99 | 100 |
| 80 | 68 | 34 |
| 85 | 33 | 19 |

Example 9

Evaluations of Alpha-Glucosidase Activities of TauSec098 and TauSec099

It was known that, in grain or starch processing, typically in the context of producing grain ethanol, the residual starch hydrolysis at the end of liquefaction (EoL) the end of saccharification (EoS), and the end of fermentation (EoF) could pose significant technical challenges to plant operation.

In this experiment, the alpha-glucosidase activities of TauSec098 and TauSec099 and the effects of including such alpha-glucosidases in a grain ethanol process were evaluated. The EoL, EoS, and EoF monosaccharide levels were measured.

EoL, EoS, EoF grain processing samples were prepared. Oligo-1,6-glucosidase was purchased from Megazyme, and a *Trichoderma* transglucosidase product (Genencor, DuPont) were used as benchmarks. Substrate only, with no addition of enzymes, was used as a negative control sample.

The alpha-glucosidases were dosed at 100 ppm, and a 10% dry solids sample each of EoL, EoS, and EoF were incubated at pH 4.5, in the presence of 2 mM calcium chloride, at the temperatures of 32° C. for EoF sample, 60° C. for EoL and EoS samples. Reactions were quenched by adding 80 μL 0.5 M NaOH after 21 hours of incubation. Supernatants of the samples were transferred and diluted 10× in water before they were put to analyses by HPLC.

HPLC analyses were carried out using an Agilent 1200 series system with an Aminex HPX-42A column having the dimension of 300 mm×7.8 mm, at 85° C. Samples of 10 μL were put to the HPLC column and separated using an isocratic gradient of Milli-Q water as the mobile phase at a flow rate of 0.6 ml/min.

The oligosaccharide products were detected using a refractive index detector. Table 5 below lists the average of peak area percentages of each DPn as a fraction of the total of DP1 to DP3+.

TABLE 5

Sugar composition analyses of TauSec 098 and TauSec099 on residual starch hydrolysis of EoL, EoS and EoF samples.

| Substrate | Temp. (° C.) | Enzyme | DP3+ % | DP3 % | DP2 % | DP1 % |
|---|---|---|---|---|---|---|
| EoF-Corn | 32 | Oligo-1,6-glucosidase | 79.6 | 0.2 | 4.8 | 15.3 |
|  |  | TG purified | 71.7 | 0.5 | 1.5 | 26.3 |
|  |  | TauSec098 | 74.9 | 0.4 | 6.0 | 18.7 |
|  |  | TauSec099 | 77.0 | 0.4 | 4.7 | 17.8 |
|  |  | blank | 73.5 | 0.5 | 8.8 | 17.2 |
| EoF-Wheat | 32 | Oligo-1,6-glucosidase | 77.8 | 1.7 | 5.0 | 15.4 |
|  |  | TG purified | 71.7 | 1.3 | 4.1 | 23.0 |
|  |  | TauSec098 | 74.6 | 0.7 | 5.8 | 18.9 |
|  |  | TauSec099 | 77.2 | 0.8 | 4.1 | 17.9 |
|  |  | blank | 68.7 | 1.8 | 19.3 | 10.2 |

TABLE 5-continued

Sugar composition analyses of TauSec 098 and TauSec099 on residual starch hydrolysis of EoL, EoS and EoF samples.

| Substrate | Temp. (° C.) | Enzyme | DP3+ % | DP3 % | DP2 % | DP1 % |
|---|---|---|---|---|---|---|
| EoL-Wheat | 60 | Oligo-1,6-glucosidase | 58.2 | 10.5 | 25.0 | 6.3 |
| | | TG purified | 25.5 | 0.0 | 2.8 | 71.7 |
| | | TauSec098 | 23.4 | 1.5 | 6.3 | 68.7 |
| | | TauSec099 | 26.4 | 0.1 | 2.4 | 71.1 |
| | | blank | 57.1 | 11.0 | 25.6 | 6.4 |
| EoS-Corn | 60 | Oligo-1,6-glucosidase | 2.4 | 0.3 | 2.2 | 95.1 |
| | | TG purified | 1.2 | 0.6 | 9.6 | 88.6 |
| | | TauSec098 | 1.4 | 0.4 | 2.8 | 95.4 |
| | | TauSec099 | 1.4 | 0.8 | 10.7 | 87.1 |
| | | blank | 1.3 | 0.4 | 2.0 | 96.3 |

What is claimed is:

1. A non-native polypeptide comprising an amino acid sequence that is at least 97% identical to, but not 100% identical to, the amino acid sequence of SEQ ID NO:4 or 8, wherein the non-native polypeptide has alpha-glucosidase activity.

2. The non-native polypeptide of claim 1, wherein the non-native polypeptide comprises an amino acid sequence that is at least 98% identical to the amino acid sequence of SEQ ID NO:4 or 8.

3. The non-native polypeptide of claim 2, wherein the non-native polypeptide comprises an amino acid sequence that is at least about 98% 99% identical to the amino acid sequence of SEQ ID NO:4 or 8.

4. A composition comprising the non-native polypeptide of any one of claims 1-3 and one or more of an alpha-amylase, a beta-amylase, a glucoamylase, a pullulanase, an isoamylase, a different alpha-glucosidase, and/or a cyclodextrin glycosyltransferase.

5. The non-native polypeptide of claim 1, wherein the non-native polypeptide comprises an amino acid sequence that is at least 97% identical to the amino acid sequence of SEQ ID NO:4.

6. The non-native polypeptide of claim 5, wherein the non-native polypeptide comprises an amino acid sequence that is at least 98% identical to the amino acid sequence of SEQ ID NO:4.

7. A polynucleotide encoding the non-native polypeptide of any one of claims 1-3, 5, or 6.

8. The polynucleotide of claim 7, comprising at least one transcriptional or translational regulatory sequence that allows the polynucleotide sequence to be expressed by a host cell.

9. The polynucleotide of claim 8, wherein the polynucleotide comprises a transcriptional regulatory sequence that is a promoter sequence.

10. A host cell comprising the polynucleotide of claim 9.

11. The host cell of claim 10, which is a *Trichoderma* or *Aspergillus* host cell.

12. The host cell of claim 10, which is an *E. coli, Bacillus, Streptomyces,* or *Pseudomonas* cell.

13. The host cell of claim 10, which is a yeast cell.

14. A method of making a polypeptide, the method comprising cultivating the host cell of claim 10, wherein said polypeptide having alpha-glucosidase activity is produced by the host cell.

15. The method of claim 14, further comprising a step of recovering, enriching and/or purifying the polypeptide.

16. A polynucleotide comprising a nucleotide sequence that encodes a polypeptide having alpha-glucosidase activity, wherein the polypeptide comprises an amino acid sequence that is at least 97% identical to the amino acid sequence of SEQ ID NO:4 or 8, and wherein the nucleotide sequence is
   (i) a complementary DNA (cDNA) sequence, and/or
   (ii) operably linked to at least one transcriptional or translational regulatory sequence that is heterologous to the nucleotide sequence.

17. The polynucleotide of claim 16, wherein the polypeptide comprises an amino acid sequence that is at least 98% identical to the amino acid sequence of SEQ ID NO:4 or 8.

18. The polynucleotide of claim 17, wherein the polypeptide comprises an amino acid sequence that is at least 99% identical to the amino acid sequence of SEQ ID NO:4 or 8.

19. The polynucleotide of claim 16, wherein the polypeptide comprises an amino acid sequence that is at least 97% identical to the amino acid sequence of SEQ ID NO:4.

20. The polynucleotide of claim 19, wherein the polypeptide comprises an amino acid sequence that is at least 98% identical to the amino acid sequence of SEQ ID NO:4.

21. The polynucleotide of any one of claims 16-20, wherein the nucleotide sequence is operably linked to at least one transcriptional or translational regulatory sequence that is heterologous to the nucleotide sequence.

22. The polynucleotide of claim 21, wherein the nucleotide sequence is operably linked to a transcriptional regulatory sequence that is a promoter sequence.

23. A host cell comprising the polynucleotide of claim 22.

24. A method of making a polypeptide, the method comprising cultivating the host cell of claim 23, wherein said polypeptide having alpha-glucosidase activity is produced by the host cell.

* * * * *